US008912324B2

(12) United States Patent
Holladay et al.

(10) Patent No.: US 8,912,324 B2
(45) Date of Patent: *Dec. 16, 2014

(54) OPTICALLY ACTIVE PYRAZOLYLAMINOQUINAZOLINE, AND PHARMACEUTICAL COMPOSITIONS AND METHODS OF USE THEREOF

(75) Inventors: Mark W. Holladay, San Diego, CA (US); Eduardo Setti, San Mateo, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/222,963

(22) Filed: Aug. 31, 2011

(65) Prior Publication Data

US 2012/0053193 A1     Mar. 1, 2012

Related U.S. Application Data

(60) Provisional application No. 61/379,280, filed on Sep. 1, 2010, provisional application No. 61/379,286, filed on Sep. 1, 2010.

(51) Int. Cl.

| *C07D 417/00* | (2006.01) |
|---|---|
| *C07D 419/00* | (2006.01) |
| *C07D 403/12* | (2006.01) |
| *A61K 31/517* | (2006.01) |

(52) U.S. Cl.
CPC ............ *C07D 403/12* (2013.01); *A61K 31/517* (2013.01)
USPC ....................................................... 544/284

(58) Field of Classification Search
CPC .. C07D 239/91; C07D 401/12; C07D 401/04; C07D 239/95; C07D 401/06
USPC ....................................................... 544/284
See application file for complete search history.

(56) References Cited

U.S. PATENT DOCUMENTS

| 2005/0038023 A1 | 2/2005 | Bebbington et al. |
| 2008/0269490 A1 | 10/2008 | Chan et al. |
| 2010/0317659 A1 | 12/2010 | Abraham et al. |

FOREIGN PATENT DOCUMENTS

| WO | 2004015142 A1 | 2/2004 |
| WO | 2008005310 A2 | 1/2008 |
| WO | 2010099379 A1 | 9/2010 |

OTHER PUBLICATIONS

Mehmetoğlu et al. (Production of Enantiomerically pure Pharmaceutical compounds using biocatalysts 2007).*
Khan et al., "Signal enantiomer drugs: Should they be developed?" Essential Psychopharmacology 2006, 7, 15-23.
Kiss et al., "Recent developments on JAK2 inhibitors: a patent review," Expert Opin. Ther. Patents 2010, 20, 471-495.
Barton et al., "Signal transducer and activator of transcription 3 (STAT3) activation in prostate cancer: Direct STAT3 inhibition induces apoptosis in prostate cancer lines," Mol. Cancer. Ther. 2004, 3, 11-20.
Baxter et al., "Acquired mutation of the tyrosine kinase JAK2 in human myeloproliferative disorders," Lancet 2005, 365, 1054-1056.
Beresford et al., "Pharmacological characterisation of melatonin mt1 receptor-mediated stimulation of [35S]-GTPgammaS binding," Biochem. Pharmacol. 1998, 56, 1167-1174.
Blume-Jensen et al., "Oncogenic kinase signaling," Nature 2001, 411, 355-365.
Borie et al., "Immunosuppression by the JAK3 inhibitor CP-690,550 delays rejection and significantly prolongs kidney allograft survival in nonhuman primates," Transplantation 2005, 79, 791-801.
Bousquet et al., "The t(8;9)(p22;p24) translocation in atypical chronic myeloid leukaemia yields a new PCM1-JAK2 fusion gene," Oncogene 2005, 24, 7248-7252.
Bromberg et al., "Stat proteins and oncogenesis," J. Clin. Invest. 2002, 109, 1139-1142.
Campbell et al., "V617F mutation in JAK2 is associated with poorer survival in idiopathic myelofibrosis," Blood 2006, 107, 2098-2100.
Cheng et al., "Relationship between the inhibition constant (Ki) and the concentration of inhibitor which causes 50 per cent inhibition (I50) of an enzymatic reaction," Biochem. Pharmacol. 1973, 22, 3099-3108.
Cho, "Recent development and improvement for boron hydride-based catalytic asymmetric reduction of unsymmetrical ketones," Chem. Soc. Rev. 2009, 38, 443-452.
Corey et al., "Asymmetric synthesis of (S)-carbinoxamine. New aspects of oxazaborolidine-catalyzed enantioselective carbonyl reduction," Tetra. Lett. 1996, 37, 5675-5678.
Cortijo et al., "Investigation into the role of phosphodiesterase IV in bronchorelaxation, including studies with human bronchus," Br. J. Pharmacol. 1993, 108, 562-568.
Daubmann et al., "Oxidoreductases and hydroxynitrilase lyases: Complementary enzymatic technologies for chiral alcohols," Engineering in Life Science 2006, 6, 125-129.
Fabian et al., "A small molecule-kinase interaction map for clinical kinase inhibitors," Nat. Biotechnol. 2005, 23, 329-336.
Griesinger et al., "A BCR-JAK2 fusion gene as the result of a t(9;22)(p24;q11.2) translocation in a patient with a clinically typical chronic myeloid leukemia," Genes Chromosomes Cancer 2005, 44, 329-333.
Hidaka et al., "Human blood platelet 3':5'-cyclic nucleotide phosphodiesterase. Isolation of low-Km and high-Km phosphodiesterase," Biochem. Biophys. Acta 1976, 429, 485-497.
Jacobson et al., "Pharmacological characterization of novel A3 adenosine receptor-selective antagonists," Neuropharmacology 1997, 36, 1157-1165.

*Primary Examiner* — Shirley V Gembeh
(74) *Attorney, Agent, or Firm* — Jones Day

(57) ABSTRACT

Provided herein is an optically active pyrazolylaminoquinazoline, and pharmaceutical compositions thereof. Also provided herein is a method for treating, preventing, or ameliorating one or more symptoms of a JAK-mediated condition, disorder, or disease. Further provided herein is a method for treating, preventing, or ameliorating one or more symptoms of a proliferative disease, inflammatory disease, or renal disease.

19 Claims, 5 Drawing Sheets

(56) References Cited

OTHER PUBLICATIONS

Jones et al., "Widespread occurrence of the JAK2 V617F mutation in chronic myeloproliferative disorders," Blood 2005, 106, 2162-2168.

Kambourakis and Rozzell, "Ketoreductases: General stereoselective catalysts for the facile synthesis of a broad range of chiral alcohols," PharmaChem 2006, 5, 2-5.

Lacronique et al., "A TEL-JAK2 fusion protein with constitutive kinase activity in human leukemia," Science 1997, 278, 1309-1312.

Lacronique et al., "Transforming properties of chimeric TEL-JAK proteins in Ba/F3 cells," Blood 2000, 95, 2076-2083.

Levine et al., "X-inactivation-based clonality analysis and quantitative JAK2V617F assessment reveal a strong association between clonality and JAK2V617F in PV but not ET/MMM, and identifies a subset of JAK2V617F-negative ET and MMM patients with clonal hematopoiesis," Blood 2006, 107, 4139-4141.

Malacea et al., "Asymmetric hydrosilylation, transfer hydrogenation and hydrogenation of ketones catalyzed by iridium complexes," Coordination Chem. Rev. 2010, 254, 729-752.

Mercher et al., "JAK2T875N is a novel activating mutation that results in myeloproliferative disease with features of megakaryoblastic leukemia in a murine bone marrow transplantation model," Blood 2006, 108, 2770-2779.

Milici et al., "Cartilage preservation by inhibition of Janus kinase 3 in two rodent models of rheumatoid arthritis," Arthritis Res. Ther. 2008, 10, R14.

Moore et al., "Advances in the enzymatic reduction of ketones," Acc. Chem. Res. 2007, 40, 1412-1419.

Nicholson et al., "Differential modulation of tissue function and therapeutic potential of selective inhibitors of cyclic nucleotide phosphodiesterase isoenzymes," Trends Pharmacol. Sci. 1991, 12, 19-27.

Doucet et al., "trans-[RuCl2(phosphane)2(1,2-diamine)] and chiral trans-[RuCl2(diphosphane)(1,2-diamine)]: Shelf-stable precatalysts for the rapid, productive, and stereoselective hydrogenation of ketones," Angew. Chem. Int. Ed. 1998, 37, 1703-1707.

Noyori et al., "Asymmetric catalysis by architectural and functional molecular engineering: Practical chemo- and stereoselective hydrogenation of ketones," Angew. Chem. Int. Ed. 2001, 40, 40-73.

Ikariya et al., "Bifunctional transition metal-based molecular catalysts for asymmetric syntheses," Org. Biomol. Chem. 2006, 4, 393-406.

Olah et al., "125I-4-aminobenzyl-5'-N-methylcarboxamidoadenosine, a high affinity radioligand for the rat A3 adenosine receptor," Mol. Pharmacol. 1994, 45, 978-982.

Osswald et al., "Alcohol dehydrogenase whole-cell catalysts," Chimica Oggi Toady 2007, 25(Suppl.), 16-18.

Pardanani et al., "TG101209, a small molecule JAK2-selective kinase inhibitor potently inhibits myeloproliferative disorder-associated JAK2V617F and MPLW515L/K mutations," Leukemia 2007, 21, 1658-1668.

Pardanani, "JAK2 inhibitor therapy in myeloproliferative disorders: rationale, preclinical studies and ongoing clinical trials," Leukemia 2008, 22, 23-30.

Rane and Reddy, "Janus kinases: components of multiple signaling pathways," Oncogene 2009, 19, 5662-5679.

Salvatore et al., "Molecular cloning and characterization of the human A3 adenosine receptor," Proc. Natl. Acad. Sci. 1993, 90, 10365-10369.

Samanta et al., "Janus kinase 2: a critical target in chronic myelogenous leukemia," Cancer Res. 2006, 66, 6468-6472.

Sawyers et al., "Dominant negative MYC blocks transformation by ABL oncogenes," Cell 1992, 70, 901-910.

Schlummer and Stolle, "Scale-up of enzymatic reactions," Specialty Chemicals Magazine 2008, 28, 48-49.

Schwaller et al., "Stat5 is essential for the myelo- and lymphoproliferative disease induced by TEL/JAK2," Mol. Cell. 2000, 6, 693-704.

Scott et al., "JAK2 exon 12 mutations in polycythemia vera and idiopathic erythrocytosis," N. Eng. J. Med. 2007, 356, 459-468.

Tefferi, "JAK2 mutations in polycythemia vera—molecular mechanisms and clinical applications," N. Eng. J. Med. 2007, 356, 444-445.

Palmer et al., "Asymmetric transfer hydrogenation of C=O and C=N bonds," Tetra. Asymm. 1999, 10, 2045-2061.

Hayes et al., "A class of ruthenium(II) catalyst for asymmetric transfer hydrogenations of ketones," J. Am. Chem. Soc. 2005, 127, 7318-7319.

Zhao et al., "JAK2, complemented by a second signal from c-kit or flt-3, triggers extensive self-renewal of primary multipotential hemopoietic cells," EMBO 2002, 21, 2159-2167.

Davies and Teng, "Importance of Chirality in Drug Therapy and Pharmacy Practice: Implications for Psychiatry," Advances in Pharmacy 2003, 1, 242-252.

* cited by examiner

OPTICALLY ACTIVE PYRAZOLYLAMINOQUINAZOLINE, AND PHARMACEUTICAL COMPOSITIONS AND METHODS OF USE THEREOF

CROSS REFERENCE TO RELATED APPLICATIONS

This application claims the benefit of the priority of U.S. Provisional Application Nos. 61/379,286, filed Sep. 1, 2010, and 61/379,280, filed Sep. 1, 2010, the disclosure of each of which is incorporated herein by reference in its entirety.

FIELD

Provided herein is an optically active pyrazolylaminoquinazoline, and pharmaceutical compositions thereof. Also provided herein is a method for treating, preventing, or ameliorating one or more symptoms of a JAK-mediated condition, disorder, or disease. Further provided herein is a method for treating, preventing, or ameliorating one or more symptoms of a proliferative disease, inflammatory disease, or renal disease.

BACKGROUND

The JAK kinase family is a cytoplasmic protein kinase family comprising the members JAK1, JAK2, JAK3, and TYK2. Growth factor or cytokine receptors that recruit JAK kinases include the interferon receptors, interleukin receptors (receptors for the cytokines IL-2 to IL-7, IL-9 to IL-13, IL-15, IL-23), various hormone receptors (erythropoietin (Epo) receptor, the thrombopoietin (Tpo) receptor, the leptin receptor, the insulin receptor, the prolactin (PRL) receptor, the granulocyte colony-stimulating factor (G-CSF) receptor, the growth hormone receptor, receptor protein tyrosine kinases (such as EGFR and PDGFR), and receptors for other growth factors (leukemia inhibitory factor (LIF), oncostatin M (OSM), IFNα/β/γ, granulocyte-macrophage colony-stimulating factor (GM-CSF), ciliary neurotrophic factor (CNTF), and cardiotrophin-1 (CT-1)). See, Rane and Reddy, *Oncogene* 2000, 19, 5662-5679.

Phosphorylated receptors serve as docking sites for other SH-2 domain containing signaling molecules that interact with JAKs, such as the STAT family of transcription factors, Src family of kinases, MAP kinases, PI3 kinase, and protein tyrosine phosphatases (Rane and Reddy, *Oncogene* 2000, 19, 5662-5679). The family of latent cytoplasmic transcription factors, STATs, is the most well characterized downstream substrates for JAKs. The STAT proteins bind to phosphorylated cytokine receptors through their SH2 domains to become phosphorylated by JAKs, which leads to their dimerization, release, and eventual translocation to the nucleus where they activate gene transcription. The various members of STAT which have been identified thus far are STAT1, STAT2, STAT3, STAT4, STAT5 (including STAT5a and STAT5b), and STAT6.

Since the JAK kinases may play an important signaling role via such receptors, disorders of fat metabolism, growth disorders and disorders of the immune system are all potential therapeutic targets.

The JAK kinases and JAK2 mutations are implicated in myeloproliferative disorders, cancers, including blood borne and solid tumors. Exemplary disorders include chronic myeloid leukemia (CML), polycythemia vera (PV), essential thrombocythemia (ET), primary myelofibrosis (PMF), chronic eosinophilic leukemia (CEL), chronic myelomonocytic leukemia (CMML) and systemic mastocytosis (SM). Myeloproliferative disorders are believed to arise from either gain-of-function mutations to JAK itself or from activation by the oncoprotein BCR-ABL, which specifically activates the JAK2 pathway. Several literature reports describe role of JAK2 mutations in various disorders. See, Samanta et al., *Cancer Res.* 2006, 66, 6468-6472; Sawyers et al., *Cell* 1992, 70, 901-910; Tefferi, *N. Eng. J. Med.* 2007, 356, 444-445; Baxter et al., *Lancet* 2005, 365, 1054-1056; Jones et al., *Blood* 2005, 106, 2162-2168; Levine et al., *Blood* 2006, 107, 4139-4141; Campbell et al., *Blood* 2006, 107, 2098-2100; Scott et al., *N. Eng. J. Med.* 2007, 356, 459-468; Mercher et al., *Blood* 2006, 108, 2770-2778; Lacronique et al., *Science* 1997, 278, 1309-1312; Lacronique et al., *Blood* 2000, 95, 2535-2540; Griesinger et al., *Genes Chromosomes Cancer* 2005, 44, 329-333; Bousquet et al., *Oncogene* 2005, 24, 7248-7252; Schwaller et al., *Mol. Cell.* 2000 6, 693-704; and Zhao et al., *EMBO* 2002, 21, 2159-2167.

Literature indicates that JAK may also serve as a target for prostate cancer, including androgen-resistant prostate cancer. See, Barton et al., *Mol. Canc. Ther.* 2004, 3, 11-20, Blume-Jensen et al., *Nature* 2001, 411, 355-356; Bromberg, *J. Clin. Invest.* 2002, 109, 1139-1142; and Rane, *Oncogene* 2000, 19, 5662-5679. JAK as a prominent mediator of the cytokine signaling pathway is considered to be a therapeutic target for inflammation and transplant rejections. See, Borie et al., *Transplantation* 2005, 79, 791-801; and Milici et al., *Arthritis Research* 2008, 10, 1-9.

Given the multitude of diseases attributed to the dysregulation of JAK signaling, many small molecule inhibitors of JAK are currently being developed. Examples of compounds in preclinical development include TG101209 (TargeGen), and examples of compounds being investigated in clinical studies include INCB018424 (Incyte), XL019 (Exelixis), and TG101348 (TargeGen). See, Pardanani et al., *Leukemia* 2007, 21, 1658-1668; and Pardanai, *Leukemia* 2008, 22, 23-20.

There is, however, an existing need for a compound that is useful as a JAK kinase inhibitor for therapeutic applications.

SUMMARY OF THE DISCLOSURE

In one embodiment, provided herein is optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a pharmaceutical composition comprising optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; and a pharmaceutical carrier, excipient or diluent.

Further provided in certain embodiments herein are methods of treating, preventing, or ameliorating one or more symptoms of a proliferative disease, inflammatory disease, or renal disease in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of treating, preventing, or ameliorating one or more symptoms of a JAK-mediated condition, disorder, or disease in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of inhibiting the growth of a cell, comprising contacting the cell with optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of inhibiting the growth of a cell in a subject, comprising administering to the subject an effective amount of optically active (S)-(4-fluorophenyl)(4-((5-methyl-1H-pyrazol-3-yl)amino) quinazolin-2-yl)methanol or an isotopic variant thereof; or pharmaceutically acceptable salt, solvate, hydrate, or prodrug thereof.

In one embodiment, provided herein is a method of modulating the activity of a JAK kinase, comprising contacting the JAK kinase with optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of modulating the activity of a JAK kinase in a subject, comprising administering to the subject an effective amount of optically active (S)-(4-fluorophenyl)(4-((5-methyl-1H-pyrazol-3-yl) amino)quinazolin-2-yl)methanol or an isotopic variant thereof; or pharmaceutically acceptable salt, solvate, hydrate, or prodrug thereof.

In one embodiment, provided herein is a method of preventing, treating, or ameliorating one or more symptoms of an adenosine $A_3$ receptor-mediated condition, disorder, or disease in a subject, comprising administering the subject a therapeutically effective amount of optically active (S)-(4-fluorophenyl)(4-((5-methyl-1H-pyrazol-3-yl)amino) quinazolin-2-yl)methanol or an isotopic variant thereof; or pharmaceutically acceptable salt, solvate, hydrate, or prodrug thereof.

In one embodiment, provided herein is a method of preventing, treating, or ameliorating one or more symptoms of glaucoma or ocular hypertension in a subject, comprising administering the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of modulating the activity of an adenosine $A_3$ receptor, comprising contacting the adenosine $A_3$ receptor with an effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method of down regulating the activity of an adenosine $A_3$ receptor, comprising contacting the adenosine $A_3$ receptor with an effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In one embodiment, provided herein is a method for preparation of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof, which comprises resolving racemic (4-fluorophenyl)(4-(5-methyl-1H-pyrazol-3-ylamino)quinazolin-2-yl)methanol with chiral chromatography.

In one embodiment, provided herein is a method for preparation of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof, which comprises the step of hydrogenating (4-fluorophenyl)(4-(5-methyl-1H-pyrazol-3-ylamino)quinazolin-2-yl)methanone in the present of a chiral catalyst. In certain embodiments, the chiral catalyst is [(R)-P-Phos $RuCl_2$ (R)-DAIPEN].

DETAILED DESCRIPTION

Figure 1:
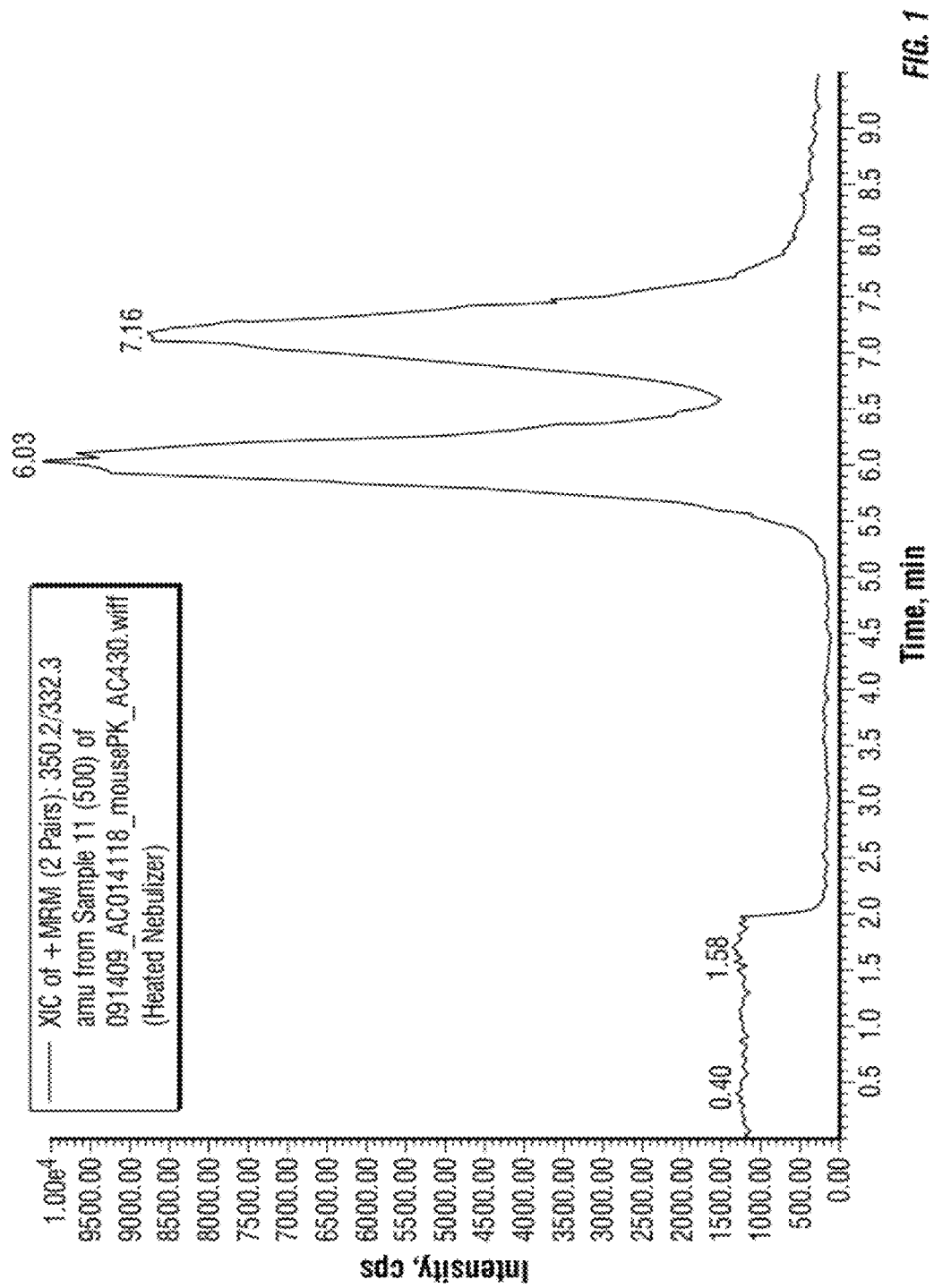
FIG. 1 depicts an LC chromatogram for the resolution of the two enantiomers of (4-fluorophenyl)(4-((5-methyl-1H-pyrazol-3-yl)amino)quinazolin-2-yl)methanol by chiral high pressure liquid chromatography on a RegisCell chiral column eluting with 85:15 hexane/isopropanol.

To facilitate understanding of the disclosure set forth herein, a number of terms are defined below.

Generally, the nomenclature used herein and the laboratory procedures in organic chemistry, medicinal chemistry, physical chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "tumor," "neoplasm," and "neoplastic disorder or disease" are used interchangeably herein and are meant to refer to unwanted cell proliferation of one or more subset of cells in a multicellular organism resulting in harm (i.e., discomfort or decreased life expectancy) to the multicellular organisms. In certain embodiments, a tumor can be benign (non-invasive) or malignant (invasive).

The term "cancer" is meant to refer to a malignant neoplasm, which is characterized by uncontrolled cell proliferation where cells have lost their normal regulatory controls that would otherwise govern the rate of cell growth. These unregulated, dividing cells can spread throughout the body and invade normal tissues in a process referred to as "metastasis."

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; and *Pharmaceutical Preformulation and Formulation*, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "solvate" refers to a complex or aggregate formed by one or more molecules of a solute, e.g., a compound provided herein, and one or more molecules of a solvent, which is present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "JAK" or "Just Another Kinase" refers to a Janus kinase or a variant thereof, including, but not limited to, Janus kinase 1 (JAK1), Janus kinase 2 (JAK2), Janus kinase 3 (JAK3), and tyrosine kinase 2 (TYK2). JAK variants include proteins substantially homologous to a native JAK, i.e., proteins having one or more naturally or non-naturally occurring amino acid deletions, insertions or substitutions (e.g., JAK derivatives, homologs and fragments), as compared to the amino acid sequence of a native JAK. The amino acid sequence of a JAK variant is at least about 80% identical, at least about 90% identical, or at least about 95% identical to a native JAK.

The terms "JAK-mediated condition, disorder or disease" and "a condition, disorder, or disease mediated by JAK" refer to a condition, disorder, or disease characterized by abnormal or dysregulated, e.g., greater than normal, JAK activity. Abnormal JAK functional activity might arise as the result of JAK overexpression in cells, expression of JAK in cells which normally do not express JAK, or dysregulation due to constitutive activation, caused, for example, by a mutation in JAK. A JAK-mediated condition, disorder, or disease may be completely or partially mediated by inappropriate JAK activity. In particular, a JAK-mediated condition, disorder, or disease is one in which modulation of a JAK activity results in some effect on the underlying condition, disorder, or disease, e.g., a JAK inhibitor results in some improvement in at least some of patients being treated.

The term "adenosine $A_3$ receptor" or "A3AR" refers to a native adenosine $A_3$ receptor or a variant thereof. A3AR variants include proteins substantially homologous to a native A3AR, i.e., proteins having one or more naturally or non-naturally occurring amino acid deletions, insertions or substitutions (e.g., A3AR derivatives, homologs and fragments), as compared to the amino acid sequence of a native A3AR. The amino acid sequence of a A3AR variant is at least about 80% identical, at least about 90% identical, or at least about 95% identical to a native A3AR.

The terms "an adenosine $A_3$-mediated condition, disorder or disease" and "a condition, disorder, or disease mediated by A3AR" refer to a condition, disorder, or disease characterized by abnormal or dysregulated, e.g., greater than normal, A3AR activity. Abnormal A3AR functional activity might arise as the result of A3AR overexpression in cells, expression of A3AR in cells which normally do not express A3AR, or dysregulation due to constitutively activation, caused, for example, by a mutation in A3AR. An A3AR-mediated condition, disorder, or disease may be completely or partially mediated by inappropriate A3AR activity. In particular, an A3AR-mediated condition, disorder, or disease is one in which modulation of A3AR activity results in some effect on the underlying condition, disorder, or disease, e.g., an A3AR antagonist results in some improvement in at least some of patients being treated.

The terms "optically active" and "enantiomerically active" refer to a collection of molecules, which has an enantiomeric excess of no less than about 10%, no less than about 20%, no less than about 30%, no less than about 40%, no less than about 50%, no less than about 60%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically active compound is no less than about 90%, no less than about 95%, no less than about 98%, or no less than about 99%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The terms "optically pure" and "enantiomerically pure" refer to a collection of molecules, which has an enantiomeric excess (ee) of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically pure compound is no less than about 90%, no less than about 95%, no less than about 98%, or no less than about 99%. An enantiomeric excess of a compound can be determined by any standard methods used by one of ordinary skill in the art, including, but not limited to, chiroptical chromatography (gas chromatography, high-performance liquid chromatography, and thin-layer chromatography) using an optically active stationary phase, isotopic dilution, electrophoresis, calorimetry, polarimetry, NMR resolution methods with chiral derivatization, and NMR methods with a chiral solvating agent or chiral shift reagent.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single stereoisomer of a compound, as determined by standard analytical methods.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C) carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-123 ($^{125}$I) iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O) oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I) In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I) and iodine-131 ($^{131}$I). It will be understood that, in a compound as provided herein, any hydrogen can be $^2$H, for example, or any carbon can be $^{13}$C, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium.

The phrase "an isotopic variant thereof; or pharmaceutically acceptable salt, solvate, hydrate, or prodrug thereof" has the same meaning as the phrase "an isotopic variant of the compound referenced therein; or a pharmaceutically acceptable salt, solvate, or prodrug of the compound referenced therein or an isotopic variant the compound referenced therein."

As used herein, the abbreviations for any protective groups, amino acids and other compounds, are, unless indicated otherwise, in accord with their common usage or recognized abbreviations including abbreviations found in *J. Org. Chem.* 2007, 72, 23A-24A or abbreviations established by the IUPAC-IUB Commission on Biochemical Nomenclature (*Biochem.* 1972, 11, 942-944).

Optically Active Pyrazolylaminoquinazoline

In one embodiment, provided herein is optically active (S)-(4-fluorophenyl)(4-(5-methyl-1H-pyrazol-3-ylamino)quinazolin-2-yl)methanol, which has the structure of Formula I:

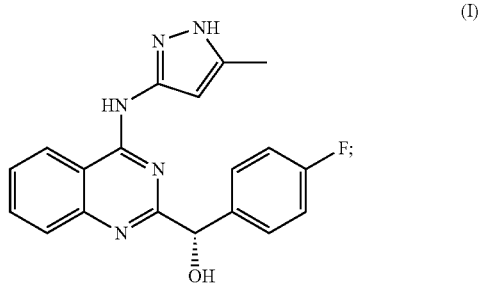 [SMILES: Cc1cc(Nc2nc([C@@H](O)c3ccc(F)cc3)nc3ccccc23)n[nH]1]

or an isotopic variant thereof; or pharmaceutically acceptable salt, solvate, hydrate, or prodrug thereof. (S)-(4-Fluorophenyl)(4-((5-methyl-1H-pyrazol-3-yl)amino)quinazolin-2-yl)methanol was determined to be the (−) isomer of (4-fluorophenyl)(4-((5-methyl-1H-pyrazol-3-yl)amino)quinazolin-2-yl)methanol by optical rotation analysis.

The corresponding racemic mixture of the compound of Formula I has been identified as a JAK kinase inhibitor. The corresponding racemic mixture of the compound of Formula I can be prepared according to U.S. application Ser. No. 12/714,323, filed on Feb. 26, 2010, now published as US 2010/0317659, the disclosure of which is incorporated by reference in its entirety.

In one embodiment, the optically active (S)-(4-fluorophenyl)(4-((5-methyl-1H-pyrazol-3-yl)amino)quinazolin-2-yl)methanol is substantially free from (R)-(4-fluorophenyl)(4-((5-methyl-1H-pyrazol-3-yl)amino)quinazolin-2-yl)methanol. In another embodiment, the optically active (S)-(4-fluorophenyl)(4-((5-methyl-1H-pyrazol-3-yl)amino)quinazolin-2-yl)methanol has an enantiomeric excess of no less than about 10%. In yet another embodiment, the optically active (S)-(4-fluorophenyl)(4-((5-methyl-1H-pyrazol-3-yl)amino)quinazolin-2-yl)methanol has an enantiomeric excess of no less than about 20%. In yet another embodiment, the optically active (S)-(4-fluorophenyl)(4-((5-methyl-1H-pyrazol-3-yl)amino)quinazolin-2-yl)methanol has an enantiomeric excess of no less than about 30%. In yet another embodiment, the optically active (S)-(4-fluorophenyl)(4-((5-methyl-1H-pyrazol-3-yl)amino)quinazolin-2-yl)methanol has an enantiomeric excess of no less than about 40%. In yet another embodiment, the optically active (S)-(4-fluorophenyl)(4-((5-methyl-1H-pyrazol-3-yl)amino)quinazolin-2-yl)methanol has an enantiomeric excess of no less than about 50%. In yet another embodiment, the optically active (S)-(4-fluorophenyl)(4-((5-methyl-1H-pyrazol-3-yl)amino)quinazolin-2-yl)methanol has an enantiomeric excess of no less than about 60%. In yet another embodiment, the optically active (S)-(4-fluorophenyl)(4-((5-methyl-1H-pyrazol-3-yl)amino)quinazolin-2-yl)methanol has an enantiomeric excess of no less than about 70%. In yet another embodiment, the optically active (S)-(4-fluorophenyl)(4-((5-methyl-1H-pyrazol-3-yl)amino)quinazolin-2-yl)methanol has an enantiomeric excess of no less than about 80%. In yet another embodiment, the optically active (S)-(4-fluorophenyl)(4-((5-methyl-1H-pyrazol-3-yl)amino)quinazolin-2-yl)methanol has an enantiomeric excess of no less than about 90%. In yet another embodiment, the optically active (S)-(4-fluorophenyl)(4-((5-methyl-1H-pyrazol-3-yl)amino)quinazolin-2-yl)methanol has an enantiomeric excess of no less than about 91%. In yet another embodiment, the optically active (S)-(4-fluorophenyl)(4-((5-methyl-1H-pyrazol-3-yl)amino)quinazolin-2-yl)methanol has an enantiomeric excess of no less than about 92%. In yet another embodiment, the optically active (S)-(4-fluorophenyl)(4-((5-methyl-1H-pyrazol-3-yl)amino)quinazolin-2-yl)methanol has an enantiomeric excess of no less than about 93%. In yet another embodiment, the optically active (S)-(4-fluorophenyl)(4-((5-methyl-1H-pyrazol-3-yl)amino)quinazolin-2-yl)methanol has an enantiomeric excess of no less than about 94%. In yet another embodiment, the optically active (S)-(4-fluorophenyl)(4-((5-methyl-1H-pyrazol-3-yl)amino)quinazolin-2-yl)methanol has an enantiomeric excess of no less than about 95%. In yet another embodiment, the optically active (S)-(4-fluorophenyl)(4-((5-methyl-1H-pyrazol-3-yl)amino)quinazolin-2-yl)methanol has an enantiomeric excess of no less than about 96%. In yet another embodiment, the optically active (S)-(4-fluorophenyl)(4-((5-methyl-1H-pyrazol-3-yl)amino)quinazolin-2-yl)methanol has an enantiomeric excess of no less than about 97%. In yet another embodiment, the optically active (S)-(4-fluorophenyl)(4-((5-methyl-1H-pyrazol-3-yl)amino)quinazolin-2-yl)methanol has an enantiomeric excess of no less than about 98%. In yet another embodiment, the optically active (S)-(4-fluorophenyl)(4-((5-methyl-1H-pyrazol-3-yl)amino)quinazolin-2-yl)methanol has an enantiomeric excess of no less than about 99%. In yet another embodiment, the optically active (S)-(4-fluorophenyl)(4-((5-methyl-1H-pyrazol-3-yl)amino)quinazolin-2-yl)methanol has an enantiomeric excess of no less than about 99.1%. In yet another embodiment, the optically active (S)-(4-fluorophenyl)(4-((5-methyl-1H-pyrazol-3-yl)amino)quinazolin-2-yl)methanol has an enantiomeric excess of no less than about 99.2%. In yet another embodiment, the optically active (S)-(4-fluorophenyl)(4-((5-methyl-1H-pyrazol-3-yl)amino)quinazolin-2-yl)methanol has an enantiomeric excess of no less than about 99.3%. In yet another embodiment, the optically active (S)-(4-fluorophenyl)(4-((5-methyl-1H-pyrazol-3-yl)amino)quinazolin-2-yl)methanol has an enantiomeric excess of no less than about 99.4%. In yet another embodiment, the optically active (S)-(4-fluorophenyl)(4-((5-methyl-1H-pyrazol-3-yl)amino)quinazolin-2-yl)methanol has an enantiomeric excess of no less than about 99.5%. In yet another embodiment, the optically active (S)-(4-fluorophenyl)(4-((5-methyl-1H-pyrazol-3-yl)amino)quinazolin-2-yl)methanol has an enantiomeric excess of no less than about 99.6%. In yet another embodiment, the optically active (S)-(4-fluorophenyl)(4-((5-methyl-1H-pyrazol-3-yl)amino)quinazolin-2-yl)methanol has an enantiomeric excess of no less than about 99.7%. In yet another embodiment, the optically active (S)-(4-fluorophenyl)(4-((5-methyl-1H-pyrazol-3-yl)amino)quinazolin-2-yl)methanol has an enantiomeric excess of no less than about 99.8%. In still another embodiment, the optically active (S)-(4-fluorophenyl)(4-((5-methyl- 1H-pyrazol-3-yl)amino)quinazolin-2-yl)methanol has an enantiomeric excess of no less than about 99.9%.

In one embodiment, the optically active (S)-(4-fluorophenyl)(4-((5-methyl-1H-pyrazol-3-yl)amino)quinazolin-2-yl)methanol has a specific rotation of no less than about 0.5, no less than about 1, no less than about 1.5, no less than about 2, no less than about 2.5, no less than about 3, no less than about 3.5, no less than about 4, no less than about 4.5, or no less than about 5. In another embodiment, the optically active (S)-(4-fluorophenyl)(4-((5-methyl-1H-pyrazol-3-yl)amino)quinazolin-2-yl)methanol has a specific rotation of no less than about 0.5. In yet another embodiment, the optically active (S)-(4-fluorophenyl)(4-((5-methyl-1H-pyrazol-3-yl)amino)quinazolin-2-yl)methanol has a specific rotation of no less than about 1. In yet another embodiment, the optically active (S)-(4-fluorophenyl)(4-((5-methyl-1H-pyrazol-3-yl)amino)quinazolin-2-yl)methanol has a specific rotation of no less than about 1.5. In yet another embodiment, the optically active (S)-(4-fluorophenyl)(4-((5-methyl-1H-pyrazol-3-yl)amino)quinazolin-2-yl)methanol has a specific rotation of no less than about 2. In yet another embodiment, the optically active (S)-(4-fluorophenyl)(4-((5-methyl-1H-pyrazol-3-yl)amino)quinazolin-2-yl)methanol has a specific rotation of no less than about 2.5. In yet another embodiment, the optically active (S)-(4-fluorophenyl)(4-((5-methyl-1H-pyrazol-3-yl)amino)quinazolin-2-yl)methanol has a specific rotation of no less than about 3. In yet another embodiment, the optically active (S)-(4-fluorophenyl)(4-((5-methyl-1H-pyrazol-3-yl)amino)quinazolin-2-yl)methanol has a specific rotation of no less than about 3.5. In yet another embodiment, the optically active (S)-(4-fluorophenyl)(4-((5-methyl-1H-pyrazol-3-yl)amino)quinazolin-2-yl)methanol has a specific rotation of no less than about 4. In yet another embodiment, the optically active (S)-(4-fluorophenyl)(4-((5-methyl-1H-pyrazol-3-yl)amino)quinazolin-2-yl)methanol has a specific rotation of no less than about 4.5. In yet another embodiment, the optically active (S)-(4-fluorophenyl)(4-((5-methyl-1H-pyrazol-3-yl)amino)quinazolin-2-yl)methanol has a specific rotation of no less than about 5. In certain embodiments, the specific rotation of the compound of Formula I is determined according to Method 781 in USP XXXI (2003). In certain embodiments, the specific rotation of the compound of Formula I is determined according to Method 781 in USP XXXI (2003) in methanol. In certain embodiments, the specific rotation of the compound of Formula I is determined according to Method 781 in USP XXXI (2003) at a temperature of about 22° C.

In certain embodiments, the optically active (S)-(4-fluorophenyl)(4-((5-methyl-1H-pyrazol-3-yl)amino)quinazolin-2-yl)methanol contains no less than about 80% by weight the (S)-isomer and no greater than about 20% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 90% by weight the (S)-isomer and no greater than about 10% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 91% by weight the (S)-isomer and no greater than about 9% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 92% by weight the (S)-isomer and no greater than about 8% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 93% by weight the (S)-isomer and no greater than about 7% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 94% by weight the (S)-isomer and no greater than about 6% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 95% by weight the (S)-isomer and no greater than about 5% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 96% by weight the (S)-isomer and no greater than about 4% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 97% by weight the (S)-isomer and no greater than about 3% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 98% by weight the (S)-isomer and no greater than about 2% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 99% by weight the (S)-isomer and no greater than about 1% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 99.5% by weight the (S)-isomer and no greater than about 0.5% by weight (R)-isomer of (4-fluorophenyl)(4-((5-methyl-1H-pyrazol-3-yl)amino)quinazolin-2-yl)methanol. In certain embodiments, the optically active (S)-(4-fluorophenyl)(4-((5-methyl-1H-pyrazol-3-yl)amino)quinazolin-2-yl)methanol contains no less than about 99.9% by weight the (S)-isomer and no greater than about 0.1% by weight (R)-isomer of (4-fluorophenyl)(4-((5-methyl-1H-pyrazol-3-yl)amino)quinazolin-2-yl)methanol.

In certain embodiments, the optically active (S)-(4-fluorophenyl)(4-((5-methyl-1H-pyrazol-3-yl)amino)quinazolin-2-yl)methanol is substantially pure. In certain embodiments, the optically active (S)-(4-fluorophenyl)(4-((5-methyl-1H-pyrazol-3-yl)amino)quinazolin-2-yl)methanol has a purity of at least about 50%, at least about 70%, at least about 80%, at least about 90%, at least about 95%, at least about 98%, at least about 99%, or at least about 99.5% by weight. In certain embodiments, the optically active (S)-(4-fluorophenyl)(4-((5-methyl-1H-pyrazol-3-yl)amino)quinazolin-2-yl)methanol has a purity of at least about 50% by weight. In certain embodiments, the optically active (S)-(4-fluorophenyl)(4-((5-methyl-1H-pyrazol-3-yl)amino)quinazolin-2-yl)methanol has a purity of at least about 70% by weight. In certain embodiments, the optically active (S)-(4-fluorophenyl)(4-((5-methyl-1H-pyrazol-3-yl)amino)quinazolin-2-yl)methanol has a purity of at least about 80% by weight. In certain embodiments, the optically active (S)-(4-fluorophenyl)(4-((5-methyl-1H-pyrazol-3-yl)amino)quinazolin-2-yl)methanol has a purity of at least about 90% by weight. In certain embodiments, the optically active (S)-(4-fluorophenyl)(4-((5-methyl-1H-pyrazol-3-yl)amino)quinazolin-2-yl)methanol has a purity of at least about 95% by weight. In certain embodiments, the optically active (S)-(4-fluorophenyl)(4-((5-methyl-1H-pyrazol-3-yl)amino)quinazolin-2-yl)methanol has a purity of at least about 98% by weight. In certain embodiments, the optically active (S)-(4-fluorophenyl)(4-((5-methyl-1H-pyrazol-3-yl)amino)quinazolin-2-yl)methanol has a purity of at least about 99% by weight. In certain embodiments, the optically active (S)-(4-fluorophenyl)(4-((5-methyl-1H-pyrazol-3-yl)amino)quinazolin-2-yl)methanol has a purity of at least about 99.5% by weight.

In one embodiment, the compound of Formula I is a modulator of a JAK kinase. In certain embodiments, the compound of Formula I is a modulator of a JAK1 kinase. In certain embodiments, the compound of Formula I is a modulator of a JAK2 kinase. In certain embodiments, the compound of Formula I is a modulator of a JAK3 kinase. In certain embodiments, the compound of Formula I is a modulator of a TYK2 kinase.

In certain embodiments, the compound of Formula I is a modulator selective for a JAK2 kinase. In certain embodiments, the compound of Formula I is a modulator selective for a JAK2 kinase over a JAK3 kinase. In certain embodiments, the compound of Formula I binds to a JAK3 kinase at a dissociation constant ($K_d$) of at least about 2-fold, at least about 3-fold, about 5-fold, about 10-fold, about 20-fold, about 25-fold, about 50-fold, about 75-fold, or about 100-fold higher than to a JAK2 kinase. In certain embodiments, the compound of Formula I is a modulator selective for a JAK2 kinase over a JAK1 kinase. In certain embodiments, the compound of Formula I binds to a JAK1 kinase at a dissociation constant ($K_d$) of at least about 2-fold, at least about 3-fold, about 5-fold, about 10-fold, about 20-fold, about 25-fold, or about 50-fold higher than to a JAK2 kinase. In certain embodiments, the compound of Formula I is a modulator selective for a JAK2 kinase over a TYK2 kinase. In certain embodiments, the compound of Formula I binds to a TYK2 kinase at a dissociation constant ($K_d$) of at least about 2-fold, at least about 3-fold, about 5-fold, about 10-fold, about 20-fold, about 25-fold, or about 50-fold higher than to a JAK2 kinase.

In another embodiment, the compound of Formula I is an inhibitor of a JAK kinase. In certain embodiments, the compound of Formula I is an inhibitor of a JAK1 kinase. In certain embodiments, the compound of Formula I is an inhibitor of a JAK2 kinase. In certain embodiments, the compound of Formula I is an inhibitor of a JAK3 kinase. In certain embodiments, the compound of Formula I is an inhibitor of a TYK2 kinase.

In certain embodiments, the compound of Formula I is an inhibitor selective for a JAK2 kinase. In certain embodiments, the compound of Formula I is an inhibitor selective for a JAK2 kinase over a JAK3 kinase. In certain embodiments, the compound of Formula I inhibits a JAK3 kinase at an inhibitory constant ($K_i$) of at least about 2-fold, at least about 3-fold, about 5-fold, about 10-fold, about 20-fold, about 25-fold, about 50-fold, about 75-fold, or about 100-fold higher than a JAK2 kinase. In certain embodiments, the compound of Formula I is an inhibitor selective for a JAK2 kinase over a JAK1 kinase. In certain embodiments, the compound of Formula I inhibits a JAK1 kinase at an inhibitory constant ($K_i$) of at least about 2-fold, at least about 3-fold, about 5-fold, about 10-fold, about 20-fold, about 25-fold, or about 50-fold higher than to a JAK2 kinase. In certain embodiments, the compound of Formula I is an inhibitor selective for a JAK2 kinase over a TYK2 kinase. In certain embodiments, the compound of Formula I inhibits a TYK2 kinase at an inhibitory constant ($K_i$) of at least about 2-fold, at least about 3-fold, about 5-fold, about 10-fold, about 20-fold, about 25-fold, or about 50-fold higher than to a JAK2 kinase.

In one embodiment, provided herein is optically active (S)-(4-fluorophenyl)(4-(5-methyl-1H-pyrazol-3-ylamino)quinazolin-2-yl)methanol.

In another embodiment, provided herein is an optically active isotopic variant of (S)-(4-fluorophenyl)(4-(5-methyl-1H-pyrazol-3-ylamino)quinazolin-2-yl)methanol, or pharmaceutically acceptable salt, solvate, hydrate, or prodrug thereof. In certain embodiments, provided herein is an optically active deuterated (S)-(4-fluorophenyl)(4-(5-methyl-1H-pyrazol-3-ylamino)quinazolin-2-yl)methanol, or pharmaceutically acceptable salt, solvate, hydrate, or prodrug thereof. Isotopic enrichment (for example, deuteration) of therapeutic agents to improve pharmacokinetics ("PK"), pharmacodynamics ("PD"), and/or toxicity profiles has been demonstrated previously with some classes of drugs. See, for example, Lijinsky et. al., *Food Cosmet. Toxicol.*, 1982, 20, 393; Lijinsky et. al., *J. Nat. Cancer Inst.* 1982, 69, 1127; Mangold et. al., *Mutation Res.* 1994, 308, 33; Gordon et. al., *Drug Metab. Dispos.* 1987, 15, 589; Zello et. al., *Metabolism* 1994, 43, 487; Gately et. al., *J. Nucl. Med.* 1986, 27, 388; and Wade, *Chem. Biol. Interact.* 1999, 117, 191. Isotopic enrichment of a drug can be used, for example, (1) to reduce or eliminate undesirable metabolites, (2) to increase the half-life of the parent drug, (3) to decrease the number of doses needed to achieve a desired effect, (4) to decrease the amount of a dose necessary to achieve a desired effect, (5) to increase the formation of active metabolites, if any are formed, and/or (6) to decrease the production of deleterious metabolites in specific tissues and/or to create a more effective drug and/or a safer drug for combination therapy, whether the combination therapy is intentional or not.

In yet another embodiment, provided herein is a pharmaceutically acceptable salt of optically active (S)-(4-fluorophenyl)(4-(5-methyl-1H-pyrazol-3-ylamino)quinazolin-2-yl)methanol, or pharmaceutically acceptable solvate or hydrate thereof.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the pharmaceutically acceptable salt of optically active (S)-(4-fluorophenyl)(4-(5-methyl-1H- pyrazol-3-ylamino)quinazolin-2-yl)methanol is a hydrochloride salt, or pharmaceutically acceptable solvate or hydrate thereof. In another embodiment, the pharmaceutically acceptable salt of optically active (S)-(4-fluorophenyl)(4-(5-methyl-1H-pyrazol-3-ylamino)quinazolin-2-yl)methanol is a hydrobromide salt, or pharmaceutically acceptable solvate or hydrate thereof. In yet another embodiment, the pharmaceutically acceptable salt of optically active (S)-(4-fluorophenyl)(4-(5-methyl-1H-pyrazol-3-ylamino)quinazolin-2-yl)methanol is a camphor sulfonic acid salt, or pharmaceutically acceptable solvate or hydrate thereof. In yet another embodiment, the pharmaceutically acceptable salt of optically active (S)-(4-fluorophenyl)(4-(5-methyl-1H-pyrazol-3-ylamino)quinazolin-2-yl)methanol is an R-camphor sulfonic acid salt, or pharmaceutically acceptable solvate or hydrate thereof. In yet another embodiment, the pharmaceutically acceptable salt of optically active (S)-(4-fluorophenyl)(4-(5-methyl-1H-pyrazol-3-ylamino)quinazolin-2-yl) methanol is an S-camphor sulfonic acid salt, or pharmaceutically acceptable solvate or hydrate thereof.

In yet another embodiment, provided herein is a pharmaceutically acceptable solvate of optically active (S)-(4-fluorophenyl)(4-(5-methyl-1H-pyrazol-3-ylamino)quinazolin-2-yl)methanol.

In yet another embodiment, provided herein is a hydrate of optically active (S)-(4-fluorophenyl)(4-(5-methyl-1H-pyrazol-3-ylamino)quinazolin-2-yl)methanol.

In still another embodiment, provided herein is a pharmaceutically acceptable prodrug of optically active (S)-(4-fluorophenyl)(4-(5-methyl-1H-pyrazol-3-ylamino)quinazolin-2-yl)methanol. A prodrug is a functional derivative of a parent compound, e.g., the compound of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs*, 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J. Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *Chem Med Chem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

In certain embodiments, without being bound by any theory, optically active (S)-(4-fluorophenyl)(4-(5-methyl-1H-pyrazol-3-ylamino)quinazolin-2-yl)methanol or an isotopic variant thereof; or pharmaceutically acceptable salt, solvate, hydrate, or prodrug thereof is a prodrug. In certain embodiments, without being bound by any theory, optically active (S)-(4-fluorophenyl)(4-(5-methyl-1H-pyrazol-3-ylamino)quinazolin-2-yl)methanol is converted into the corresponding (R)-isomer in a subject. In certain embodiments, the subject is a mammal. In certain embodiments, the mammal is a human.

The compound provided herein is intended to encompass all possible structural isomers, unless a particular structural isomer is specified. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

Methods of Synthesis

The compound of Formula I provided herein can be prepared, isolated, or obtained by any method known to one of skill in the art, including, but not limited to, synthesis from a suitable optically pure precursor, asymmetric synthesis from an achiral starting material, or resolution of a racemic or enantiomeric mixture, for example, chiral chromatography, recrystallization, resolution, diastereomeric salt formation, or derivatization into diastereomeric adducts followed by separation.

In one embodiment, provided herein is a method for preparation of the compound of Formula I, which comprises resolving racemic (4-fluorophenyl)(4-(5-methyl-1H-pyrazol-3-ylamino)quinazolin-2-yl)methanol with chiral chromatography. In certain embodiments, as shown in Scheme I, the two individual enantiomers are separated using a chiral column, wherein the stationary phase is silica gel coated with a chiral selector such as tris-(3,5-dimethylphenyl)carbamoyl cellulose.

In another embodiment, provided herein is a method for preparation of the compound of Formula I, comprising the step of reducing achiral ketone 1 with hydrogen in the present of a chiral catalyst. As shown in Scheme II, ketone 1 is reduced to predominantly a single enantiomeric product with a chiral reducing system of "type A" or "type B," wherein type A and type B differ from each other solely by having chiral auxiliaries of opposite chiralities. In certain embodiments, the chiral catalyst is [(R)-P-Phos RuCl$_2$ (R)-DAIPEN].

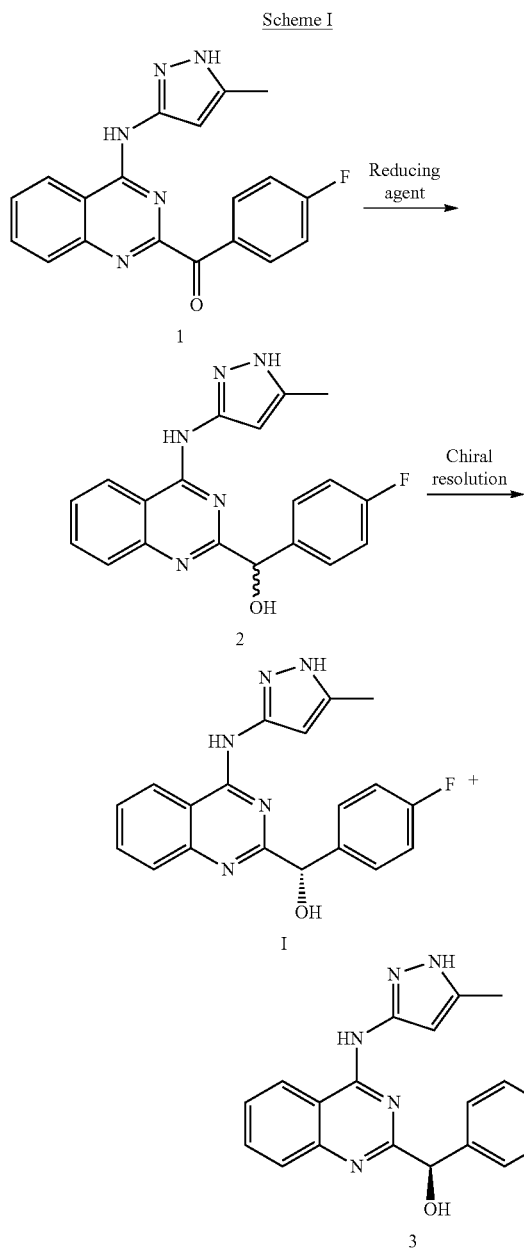

In certain embodiments, the reduction of achiral ketone 1 in presence of a chiral catalyst is carried out in isopropyl alcohol as a solvent. In certain embodiments, the reduction of achiral ketone 1 in presence of a chiral catalyst is carried out in isopropyl alcohol and water mixture as a solvent. In certain embodiments, isopropyl alcohol and water are used in a ratio of 1:1, 8:1 or 9:1. In one embodiment, DMSO is used as a cosolvent in the reaction. In one embodiment, DMSO is used in 10, 20 or 30% based on the total amount of isopropyl alcohol and water mixture. In certain embodiments, isopropyl alcohol, DMSO and water are used in a ratio of 1:1:1, 4:4:0.5, 8:1:1, 47:47:6, 41:58:1, 44:50:6, or 18:79:3. In certain embodiments, isopropyl alcohol, DMSO and water are used in a ratio of 41:58:1. In certain embodiments, isopropyl alcohol, and DMSO are used in a ratio of 1:1. In certain embodiments, the reduction is carried out in presence of a base, such as potassium hydroxide, potassium tert butoxide and others. In certain embodiments, the base is used in 2-15 Mol %, in one embodiment, 2 Mol %, 5 Mol %, 10 Mol %, 12.5 Mol % or 15 Mol %. In certain embodiments, the reduction is carried out at a temperature of 40-80° C., in one embodiment, 40° C., 50° C., 60° C., 70° C. or 80° C. In certain embodiments, the reduction is carried out at a temperature of 70° C. In certain embodiments, the reduction is carried out at a pressure of 4 bar to 30 bar, in one embodiment, 4, 5, 10, 15, 20, 25 or 30 bar. In certain embodiments, the reduction is carried out at a pressure of 4 bar. In certain embodiments, the catalyst loading in the reaction is 100/1, 250/1, 500/1, 1000/1, 2000/1, 3000/1, 4000/1, 5000/1, 7000/1, 10,0000/1 or 20,000/1. In certain embodiments, the catalyst loading in the reaction is 2000/1 or 4000/1.

In yet another embodiment, provided herein is a method for preparation of the compound of Formula I, which comprises the step of reducing achiral ketone 1 with a ketoreductase (e.g., alcohol dehydrogenase). See, Moore et al., *Acc. Chem. Res.* 2007, 40, 1412-1419; Daussmann et al., *Engineering in Life Sciences* 2006, 6, 125-129; Schlummer and Stolle, *Specialty Chemicals Magazine* 2008, 28, 48-49; Osswald et al., *Chimica Oggi* 2007, 25(Suppl.), 16-18; and Kambourakis and Rozzell, *Pharma Chem* 2006, 5(9), 2-5.

In yet another embodiment, provided herein is a method for preparation of the compound of Formula I, comprising the step of reducing achiral ketone 1 with a reducing reagent (e.g., borane or borohydride reagents) in the presence of a chiral catalyst. In certain embodiments, the reducing agent is borane or a borohydride reagent. In certain embodiments, the chiral catalyst is a chiral oxazaborolidine. See, Cory et al., *Tetrahedron Letters* 1996, 37, 5675; and Cho, *Chem. Soc. Rev.* 2009, 38, 443.

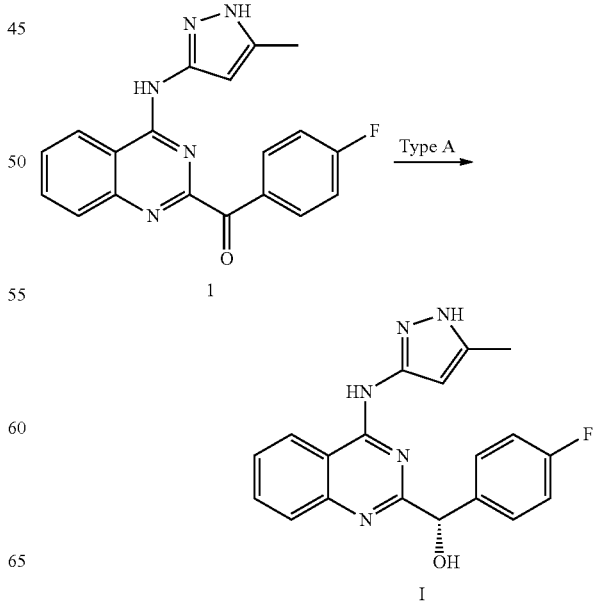

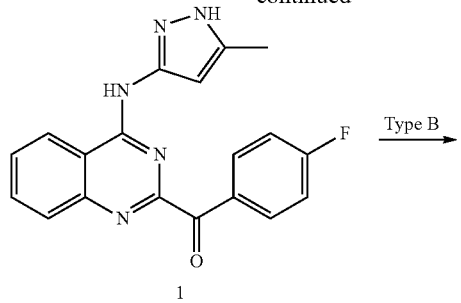

In yet another embodiment, provided herein is a method for preparation of the compound of Formula I, comprising the step of reducing achiral ketone 1 via asymmetric hydrosilylation. See, U.S. Appl. Pub. No. 2008/0269490, the disclosure of which is incorporated herein by reference in its entirety.

In still another embodiment, provided herein is a method for preparation of the compound of Formula I, comprising the step of reducing achiral ketone 1 via transfer hydrogenation catalyzed by an iridium complex. See, Malacea et al., *Coordination Chemistry Reviews* 2010, 254, 729-752.

The starting materials used in the synthesis of the compound of Formula I provided herein are either commercially available or can be prepared by a method known to one of skill in the art. For example, ketone 1 can be prepared according to the methods described in U.S. application Ser. No. 12/714,323, filed on Feb. 26, 2010, the disclosure of which is incorporated herein by reference in its entirety.

Pharmaceutical Compositions

In one embodiment, provided herein is a pharmaceutical composition comprising optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; and a pharmaceutically acceptable vehicle, carrier, diluent, or excipient, or a mixture thereof.

In another embodiment, provided herein is a pharmaceutical composition comprising optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; and PEG 400 and water. In certain embodiments, the weight ratio of PEG 400 versus water is 3:1. In certain embodiments, the pharmaceutical composition is for intravenous administration.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The optically active compound of Formula I provided herein may be administered alone, or in combination with one or more other compounds provided herein. The pharmaceutical compositions that comprise the active compound of Formula I provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; and one or more pharmaceutically acceptable vehicles, carriers, diluents, or excipients.

In another embodiment, the pharmaceutical compositions are provided in a dosage form for parenteral administration, which comprise optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; and one or more pharmaceutically acceptable vehicles, carriers, diluents, or excipients.

In yet another embodiment, the pharmaceutical compositions are provided in a dosage form for topical administration, which comprise optically active (S)-(4-fluorophenyl)(4-((5-methyl-1H-pyrazol-3-yl)amino)quinazolin-2-yl)methanol or an isotopic variant thereof or pharmaceutically acceptable salt, solvate, hydrate, or prodrug thereof and one or more pharmaceutically acceptable vehicles, carriers, diluents, or excipients. In certain embodiments, the topical administration is nasal, respiratory, or pulmonary administration.

The pharmaceutical compositions provided herein can be provided in a unit-dosage form or multiple-dosage form. A unit-dosage form, as used herein, refers to physically a discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage forms. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, the pharmaceutical compositions provided herein each contain from about 0.1 mg to about 2,000 mg, from about 10 mg to about 1,000 mg, from about 20 mg to about 500 mg, or from about 25 mg to about 250 mg of the optically active compound of Formula I provided herein. In certain embodiments, the pharmaceutical dosage unit forms provided herein contain from about 1 mg to about 2,000 mg, from about 10 mg to about 1,000 mg, from about 20 mg to about 500 mg, or from about 25 mg to about 250 mg of the optically active compound of Formula I provided herein per dosage unit form. In certain embodiments, the pharmaceutical dosage unit forms contain about 10 mg, about 20 mg, about 25 mg, about 50 mg, about 100 mg, about 250 mg, about 500 mg, about 1,000 mg, or about 2,000 mg of the optically active compound of Formula I provided herein.

In certain embodiments, the pharmaceutical compositions provided herein are co-formulated with one or more other active ingredients, which do not impair the desired therapeutic action, or with substances that supplement the desired action.

A. Oral Administration

The pharmaceutical compositions provided herein for oral administration can be provided in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained-, pulsed-, controlled-, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, pulmonary, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology,* 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology,* supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol. 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein is a method of treating, preventing, or ameliorating one or more symptoms of a proliferative disease, inflammatory disease, or renal disease in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In another embodiment, provided herein is a method of treating, preventing, or ameliorating a proliferative disease, inflammatory disease, or renal disease in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In certain embodiments, the proliferative disease is a myeloproliferative disorder, including, but not limited to, polycythemia vera (PCV), essential thrombocythemia (ET), primary myelofibrosis (PMF), chronic eosinophilic leukemia (CEL), chronic myelomonocytic leukemia (CMML), systemic mastocytosis (SM), and idiopathic myelofibrosis (IMF). In certain embodiments, the proliferative disease is leukemia, including, but not limited to, myeloid leukemia, chronic myeloid leukemia (CML), imatinib-resistant CMLs, acute myeloid leukemia (AML), and acute megakaryoblastic leukemia (AMKL). In certain embodiments, the proliferative disease is a lymphoproliferative disease, including, but not limited to, myeloma. In certain embodiments, the proliferative disease is cancer, including, but not limited to, head and neck cancer, prostate cancer, breast cancer, ovarian cancer, melanoma, lung cancer, brain tumor, pancreatic cancer, and renal carcinoma. In certain embodiments, the inflammatory disease or disorder, includes, but is not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), and dry eye syndrome (or keratoconjunctivitis sicca (KCS)). In certain embodiments, renal disease is diabetic neuropathy.

In yet another embodiment, provided herein is a method of treating, preventing, or ameliorating one or more symptoms of a JAK-mediated condition, disorder, or disease, in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof.

In another embodiment, provided herein is a method of treating, preventing, or ameliorating a JAK-mediated condition, disorder, or disease, in a subject, comprising administering to the subject a therapeutically effective amount of optically active (S)-(4-fluorophenyl)(4-((5-methyl-1H-pyrazol-3-yl)amino)quinazolin-2-yl)methanol or an isotopic variant thereof or pharmaceutically acceptable salt, solvate, hydrate, or prodrug thereof.

In certain embodiments, the JAK-mediated condition, disorder, or disease is a myeloproliferative disorder, including, but not limited to, polycythemia vera (PCV), essential thrombocythemia (ET), primary myelofibrosis (PMF), chronic eosinophilic leukemia (CEL), chronic myelomonocytic leukemia (CMML), systemic mastocytosis (SM), and idiopathic myelofibrosis (IMF). In certain embodiments, the JAK-mediated condition, disorder, or disease is leukemia, including, but not limited to, myeloid leukemia, chronic myeloid leukemia (CML), imatinib-resistant CMLs, acute myeloid leukemia (AML), and acute megakaryoblastic leukemia (AMKL). In certain embodiments, the JAK-mediated condition, disorder, or disease is a lymphoproliferative disease, including, but not limited to, myeloma. In certain embodiments, the JAK-mediated condition, disorder, or disease is cancer, including, but not limited to, head and neck cancer, prostate cancer, breast cancer, ovarian cancer, melanoma, lung cancer, brain tumor, pancreatic cancer, and renal carcinoma. In certain embodiments, the JAK-mediated condition, disorder, or disease is a inflammatory disease or disorder, including, but not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), and dry eye syndrome (or keratoconjunctivitis sicca (KCS)).

In certain embodiments, the proliferative disease or the JAK-mediated condition, disorder, or disease is selected from myeloproliferative disorders, including, but not limited to, polycythemia vera (PCV), essential thrombocythemia, idiopathic myelofibrosis (IMF), and hypereosinophilic syndrome (HES); leukemia, including, but not limited to, myeloid leukemia, chronic myeloid leukemia (CML), imatinib-resistant CMLs, acute myeloid leukemia (AML), acute lymphoblastic leukemia (ALL), and acute megakaryoblastic leukemia (AMKL); lymphoproliferative diseases, including, but not limited to, myeloma; cancer, including, but not limited to, head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, and melanoma. In certain embodiments, the inflammatory disease or the JAK-mediated condition, disorder, or disease is selected from, but not limited to diseases relating to immune dysfunction, immunodeficiency or immunomodulation, including but not limited to tissue transplant rejection, graft-versus-host disease, wound healing, kidney disease, diabetic neuropathy, autoimmune diseases, multiple sclerosis, thyroiditis, type 1 diabetes, sarcoidosis, psoriasis, allergic rhinitis, atopic dermatitis, myasthenia gravis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), conjunctivitis, dry eye syndrome (or keratoconjunctivitis sicca (KCS)), uveitis, iritis, scleritis, rhinitis, sinusitis, bronchitis, myocarditis, ischemia reperfusion injuries, systemic inflammatory response syndrome (SIRS), and sepsis. In certain embodiments, the renal disease or the JAK-mediated condition, disorder, or disease includes diabetic neuropathy.

In certain embodiments, JAK-mediated diseases and disorders include, but are not limited to, restenosis, fibrosis, and scleroderma. In certain embodiments, JAK-mediated diseases include, but are not limited to, viral diseases such as Epstein Barr virus (EBV), hepatitis (hepatitis B or hepatitis C), human immunodeficiency virus (HIV), human T-lymphotropic virus type 1 (HTLV-1), varicella-zoster virus, and the human papilloma virus (HPV).

In certain embodiments, the compound of Formula I provided herein is administered to the subject in the amount ranging from about 0.01 to about 1,000 mg/kg, from about 0.1 to about 500 mg/kg, from about 0.1 to about 250 mg/kg, or from about 0.1 to about 100 mg/kg.

In certain embodiments, the compound of Formula I provided herein is administered to the subject in the amount ranging from about 0.01 to about 1,000 mg/kg/day, from about 0.1 to about 500 mg/kg/day, from about 0.1 to about 250 mg/kg/day, or from about 0.1 to about 100 mg/kg/day. In certain embodiments, the compound of Formula I provided herein is administered to the subject in the amount of about 1, about 2, about 3, about 4, about 5, about 6, about 7, about 8, about 9, about 10, about 15, about 20, about 25, about 30, about 35, about 40 about 50, about 60, about 70, about 75, about 80, about 90, about 100, about 105, about 120, about 130, about 140, about 150, about 160, about 170, about 180, about 190, about 200, about 300, about 400, about 500, about 600, about 700, about 750, about 800, about 900, or about 1,000 mg/kg/day.

The administered dose of the compound of Formula I provided herein can also be expressed in units other than the unit "mg/kg/day." For example, doses for parenteral administration can be expressed as mg/m$^2$/day. One of ordinary skill in the art would readily know how to convert doses from mg/kg/day to mg/m$^2$/day to given either the height or weight of a subject or both (See, www.fda.gov/cder/cancer/animalframe.htm). For example, a dose of 1 mg/kg/day for a 65 kg human is approximately equal to 38 mg/m$^2$/day.

Depending on the disease to be treated and the subject's condition, the compound of Formula I provided herein can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound of Formula I provided herein may be formulated, alone or together, in suitable dosage unit with pharmaceutically acceptable excipients, carriers, adjuvants and vehicles, appropriate for each route of administration.

The compound of Formula I provided herein can be delivered as a single dose such as, e.g., a single bolus injection, or oral tablets or pills; or over time such as, e.g., continuous infusion over time or divided bolus doses over time.

The compound of Formula I provided herein can be administered once daily (QD), or divided into multiple daily doses such as twice daily (BID), three times daily (TID), and four times daily (QID). In addition, the administration can be continuous, i.e., every day, or intermittently. The term "intermittent" or "intermittently" as used herein is intended to mean stopping and starting at either regular or irregular intervals. For example, intermittent administration of the compound of Formula I provided herein is administration for one to six days per week, administration in cycles (e.g., daily administration for two to eight consecutive weeks, then a rest period with no administration for up to one week), or administration on alternate days.

In certain embodiments, the frequency of administration of the compound of Formula I provided herein is in the range of about a daily dose to about a monthly dose. In certain embodiments, the administration of the compound of Formula I provided herein is once a day, twice a day, three times a day, four times a day, once every other day, twice a week, once every week, once every two weeks, once every three weeks, or once every four weeks. In one embodiment, the compound of Formula I provided herein is administered once a day. In another embodiment, the compound of Formula I provided herein is administered twice a day. In yet another embodiment, the compound of Formula I provided herein is administered three times a day. In still another embodiment, the compound of Formula I provided herein is administered four times a day.

In certain embodiments, the subject is a mammal. In certain embodiments, the mammal is a human.

In one embodiment, the proliferative disease is a tumor. In another embodiment, the proliferative disease is a solid tumor. In certain embodiments, the solid tumor is an advanced solid tumor. In certain embodiments, the solid tumor is a metastatic solid tumor. In yet another embodiment, the proliferative disease is cancer. In yet another embodiment, the proliferative disease is advanced cancer. In certain embodiments, the solid tumor is metastatic cancer.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In certain embodiments, the cancer that is treatable with the methods provided herein includes, but is not limited to, bladder cancer, breast cancer, cervical cancer, colon cancer (e.g., colorectal cancer), endometrial cancer, esophageal cancer, gastric cancer, glioma (e.g., glioblastoma), head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer.

In certain embodiments, the cancer that is treatable with the methods provided herein includes, but is not limited to, bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, and prostate cancer.

In certain embodiments, the cancer is head and neck cancer. In certain embodiments, the cancer is lung cancer. In certain embodiments, the cancer is lung adenocarcinoma. In certain embodiments, the cancer is esophogeal or upper GI cancer.

In certain embodiments, the subject to be treated with one of the methods provided herein has not been treated with anticancer therapy. In certain embodiments, the subject to be treated with one of the methods provided herein has been treated with anticancer therapy.

The methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis.

In certain embodiments, in each method provided herein, the compound of Formula I is combined or used in combination with a second therapeutic agent. As used herein, the term "in combination" includes the use of more than one therapy (e.g., one or more prophylactic and/or therapeutic agents).

However, the use of the term "in combination" does not restrict the order in which therapies (e.g., prophylactic and/or therapeutic agents) are administered to a subject with a condition, disorder, or disease. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of the compound of Formula I provided herein and another therapy (e.g., a prophylactic or therapeutic agent) which has been or is currently being used to prevent, treat, or manage a condition, disorder, or disease, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a condition, disorder, or disease. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, treatment, or management of a condition, disorder, or disease). In addition, a synergistic effect can result in improved efficacy of agents in the prevention, treatment, or management of a condition, disorder, or disease. Finally, a synergistic effect of a combination of therapies (e.g., a combination of prophylactic or therapeutic agents) may avoid or reduce adverse or unwanted side effects associated with the use of either therapy alone.

The compound of Formula I provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the second therapeutic agent is a chemotherapeutic agent, anti-proliferative agent, anti-inflammatory agent, immunomodulatory agent, or immunosuppressive agent. In one embodiment, the second therapeutic agent is an anticancer agent. In one embodiment, the anticancer agent is an antimetabolite, including, but not limited to, cytarabine (also known as cytosine arabinoside or Ara-C), fludarabine, 5-fluorouracil, gemcitabine, HDAC (high dose cytarabine), 6-mercaptopurine, methotrexate, and pemetrexed. In another embodiment, the anticancer agent is an antimicrotubule agent, including, but not limited to, vinca alkaloids (e.g., vinblastine, vincristine, and vinorelbine) and taxanes (e.g., paclitaxel, albumin-bound paclitaxel (ABRAXANE®), and docetaxel). In yet another embodiment, the anticancer agent is an alkylating agent, including, but not limited to, busulfan, carmustine, chlorambucil, cyclophosphamide, fludarabine, ifosfamide, mechlorethamine, melphalan, and nitrosoureas (e.g., bischloroethylnitrosurea, hydroxyurea, carmustine, and lomustine). In yet another embodiment, the anticancer agent is a platinum agent, including, but not limited to, carboplatin, CI-973, cisplatin, oxaliplatin, and satraplatin (JM-216). In yet another embodiment, the anticancer agent is an anthracycline, including, but not limited to, adriamycin, daunorubicin, and doxrubicin. In yet another embodiment, the anticancer agent is an antitumor antibiotic, including, but not limited to, adriamycin, bleomycin, daunomycin (also known as daunorubicin), doxorubicin, idarubicin, and mitomycin. In yet another embodiment, the anticancer agent is a topoisomerase inhibitor, including, but not limited to, camptothecins, etoposide, irinotecan, and topotecan. In yet another embodiment, the anticancer agent is a kinase inhibitor, including, but not limited to, erlotinib and imatinib. In yet another embodiment, the anticancer agent is a nucleoside, including, but not limited to, gemcitabine. In yet another embodiment, the anticancer agent is an anti-angiogenesis agent, including, but not limited to, SUTENT®, sorafenib, and bevacizumab. In yet another embodiment, the anticancer agent is a cytotoxic agent, including, but not limited to, estramustine phosphate and prednimustine. In yet another embodiment, the anticancer agent is hormones or hormone agonists, antagonists, partial agonists or partial antagonists. In yet another embodiment, the anticancer agent is selected from the group consisting of enzymes (asparaginase), hormones (tamoxifen, leuprolide, flutamide, and megestrol), hydroxyurea, interferons, and oblimersen. In still another embodiment, the anticancer agent is a monoclonal antibody, including, but not limited to bevacizumab and cetuximab. For a more comprehensive discussion of updated cancer therapies; See, http://www.nci.nih.gov/, a list of the FDA approved oncology drugs at http://wwwfda.gov/cder/cancer/druglistframe.htm, and The Merck Manual, Seventeenth Ed. 1999, the entire contents of which are hereby incorporated by reference.

In another embodiment, the second therapeutic agent is an anti-inflammatory agent, including, but not limited to, methotrexate, matrix metalloproteinase inhibitors, inhibitors of pro-inflammatory cytokines (e.g., anti-TNF molecules, TNF soluble receptors, and IL1), non-steroidal anti-inflammatory drugs (NSAIDs), prostaglandin synthase inhibitors (e.g., choline magnesium salicylate and salicylsalicyclic acid), COX-1 and/or COX-2 inhibitors, and glucocorticoid receptor agonists (e.g., corticosteroids, methylprednisone, prednisone, and cortisone).

The route of administration of the compound of Formula I provided herein is independent of the route of administration of a second therapy. In one embodiment, the compound of Formula I provided herein is administered orally. In another embodiment, the compound of Formula I provided herein is administered intravenously. Thus, in accordance with these embodiments, the compound of Formula I provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, pulmonarily, vaginally, intraoccularly, via local delivery by catheter or stent, subcutaneously, intraadiposally, intraarticularly, intrathecally, or in a slow release dosage form. In one embodiment, the compound of Formula I provided herein and a second therapy are administered by the same mode of administration, orally or by IV. In another embodiment, the compound of Formula I provided herein is administered by one mode of administration, e.g., orally, whereas the second agent (an anticancer agent) is administered by another mode of administration, e.g., by IV.

The compound or composition provided herein, or pharmaceutically acceptable salts, solvates or hydrates thereof, may be administered simultaneously with, prior to, or after administration of one or more of the above agents.

Other therapies or anticancer agents that may be used in combination with the compound provided herein include surgery, radiotherapy, endocrine therapy, biologic response modifiers (e.g., interferons, interleukins, and tumor necrosis factor (TNF)), hyperthermia and cryotherapy, and agents to attenuate any adverse effects (e.g., antiemetics).

In yet another embodiment, provided herein is a method of inhibiting the growth of a cell, comprising contacting the cell with an effective amount of optically active (S)-(4-fluorophenyl)(4-((5-methyl-1H-pyrazol-3-yl)amino)quinazolin-2-yl)methanol or an isotopic variant thereof or pharmaceutically acceptable salt, solvate, hydrate, or prodrug thereof.

In yet another embodiment, provided herein is a method of inhibiting the growth of a cell in a subject, comprising administering to the subject an effective amount of optically active (S)-(4-fluorophenyl)(4-((5-methyl-1H-pyrazol-3-yl)amino)quinazolin-2-yl)methanol or an isotopic variant thereof or pharmaceutically acceptable salt, solvate, hydrate, or prodrug thereof.

In certain embodiments, the cell is a mammalian cell. In certain embodiments, the mammal is a human cell. In certain embodiments, the cell is a tumor cell. In certain embodiments, the cell is mammalian tumor cell. In certain embodiments, the cell is a human tumor cell. In certain embodiments, the cell is a cancerous cell. In certain embodiments, the cell is mammalian cancerous cell. In certain embodiments, the cell is a human cancerous cell.

In certain embodiments, the cancerous cell that can be treated with the methods provided herein includes, but is not limited to, cells of bladder cancer, breast cancer, cervical cancer, colon cancer (e.g., colorectal cancer), endometrial cancer, esophageal cancer, gastric cancer, glioma (e.g., glioblastoma), head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer.

In certain embodiments, the cell is a cell of bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, or prostate cancer.

The inhibition of cell growth can be gauged by, e.g., counting the number of cells contacted with a compound of interest, comparing the cell proliferation with otherwise identical cells not contacted with the compound, or determining the size of the tumor that encompasses the cells. The number of cells, as well as the size of the cells, can be readily assessed using any method known in the art (e.g., trypan blue exclusion and cell counting, measuring incorporation of $^3$H-thymidine into nascent DNA in a cell).

In yet another embodiment, provided herein is a method of modulating the activity of a JAK kinase, comprising contacting the JAK kinase with optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof. In certain embodiments, provided herein is a method of inhibiting the activity of a JAK kinase, comprising contacting the JAK kinase with optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof. In certain embodiments, the JAK kinase is constitutively activated. In certain embodiments, the JAK kinase is mutated.

In yet another embodiment, provided herein is a method of modulating the activity of a JAK kinase in a subject, comprising administering to the subject an effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof. In certain embodiments, provided herein is a method of inhibiting the activity of a JAK kinase in a subject, comprising administering to the subject an effective amount of optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof. In certain embodiments, the JAK kinase is constitutively activated. In certain embodiments, the JAK kinase is mutated.

In one embodiment, provided herein is a method of preventing, treating, or ameliorating one or more symptoms of an adenosine $A_3$-mediated condition, disorder, or disease in a subject, comprising administering the subject a therapeutically effective amount of optically active (S)-(4-fluorophenyl)(4-((5-methyl-1H-pyrazol-3-yl)amino)quinazolin-2-yl)methanol or an isotopic variant thereof or pharmaceutically acceptable salt, solvate, hydrate, or prodrug thereof.

In certain embodiments, the adenosine $A_3$-mediated conditions, disorders, or diseases include, but are not limited to, myeloproliferative disorders such as polycythemia vera (PCV), essential thrombocythemia and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain tumor, pancreatic cancer and renal carcinoma; and inflammatory diseases or disorders related to immune dysfunction, immunodeficiency, immunomodulation, autoimmune diseases, tissue transplant rejection, graft-versus-host disease, wound healing, kidney disease including diabetic neuropathy, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD) and dry eye syndrome (or keratoconjunctivitis sicca (KCS)).

In certain embodiments, provided herein are methods of using the disclosed compounds and compositions, or pharmaceutically acceptable salts, solvates or hydrates thereof, for the treatment, prevention, or amelioration of a disease or disorder selected from myeloproliferative disorders such as polycythemia vera (PCV), essential thrombocythemia and idiopathic myelofibrosis (IMF) and hypereosinophilic syndrome (HES); leukemia such as myeloid leukemia including chronic myeloid leukemia (CML), imatinib-resistant forms of CML, acute myeloid leukemia (AML), acute lymphoblastic leukemia (ALL) and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, melanoma; and inflammatory diseases or disorders related to immune dysfunction, immunodeficiency or immunomodulation, such as tissue transplant rejection, graft-versus-host disease, wound healing, kidney disease; autoimmune diseases such as multiple sclerosis, thyroiditis, type 1 diabetes, sarcoidosis, psoriasis, allergic rhinitis, atopic dermatitis, myasthenia gravis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), inflammatory diseases of the eye including conjunctivitis, uveitis, iritis, scleritis, inflammatory diseases of the respiratory tract including the upper respiratory tract such as rhinitis and sinusitis and inflammatory diseases of the lower repiratory tract including bronchitis; inflammatory myopathy such as myocarditis, other inflammatory diseases such as ischemia reperfusion injuries related to an inflammatory ischemic event such as a stroke or cardiac arrest, and other inflammatory conditions such as systemic inflammatory response syndrome (SIRS) and sepsis.

In certain embodiments, adenosine $A_3$-mediated diseases and disorders include restenosis, fibrosis and scleroderma. In certain embodiments, adenosine $A_3$-mediated diseases include viral diseases such as Epstein Barr virus (EBV), hepatitis (hepatitis B or hepatitis C), human immunodeficiency virus (HIV), Human T-lymphotropic virus type 1 (HTLV-1), varicella-zoster virus and the human papilloma virus (HPV).

In certain embodiments, the adenosine $A_3$-mediated condition, disorder, or disease is a cardiovascular disease, including, but not limited to, ischaemic heart disease. In certain embodiments, the adenosine $A_3$-mediated condition, disorder, or disease is lung injury. In certain embodiments, the adenosine $A_3$-mediated condition, disorder, or disease is renal failure. In certain embodiments, the adenosine $A_3$-mediated condition, disorder, or disease is an eye disease, including, but not limited to, glaucoma and ocular hypertension. In certain embodiments, the adenosine $A_3$-mediated condition, disorder, or disease is glaucoma or ocular hypertension.

The compound of Formula I provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes containers and dosage forms of the compound of Formula I provided herein.

In certain embodiments, the kit includes a container comprising dosage forms of the compound of Formula I provided herein, in one or more containers.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

Evaluation of Biological Activity

Standard physiological, pharmacological, and biochemical procedures are available for determining biological activity of the compound of Formula I against JAK kinases, including wild type and mutant JAK kinases. Such assays include, for example, biochemical assays such as binding assays (see, Fabian et al., *Nature Biotechnology* 2005, 23,329-336), radioactivity incorporation assays, as well as a variety of cell based assays.

Exemplary cell based assays include measurement of STAT5 phosphorylation, for example, by ELISA; or the measurement of proliferation in leukemic cell lines such as TF-1 or HEL-2, for example, by BrdU incorporation, by fluorescent staining, or by a reporter assay activated by the transcription factor STAT5. Cells useful in the assays include cells with wildtype JAK such as TF-1 or mutated JAK such as the cell line HEL-2 which express a constitutively active JAK2 carrying the V617F mutation. Suitable cells include those derived through cell culture from patient samples as well as cells derived using routine molecular biology techniques, e.g., retroviral transduction, transfection, mutagenesis, etc.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. See also, *J. Org. Chem.* 2007, 72(1), 23A-24A. Specifically, but without limitation, the following abbreviations may be used in the examples and throughout the specification: g (grams); mg (milligrams); mL (milliliters); µL (microliters); L (liter); mM (millimolar); µM (micromolar); Hz (Hertz); MHz (megahertz); mmol (millimoles); eq. (equivalent); hr or hrs (hours); min (minutes); psi (pounds per square inch); MS (mass spectrometry); NMR (nuclear magnetic resonance); ESI (electrospray ionization); EI (electron ionization); HPLC (high-performance liquid chromatography or high pressure liquid chromatography); ACN (acetonitrile); $CDCl_3$ (deuterated chloroform); DCM (dichloromethane); DMF (N,N-dimethylformamide); DMSO (dimethylsulfoxide); DMSO-$d_6$ (deuterated dimethylsulfoxide); EtOAc (ethyl acetate); $Et_2O$ (diethyl ether); EtOH (ethanol); MeOH (methanol); iPrOH or IPA (isopropanol); tBuOH (tert-butanol); PE (petroleum ether); THF (tetrahydrofuran); DIPEA (N,N-diisopropylethylamine);

TEA (triethylamine); HOAc (acetic acid); TFA (trifluoroacetic acid); Me (methyl); Et (ethyl); iPr (isopropyl); tBu (tert-butyl); Boc (tert-butoxylcarbony); Bn (benzyl); Ph (phenyl); DAIPEN (1,1-bis(4-methoxyphenyl)-3-methyl-1,2-butanediamine); P-Phos (2,2',6,6'-tetramethoxy-4,4'-bis(di(3,5-xylyl)phosphino)-3,3'-bipyridine); and FBS (fetal bovine serum).

Generally, proton nuclear magnetic resonance ($^1$HNMR) spectra were recorded on a Bruker Avance 300 MHz NMR spectrometer. Chemical shifts are reported as parts per million (δ) downfield relative to tetramethylsilane. Unless otherwise indicated, low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Chiral HPLC analyses were carried out using a Phenomenex Lux Cellulose-2 column eluted with 7:3 hexane/EtOH, unless otherwise specified.

In the examples below, enantiomer (1) refers to (S)-(4-fluorophenyl)(4-((5-methyl-1H-pyrazol-3-yl)amino)quinazolin-2-yl)methanol and enantiomer (2) refers to (R)-(4-fluorophenyl)(4-((5-methyl-1H-pyrazol-3-yl)amino)quinazolin-2-yl)methanol.

In certain examples below, the synthetic procedures described for preparation of one enantiomer of 4-fluorophenyl)(4-((5-methyl-1H-pyrazol-3-yl)amino)quinazolin-2-yl)methanol can be modified for the preparation of the other enantiomer by replacing the chiral catalyst. For example, procedure for preparation of (R)-(4-fluorophenyl)(4-((5-methyl-1H-pyrazol-3-yl)amino)quinazolin-2-yl)methanol using [(S)-P-Phos RuCl$_2$ (S)-DAIPEN] catalyst can be similarly used for preparing (S)-(4-fluorophenyl)(4-((5-methyl-1H-pyrazol-3-yl)amino)quinazolin-2-yl)methanol using [(R)-P-Phos RuCl$_2$ (R)-DAIPEN] catalyst.

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Example 1

Separation of the Enantiomers of 4-fluorophenyl)(4-((5-methyl-1H-pyrazol-3-yl)amino)quinazolin-2-yl)methanol The two enantiomers of racemic 4-fluorophenyl)(4-((5-methyl-1H-pyrazol-3-yl)amino)quinazolin-2-yl)methanol were separated by chiral LC using a REGISCELL1™ column (25 cm×4.6 mm 5 micron) (Regis Technologies, Inc., Morton Grove, Ill.). The concentration of the racemic sample was 500 ng/mL. The separation was carried out isocratically with hexane/isopropanol (85:15) at a flow rate of 1.75 mL/min and at ambient temperature over 9.5 min by monitoring the 350/332 Da parent mass/fragment mass transition.

As shown in FIG. 1, the S-enantiomer (the first eluting peak) had a retention time of 6.03 minutes with a peak area of 49.8%, and the R-enantiomer (the second eluting peak) had a retention time of 7.16 minutes with a peak area of 50.2%.

Example 2

Preparation of (S)-(4-fluorophenyl)(4-((5-methyl-1H-pyrazol-3-yl)amino)quinazolin-2-yl)methanol

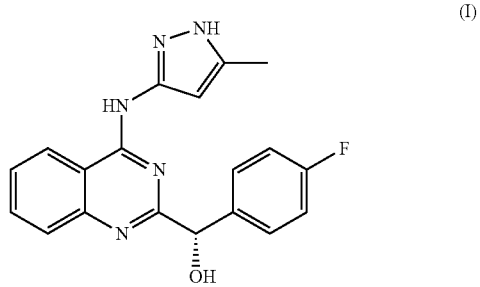 [SMILES: Cc1cc(Nc2nc([C@@H](O)c3ccc(F)cc3)nc3ccccc23)n[nH]1]

(I)

The compound of Formula I was prepared as shown in Scheme 1.

Step A. Preparation of (4-chloroquinazoline-2-yl)(4-fluorophenyl)methanone 12. To a solution of ethyl 4-chloroquinazoline-2-carboxylate 11 (0.6 g, 2.53 mmol) in THF (6 mL) at −40° C. was added dropwise a solution of 4-fluorophenylmagnesium bromide in THF (1 M, 3 mL, 3.0 mmol, 1.2 eq). The reaction mixture was stirred at −40° C. for 4 hrs. The reaction was quenched by addition of 0.5 N HCl (5 mL) and the mixture was extracted with EtOAc (2×10 mL). The combined organic layers were washed with brine, dried over MgSO$_4$, and concentrated. The crude product was purified by silica gel chromatography eluting with EtOAc/hexanes to afford compound 12 as a light yellow solid (440 mg, 60%). $^1$H NMR (300 MHz, DMSO-d$_6$) δ 7.45-7.40 (m, 2H), 8.07-8.03 (m, 1H), 8.17-8.13 (m, 2H), 8.23 (m, 2H), 8.42 (d, 1H); LC-MS (ESI) m/z: 287 (M+H)$^+$.

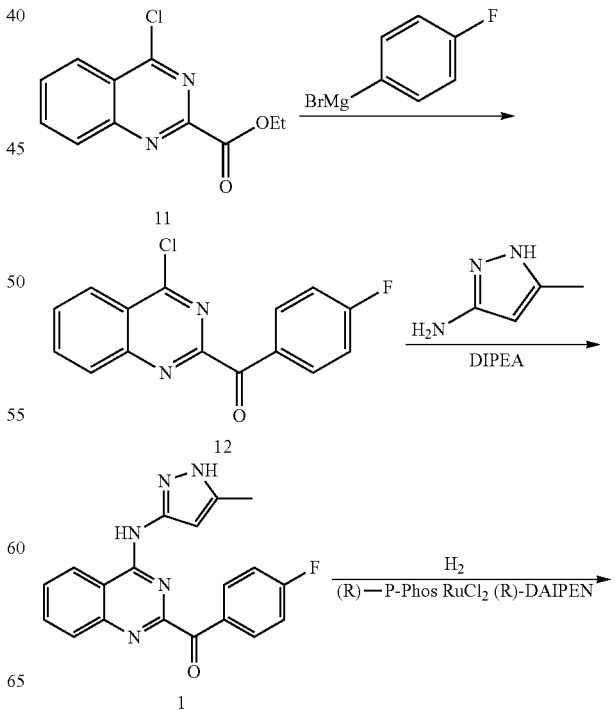

Scheme 1

-continued

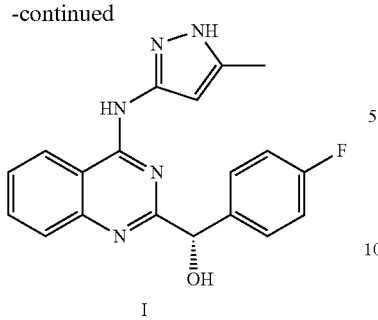

I

Step B. Preparation of (4-fluorophenyl)(4-(5-methyl-1H-pyrazol-3-ylamino)quinazolin-2-yl)methanone 1. To a solution of compound 12 (84 mg, 0.30 mmol) in DMF (3 mL) at room temperature were added DIPEA (0.103 mL, 0.6 mmol) and 5-methyl-1H-pyrazol-3-amine (88 mg, 0.9 mmol). The reaction mixture was heated at 40° C. overnight. Water was added, and the yellow precipitate was collected by filtration and washed with water. The solid was purified by silica gel chromatography eluting with DCM/MeOH to give compound 1 (30 mg, 29%). $^1$H NMR (300 MHz, DMSO-$d_6$) δ 2.19 (s, 3H), 6.54 (s, 1H), 7.40 (m, 2H), 7.68 (t, 1H), 7.9-7.7 (m, 2H), 8.08 (m, 2H), 8.74 (d, 1H), 10.66 (s, 1H), 12.20 (s, 1H); LC-MS (ESI) m/z: 348 (M+H)$^+$.

Step C. Preparation of (S)-(4-fluorophenyl)(4-((5-methyl-1H-pyrazol-3-yl)amino)quinazolin-2-yl)methanol (I). A stirred mixture of compound 1 (418 mg, 1.2 mmol) and (R)-P-Phos RuCl$_2$ (R)-DAIPEN (5.4 mg, 0.0048 mmol) at room temperature was subjected to five cycles pressurizing with nitrogen to 40 psi and then depressurizing. Then KOtBu/tBuOH (1 M, 14.4 μL, 0.0144 mmol) in 9:1 i-PrOH/H$_2$O (4 mL) was added and the mixture was subjected to five cycles of pressurizing with nitrogen to 40 psi and then depressurizing. The stirred mixture was then subjected to ten cycles of pressurizing with hydrogen to 435 psi and then depressurizing. The mixture was then stirred at 900 rpm under hydrogen (435 psi) at 50° C. for 18 hrs. The mixture was allowed to cool to room temperature and vented carefully. MeOH (8 mL) was added, and a sample (0.2 mL) was analyzed by chiral HPLC and LCMS (Phenomenex Luna C18) eluted with a gradient of CH$_3$CN in 0.1% aq. HOAc. The above procedure was carried out in analogous fashion in an additional 12 runs. Samples of the required specification (>98%, >95% enantiomeric excess) were combined and filtered through celite, washing with MeOH. The filtrate was concentrated to dryness and further dried under high vacuum overnight to afford compound I as an off-white solid (4.48 g, 12.8 mmol). $^1$H NMR (300 MHz, DMSO-$d_6$) δ 12.13 (br s, 1H), 10.38 (br s, 1H), 8.59 (d, J=7.7 Hz, 1H), 7.70-7.98 (m, 2H), 7.45-7.64 (m, 3H), 7.06-7.24 (m, 2H), 6.45 (s, 1H), 5.80 (s, 1H), 5.67 (s, 1H), 2.26 (s, 3H); LC-MS (ESI) m/z: 350 (M+H)$^+$. Analysis by chiral HPLC showed a 96.7% enantiomeric excess of the earlier eluting enantiomer.

Optical activity of the compound of Formula I was determined using a sample prepared using this procedure in a large scale, following Method 781 in USP XXXI (2003) using a Perkin Elmer 241 polarimeter. The sample was found to have a specific optical rotation ($[α]_D^{22}$) of about +4.976 (c=6.029 mg/mL, methanol).

Example 3

Preparation of (S)-(4-fluorophenyl)(4-((5-methyl-1H-pyrazol-3-yl)amino)quinazolin-2-yl)methanol hydrochloride To a suspension of (S)-(4-fluorophenyl)(4-((5-methyl-1H-pyrazol-3-yl)amino)quinazolin-2-yl)methanol (4.33 g) in 1:1 CH$_3$CN/H$_2$O (100 mL) was added 1N HCl (15.5 mL, 15.5 mmol). The solution was frozen and lyophilized to afford 4.9 g of (S)-(4-fluorophenyl)(4-((5-methyl-1H-pyrazol-3-yl)amino)quinazolin-2-yl)methanol hydrochloride as a solid. $^1$H NMR (300 MHz, DMSO-$d_6$) δ 14.61 (br s., 1H), 12.16 (br s., 1H), 8.84 (d, J=8.1 Hz, 1H), 8.24 (d, J=8.1 Hz, 1H), 8.02-8.13 (m, 1H), 7.73-7.88 (m, 1H), 7.55-7.70 (m, 2H), 7.18-7.36 (m, 2H), 6.21 (s, 1H), 6.02 (s, 1H), 3.93 (br s, 2H, obscured by H$_2$O peak), 2.26 (s, 3H); LC-MS (ESI) m/z: 350 (M+H)$^+$. Analysis by chiral HPLC showed that the HCl salt had an enantiomeric excess of about 100%.

Example 4

Scale up of the Synthesis of (S)-(4-fluorophenyl)(4-((5-methyl-1H-pyrazol-3-yl)amino)quinazolin-2-yl)methanol I A stirred mixture of (4-fluorophenyl)(4-(5-methyl-4H-pyrazol-3-ylamino)quinazolin-2-yl)methanone (16.66 g, 48 mmol) and [(R)-P-Phos RuCl$_2$ (R)-DAIPEN] (217 mg, 0.192 mmol) at room temperature was subjected to five cycles of pressurizing with nitrogen to 40 psi followed by depressurization. Then 1M KOtBu/tBuOH (576 μL, 0.0.576 mmol) in 9:1 i-PrOH/H$_2$O (4 mL) was added and the mixture was subjected to five cycles of pressurizing with nitrogen to 40 psi followed by depressurization. The stirred mixture was then subjected to ten cycles of pressurizing with hydrogen to 435 psi followed by depressurization. The mixture was then stirred at 900 rpm under hydrogen (435 psi) at 40° C. for 18 hrs. The mixture was allowed to cool to room temperature and then carefully vented. The resulting precipitate was collected by filtration and washed with cold MeOH (100 mL) to afford (S)-(4-fluorophenyl)(4-((5-methyl-1H-pyrazol-3-yl)amino)quinazolin-2-yl)methanol as a white solid (13.8 g). Chiral HPLC indicated a >99% enantiomeric excess of the earlier eluting enantiomer.

A repeat run of the above procedure on a 96 mmol scale afforded 30.5 g of (S)-(4-fluorophenyl)(4-((5-methyl-1H-pyrazol-3-yl)amino)quinazolin-2-yl)methanol as a white solid, for which chiral HPLC indicated a >99% enantiomeric excess of the earlier eluting enantiomer.

Example 5

Preparation of (R)-(4-fluorophenyl)(4-((5-methyl-1H-pyrazol-3-yl)amino)quinazolin-2-yl)methanol R-(−)-camphorsulfonic acid salt (R)-(4-Fluorophenyl)(4-((5-methyl-1H-pyrazol-3-yl)amino)quinazolin-2-yl)methanol was synthesized according to the procedure as described for (S)-(4-fluorophenyl)(4-((5-methyl-1H-pyrazol-3-yl)amino)quinazolin-2-yl)methanol, except using [(S)-P-Phos RuCl$_2$ (S)-DAIPEN] in place of [(R)-P-Phos RuCl$_2$ (R)-DAIPEN] during ketone reduction. Optical activity of (R)-(4-fluorophenyl)(4-((5-methyl-1H-pyrazol-3-yl)amino)quinazolin-2-yl)methanol was determined, following Method 781 in USP XXXI (2003), using a Perkin Elmer 241 polarimeter. The (R)-isomer was found to have a specific optical rotation ($[\alpha]_D^{22}$) of about −4.688 (c=6.079 mg/mL, methanol).

To (R)-(4-fluorophenyl)(4-((5-methyl-1H-pyrazol-3-yl)amino)quinazolin-2-yl)methanol (100 mg, 0.29 mmol) in EtOH (10 mL) was added a solution of R-(−)-camphorsulfonic acid (67 mg, 0.29 mmol) in EtOH (10 mL). The homogeneous solution was diluted with EtOAc (ca. 50 mL) and concentrated to a viscous residue. To the residue in EtOAc (ca. 5 mL) was added diethyl ether until the solution was cloudy, and the mixture was allowed to stand at room temperature with occasional scraping and agitation. After 24 hrs, a yellow solid had formed. The mixture was cooled on ice and the solid was collected by filtration, washing with cold diethyl ether, to afford (R)-(4-fluorophenyl)(4-((5-methyl-1H-pyrazol-3-yl)amino)quinazolin-2-yl)methanol R-(−)-camphorsulfonic acid salt as a yellow solid (133 mg, 80%). $^1$H NMR (300 MHz, DMSO-$d_6$) δ 14.35 (br s, 1H), 12.59 (br s, 1H), 12.08 (br s, 1H), 8.78 (d, J=8.1 Hz, 1H), 8.20 (d, J=8.3 Hz, 1H), 7.99-8.13 (m, 1H), 7.79 (t, J=7.6 Hz, 1H), 7.51-7.68 (m, 2H), 7.18-7.35 (m, 2H), 6.17 (s, 1H), 5.99 (s, 1H), 2.86 (d, J=14.7 Hz, 1H), 2.60-2.77 (m, 1H), 2.36 (d, J=14.7 Hz, 1H), 2.17-2.29 (m, 1H), 2.25 (s, 3H), 1.89-1.96 (m, 1H), 1.78-1.89 (m, 2H), 1.76 (s, 1H), 1.22-1.32 (m, 2H), 1.05 (s, 3H), 0.74 (s, 3H).

Figure 2:
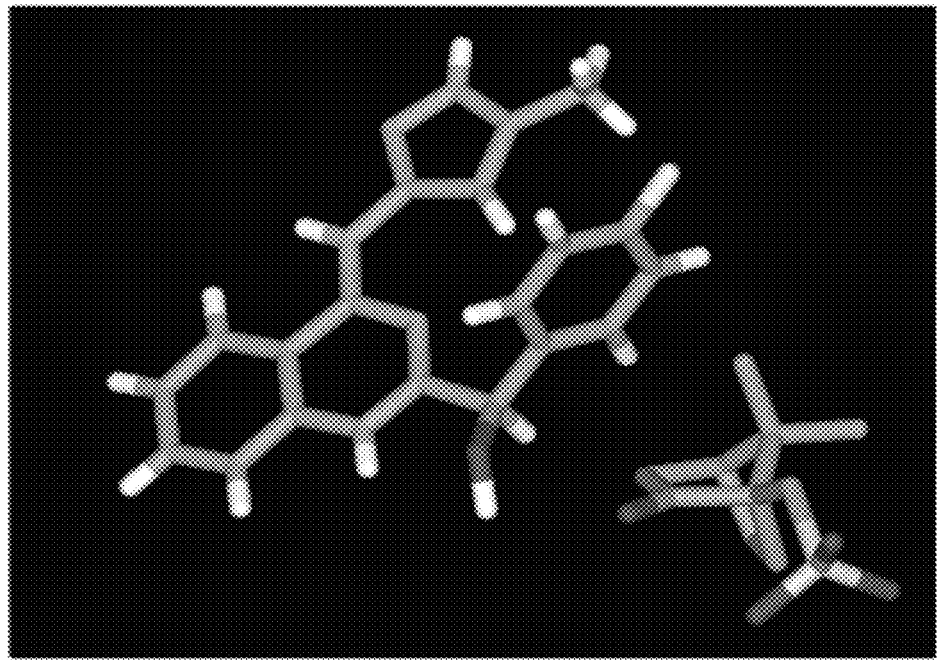
FIG. 2 depicts the X-ray crystal structure of optically active (R)-4-fluorophenyl)(4-((5-methyl-1H-pyrazol-3-yl)amino) quinazolin-2-yl)methanol (R)-(−)-camphor sulfonic acid salt.
Figure 3:
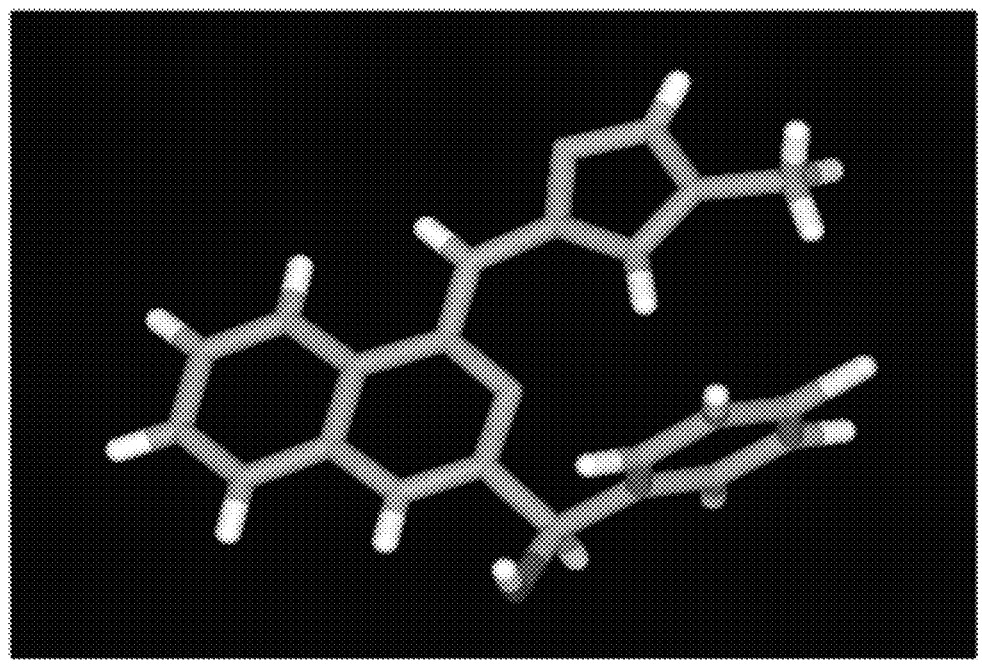
FIG. 3 depicts the X-ray crystal structure of optically active (R)-4-fluorophenyl)(4-((5-methyl-1H-pyrazol-3-yl)amino) quinazolin-2-yl)methanol.

The resulting salt was analyzed by single crystal X-ray and the absolute configuration of (4-fluorophenyl)(4-((5-methyl-1H-pyrazol-3-yl)amino)quinazolin-2-yl)methanol was determined to be R (FIG. 2).

Example 6

X-Ray Crystal Structure Analysis of the R Enantiomer

Chiral reduction of (4-fluorophenyl)(4-(5-methyl-4H-pyrazol-3-ylamino)quinazolin-2-yl)methanone was carried out in the presence of [(S)-P-Phos RuCl$_2$ (S)-DAIPEN], according to Example 5. The solid product (4.58 g, 13 mmol) was dissolved in 1:1 CH$_3$CN/H$_2$O (100 mL) and treated with 1N HCl (16 mL, 16 mmol). The solution was frozen and lyophilized to afford a solid hydrochloride salt. Chiral HPLC analysis of the hydrochloride salt (RegisCell column eluted with 85:15 hexane/isopropanol) indicated a 2:98 ratio of earlier eluting enantiomer to the later eluting enantiomer. A sample of the hydrochloride salt was crystallized from a mixture of isopropanol, ethanol, and aq. HCl to afford yellow crystals. X-ray crystallographic analysis of a yellow crystal showed the structure of protonated (R)-(4-fluorophenyl)(4-((5-methyl-1H-pyrazol-3-yl)amino)quinazolin-2-yl)methanol. Chiral HPLC analysis of a separate sample of yellow crystals (RegisCell column eluted with 85:15 hexane/i-propanol) indicated a 4:96 ratio of earlier eluting enantiomer to the later eluting enantiomer. The preponderance of evidence supports the conclusion that the later eluting isomer has (R) absolute configuration.

Example 7

Competition Binding Assay to Determine Binding Constants ($K_D$) of a JAK Kinase Inhibitor Competition binding assays used herein were developed, validated, and performed as described in Fabian et al., *Nature Biotechnology* 2005, 23,329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17× PBS, 0.05% Tween 20, 6 mM DTT). Test compounds were prepared as 100× stocks in DMSO and rapidly diluted into the aqueous environment. DMSO was added to control assays lacking a test compound. Primary screen interactions were performed in polypropylene 384-well plates in a final volume of 34 µL, while $K_d$ determinations were performed in polystyrene 96-well plates in a final volume of 135 µL. The assay plates were incubated at room temperature with shaking for 1 hr, long enough for binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 2 µM non-biotinylated affinity ligand) and incubated at room temperature with shaking for 30 min. The kinase concentration in the eluates was measured by quantitative PCR. Each kinase was tested individually against each compound. $K_d$s were determined using eleven serial threefold dilutions. A selectivity score, which is a quantitative measure of selectivity of a compound against a panel of enzymes, may be calculated for a compound by dividing the number of enzymes for which a compound meets a set criteria, (for example, a binding constant of 100 nM or less), by the total number of enzymes tested. A kinase selectivity score, S10, for example, is calculated for each compound by dividing the number of kinases for which a compound at a certain concentration (for example, 10 µM) displayed inhibition of 90% or greater compared to negative control lacking inhibitors (DMSO only), divided by the number of distinct kinases tested excluding mutant variants, typically 359 or 386 kinases.

The $K_d$ values for racemic (4-fluorophenyl)(4-((5-methyl-1H-pyrazol-3-yl)amino)quinazolin-2-yl)methanol and its (R)- and (S)-enantiomers are summarized in Table 1.

TABLE 1

| Compound | JAK1 | JAK2 | JAK3 | TYK2 |
|---|---|---|---|---|
| Racemate | 6 | 0.3 | 10.5 | 1.8 |
| (S)(+) | 2.5 | 0.18 | 5 | 1.6 |
| (R)(−) | 15 | 0.5 | 21 | 8.8 |

Example 8 csTF-1 Cell-Based Reporter Assay csTF-1 cells were derived from the human erythroleukemia cell line that was growth dependent on GM-CSF and had an intact GM-CSFR/JAK2/STAT5 pathway. The cell line contained stably integrated beta-lactamase reporter gene under the control of the regulatory factor 1 (irf 1) response element recognized by the activated transcription factor STAT5. csTF-1 cells (Invitrogen K1219) were washed with assay media (97% OPTIMEM/0.5% dialyzed FBS/0.1 mM non-essential amino acids/1 mM Na pyruvate/penicillin/streptomycin) and seeded in the same media at 5×10$^5$ cell/mL in T150 flask. After 16 hr incubation, cells were seeded at 2×10$^5$ cell/well in 50 µL volume, into Costar, clear bottom, 96-well assay plates. Serial dilutions of compounds were added to the plates with final DMSO concentration at 0.5% and GM-CSF at 2 ng/mL and the plates were then incubated at 30° C. and 5% $CO_2$ for 4 hrs. The plates were brought to room temperature before adding Substrate Mixture according to manufacturer's protocol (Invitrogen, Catalog #K1085). The assay plates containing the substrate mixture were incubated in the dark at room temperature for 2 hrs. Blue and green fluorescence were measured with excitation at 409 nm and emission at 460 nm (for blue) and excitation at 409 nm and emission at 530 nm (for green) using Spectra Max Gemini EM. In this cell line, the racemate inhibited GM-CSF stimulated reporter activity with an $EC_{50}$ of 70 nM. The individual enantiomers inhibited GM-CSF stimulated reporter activity with an $EC_{50}$ of 38 and 75 nM for the (S)(+) and (R)(−), respectively.

Example 9

TEL-JAK Cellular Assay

To compare the cellular activity of a compound against each JAK family member, Ba/F3 cell lines were generated that exogenously express each of the four JAK proteins in a constitutively activated state. This is achieved by fusing the dimerization domain of the protein TEL with the kinase domain of the individual JAK proteins. When expressed, these fusion proteins dimerize, causing cross-activation of their associated kinase domains, which leads to phosphorylation of STAT5, among other STAT proteins, depending on the particular kinase. Each cell line was generated by retroviral transduction of the recombinant fusion protein gene and subsequent single cell cloning of each resulting cell line.

To determine cellular anti-JAK activity of a compound, inhibition of the constitutive STAT5 phosphorylation was determined in each cell line. Cells were maintained in RPMI 1640 (Thermo Scientific)+10% FBS with 0.5 µg/mL puromycin (Clontech) to maintain expression of the fusion protein gene. For the assay, cells were washed and resuspended in media +0.5% FBS (without puromycin), and plated at 1E5 cells/well in U-bottom 96-well plates (BD Biosciences). Serially diluted compound was added to the cells and incubated for 2 hrs at 37° C. Cells were then washed with cold PBS and lysed for 15 min with 50 µL/well of ice cold lysis buffer (Cell Signaling Technology), containing protease and phosphatase inhibitor cocktails (Roche Applied Science). Evaluation of phosphorylated STAT5 levels in the lysates was determined using phospho-STAT5a,b kits (Meso Scale Discovery (MSD)) according to manufacturer's instructions. Briefly, plates were blocked for 1 hr with 3% Blocker A in MSD wash buffer (TBS+0.02% Tween 20), and washed on a BioTek ELx405 plate washer. Cell lysates were added at 25 µL/well and incubated for 2 hrs at room temperature. Plates were washed and detection solution containing SULFO-TAG anti-total STAT5a,b antibody was added at 25 µL/well. After an 1 hr incubation, plates were washed and 150 µL/well of MSD read buffer was added before reading plates on a Sector Imager 6000 instrument (MSD).

Example 10

Adenosine $A_3$ Receptor Radioligand Binding Assay

Adenosine $A_3$ receptor, also known as A3AR or ADORA3, is a G protein-coupled receptor (GPCR). Racemic (4-fluorophenyl)(4-((5-methyl-1H-pyrazol-3-yl)amino)quinazolin-2-yl)methanol was tested in an adenosine $A_3$ receptor GTPγS binding assay in antagonist format, according to the procedure described in Jacobson et al., *Neuropharmacology* 1997, 36, 1157-1165, in human CHO-K1 cell line expressing the human adenosine A3 receptor. The final DMSO concentration in the assay was about 0.4%. Incubations of 1 µM, 0.1 µM, and 10 nM of the compound were carried out in duplicates at 30° C. for 30 min in an incubation buffer (20 mM HEPES, pH 7.4, 100 mM NaCl, 10 mM $MgCl_2$, 1 mM DTT, and 1 mM EDTA). The assay was quantitated by measuring the amount of [$^{35}$S]GTPγS bound relative to 2-Cl-IB-MECA response. The $IC_{50}$ of racemic (4-fluorophenyl)(4-((5-methyl-1H-pyrazol-3-yl)amino)quinazolin-2-yl)methanol against adenosine $A_3$ was determined to be 62.9 nM.

Example 11

Adenosine $A_3$ Receptor Radioligand Binding Assay (R)- and (S)-(4-Fluorophenyl)(4-((5-methyl-1H-pyrazol-3-yl)amino)quinazolin-2-yl)methanol was tested in a radioligand binding assay, according to the procedure described in Olah et al., *Mol. Pharmacol.* 1994, 45, 978-982 and Salvatore et al., *Proc. Natl. Acad. Sci. U.S.A.* 1993, 90, 10365-10369, in human recombinant CHO-K1 cells expressing the human adenosine A3 receptor. Incubations of a range of concentration of each compound were carried out in duplicates for 1 h at 25° C. in 25 mM HEPES, pH 7.4, 5 mM $MgCl_2$, 1 mM $CaCl_2$, 0.1% BSA, in the presence of 0.5 nM [$^{125}$I]AB-MECA. Non-specific binding was determined in the presence of 1 µM IB-MECA. Ki values were calculated using the equation of Cheng and Prussof (Cheng et al., *Biochem. Pharmacol.* 1973, 22, 3099-3108) using the observed $IC_{50}$ of the compound, the concentration of the radioligand used in the assay and the historical Kd of the radioligand. The results are summarized in Table 2.

TABLE 2

| Compound | $IC_{50}$ (nM) | $K_i$ (nM) | Hill Coefficient |
|---|---|---|---|
| (S)(+) | 1.55 | 1.42 | 0.811 |
| (R)(−) | 28 | 25.8 | 1.14 |

Example 12

Adenosine $A_3$ Receptor Antagonist Cell Based Assay

To determine the antagonist activity of a compound on the adenosine $A_3$ receptor, two assays were employed by DiscoveRx. The PathHunter β-Arrestin assay monitors the activation of a recombinantly tagged GPCR utilizing enzyme fragment complementation with β-galactosidase (β-Gal) as the functional reporter. For the 13-Arrestin assay, a human ADORA3-expressing PathHunter cell line was grown according to standard procedures and maintained in selective growth media prior to assay. Cells were seeded in 384-well microplates at a density of 5000 cells per well in a total volume of 20 µL and were allowed to adhere and recover overnight prior to compound addition. 2-Cl-IB-MECA agonist dose curves were performed the morning of profiling to determine the $EC_{80}$ value that was used for the following antagonist compound testing. For antagonist determination, cells were preincubated with either (R)- or (S)-(4-fluorophenyl)(4-((5-methyl-1H-pyrazol-3-yl)amino)quinazolin-2-yl)methanol antagonist or the racemic antagonist (5 µL of 5× compound added to cells for 30 min at 37° C.) followed by 2-Cl-IB-MECA agonist challenge at the $EC_{80}$ concentration (5 μL of 6× $EC_{80}$ agonist incubated at 37° C. for 90 min). Assay signal was generated by addition of 15 μL of PathHunter Detection reagent cocktail for 1 hr at room temperature. Microplates were read with a Perkin Elmer Envision instrument for chemiluminescent signal detection. Percentage inhibition was calculated using the following formula: % Inhibition=100%×(1−(Mean RLU of test sample−mean RLU of vehicle control)/(mean RLU of $EC_{80}$ control−mean RLU of vehicle control)). (R)- and (S)-(4-fluorophenyl)(4-((5-methyl-1H-pyrazol-3-yl)amino)quinazolin-2-yl)methanol were calculated to have $IC_{50}$s of 212.5 and 28.5 nM, respectively. The racemic mixture was calculated to have an $IC_{50}$ of 26.2 nM.

Example 13

Inhibition of Phosphodiesterase PDE4

Racemic (4-fluorophenyl)(4-((5-methyl-1H-pyrazol-3-yl)amino)quinazolin-2-yl)methanol was tested in a phosphodiesterase PDE4 inhibition assay, according to the procedure described in Cortijo et al., Br. J. Pharmacol. 1993, 108, 562-568 and Nicholson et al., Trends Pharmacol. Sci. 1991, 12, 19-27. Human U937 cells were used in this assay. The final DMSO concentration in the assay was about 1%. The assay was pre-incubated at 25° C. for 15 min and then incubated at 25° C. for 20 min in an incubation buffer (50 mM Tris-HCl, pH 7.5, 5 mM $MgCl_2$). The assay was quantitated by measuring the amount of [$^3$H]adenosine. The $IC_{50}$ of racemic (4-fluorophenyl)(4-((5-methyl-1H-pyrazol-3-yl)amino)quinazolin-2-yl)methanol against phosphodiesterase PDE4 was determined to be 2.53 μM.

Example 14

Inhibition of Phosphodiesterase PDE5

Racemic (4-fluorophenyl)(4-((5-methyl-1H-pyrazol-3-yl)amino)quinazolin-2-yl)methanol was tested in a phosphodiesterase PDE5 inhibition assay, according to the procedure described in Hidaka and Asano, Biochem. Biophys. Acta 1976, 429, 485-497 and Nicholson et al., Trends Pharmacol. Sci. 1991, 12, 19-27. Human platelets were used in this assay. The final DMSO concentration in the assay was about 1%. The assay was pre-incubated at 25° C. for 15 min and then incubated at 25° C. for 20 min in an incubation buffer (50 mM Tris-HCl, pH 7.5, 5 mM $MgCl_2$). The assay was quantitated by measuring the amount of [$^3$H]guanosine. The $IC_{50}$ of racemic (4-fluorophenyl)(4-((5-methyl-1H-pyrazol-3-yl)amino)quinazolin-2-yl)methanol against phosphodiesterase PDE5 was determined to be 9.34 μM.

Example 15

Radioligand Binding Assay for Melatonin MT

Racemic (4-fluorophenyl)(4-((5-methyl-1H-pyrazol-3-yl)amino)quinazolin-2-yl)methanol was tested in a melatonin MT, GTPγS binding assay, according to the procedure described in Beresford et al., Biochem. Pharmacol. 1998, 56, 1167-1174. Human CHO-K1 cells Chinese hamster ovary were used in this assay. The final DMSO concentration in the assay was about 0.4%. The assay mixture was incubated at 30° C. for 30 min in an incubation buffer (20 mM HEPES, pH 7.4, 100 mM NaCl, 10 mM $MgCl_2$, 1 mM DTT, and 1 mM EDTA). The assay was quantitated by measuring the amount of [$^{35}$S]GTPγS bound relative to 2-iodomelatonin response. The $IC_{50}$ of racemic (4-fluorophenyl)(4-((5-methyl-1H-pyrazol-3-yl)amino)quinazolin-2-yl)methanol against melatonin was determined to be 9.75 μM.

Example 16

Pharmacokinetic Studies of 4(-fluorophenyl)(4-((5-methyl-1H-pyrazol-3-yl)amino)quinazolin-2-yl)methanol Hydrochloride and its R- and S-Enantiomers in Rats Male Sprague-Dawley rats were dosed either intravenously or orally with (4-fluorophenyl)(4-((5-methyl-1H-pyrazol-3-yl)amino)quinazolin-2-yl)methanol, or its R- or S-enantiomer. Blood samples were collected over a 24 hour time-course for determination of pharmacokinetic parameters.

Pre-catheterized (jugular vein), male Sprague-Dawley rats (230-300 g) obtained from Charles River (Hollister, Calif.) were acclimated in the Abmit vivarium (San Diego, Calif.) for at least three days after delivery and before entering a study. Rats were fasted overnight before dosing. Two rats received a single 1 mg/kg intravenous (IV) bolus dose of a test compound formulated in 3:1 PEG 400:water, and three rats received 10 mg/kg oral gavage (PO) dose of a test compound formulated in Pharmatek#6 (Pharmatek Laboratories, Inc., San Diego, Calif.). Blood samples (approximately 1.0 mL) were collected after dosing at specified time points (5 min (IV only), 15, 30 min, 1, 2, 4, 6, and 24 hrs) into tubes containing $K_3$EDTA. The samples collected were placed on wet ice/ice block and processed for plasma within 15 min. For each sample, plasma was separated and stored frozen at approximately −20° C. until analysis.

Plasma samples, calibration, and quality control standards (50 μL) were extracted with five volumes of acetonitrile containing an internal standard (25 ng/mL N-(5-cyclopropyl-1H-pyrazol-3-yl)-2-(difluoro(4-fluorophenyl)methyl)quinazolin-4-amine) and analyzed using LC-MS/MS (Sciex 4000 Qtrap) on a Regis RegisCell 5 μm column (4.6×250 mm), eluting isocratically with hexane/isopropyl alcohol (85:15) at a flow rate of 1.75 mL/min over 9.5 min, and monitoring the 350/332 Da parent mass/fragment mass transition. Each enantiomer's peak area was integrated separately to quantify the R- and S-enantiomer levels, while both peaks were integrated together as a single integral to quantify the level of the racemic compound.

Pharmacokinetic parameters were then calculated from the normalized LC-MS/MS peak areas using the noncompartmental model and linear trapezoidal estimation method using the WinNonlin software (v5.2, Pharsight Corporation, Mountain View, Calif.).

The pharmacokinetic properties of racemic (4-fluorophenyl)(4-((5-methyl-1H-pyrazol-3-yl)amino)quinazolin-2-yl)methanol hydrochloride were determined after administration of the racemic compound. The pharmacokinetic properties of the two enantiomers in the racemic compound were also determined. The results are summarized in Table 3. For oral administration of the racemic compound, the racemic compound has a $C_{max}$ of 2.1 μM, an $AUC_{0-\infty}$ of 8.52 μM·hr, and a half-life ($t_{1/2}$) of 1.2 hrs. The S-isomer in the racemic compound has a $C_{max}$ of 0.49 μM, an $AUC_{0-\infty}$ of 1.84 μM·hr, and a $t_{1/2}$ of 1.4 hrs, and the R-isomer has a $C_{max}$ of 1.66 μM, an $AUC_{0-\infty}$ of 6.50 μM·hr, and a $t_{1/2}$ of 1.2 hrs. For IV administration of the racemic compound, the racemic compound has a clearance (Cl) of 37.27 mL/min/kg, a volume of distribution (Vd) of 2.88 L/kg, an $AUC_{0-\infty}$ of 1.29 μM·hr, and a half-life of 0.9 hr. The S-isomer in the racemic compound has an AUG, of 0.38 μM·hr and a half-life of 0.5 hrs, while the R-isomer has an $AUG_{0-\infty}$ of 0.88 μM·hr and a half-life of 1.0 hr.

The pharmacokinetic properties of (S)-(4-fluorophenyl)(4-((5-methyl-1H-pyrazol-3-yl)amino)quinazolin-2-yl)methanol hydrochloride were determined after administration of the S-isomer. Results are summarized in Table 4. For oral administration of the S-isomer, the S-isomer has a $C_{max}$ of 1.03 µM, an AUG, of 2.20 µM·hr, and a $t_{1/2}$ of 1.1 hrs. For IV administration of the S-isomer, the S-isomer has a clearance of 40.55 mL/min/kg, a volume of distribution (Vd) of 2.10 L/kg, AUG, of 1.18 µM·hr, and a $t_{1/2}$ of 0.6 hrs.

nol, or its R- or S-enantiomer. Plasma was collected over a 24 hour time-course for determination of pharmacokinetic parameters.

Three male cynomolgus monkeys were fasted overnight and through four hours postdose. Two 100 µL aliquots of each dosing formulation were taken predose. Three monkeys were given a single gavage dose of a test compound at 10 mg/kg, followed by an approximately 10.0 mL tap water flush of the gavage tube. After a 1 week washout period, two of the three

TABLE 3

Pharmacokinetic parameters of the racemic compound in rats

| Route | Dose (mg/kg) | Analyte | Cl-obs (mL/min/kg) | Cmax (µM) | Tmax (hrs) | Vz_obs (L/kg) | AUCall (hr · µM) | AUCINF_obs (hr · µM) | HL_Lambda_z (hrs) |
|---|---|---|---|---|---|---|---|---|---|
| IV | 1 | Racemic | 37.27 | | | 2.88 | 1.25 | 1.29 | 0.9 |
| | | S-isomer | NA | | | NA | 0.36 | 0.38 | 0.5 |
| | | R-isomer | NA | | | NA | 0.83 | 0.88 | 1.0 |
| PO | 10 | Racemic | | 2.10 | 2.0 | | 8.06 | 8.52 | 1.2 |
| | | S-isomer | | 0.49 | 1.5 | | 1.71 | 1.84 | 1.4 |
| | | R-isomer | | 1.66 | 2.0 | | 6.19 | 6.50 | 1.2 |

TABLE 4

Pharmacokinetic parameters of the R- and S-isomers in rats

| Compound Administered | Route | Dose (mg/kg) | Analyte | Cl_obs (mL/min/kg) | Cmax (µM) | Tmax (hrs) | Vz_obs (L/kg) | AUCall (hr · µM) | AUCINF_obs (hr · µM) | HL_Lambda_z (hrs) |
|---|---|---|---|---|---|---|---|---|---|---|
| R-isomer | IV | 1 | R-isomer | 40.55 | | | 2.10 | 1.15 | 1.18 | 0.6 |
| S-isomer | IV | 1 | S-isomer | 21.17 | | | 2.86 | 1.67 | 2.29 | 1.6 |
| R-isomer | PO | 10 | R-isomer | | 1.03 | 0.8 | | 2.13 | 2.20 | 1.1 |
| S-isomer | PO | 10 | S-isomer | | 3.01 | 2.0 | | 10.36 | 10.90 | 1.3 |

The pharmacokinetic properties of (R)-(4-fluorophenyl)(4-((5-methyl-1H-pyrazol-3-yl)amino)quinazolin-2-yl)methanol hydrochloride were determined after administration of the R-isomer. Results are summarized in Table 4. For oral administration of the R-isomer, whereas the R-isomer has a $C_{max}$ of 3.01 µM, an $AUC_{0-\infty}$ of 10.90 µM·hr, and a $t_{1/2}$ of 1.3 hrs. For IV administration of the R-isomer, the R-isomer has a clearance of 21.17 mL/min/kg, a volume of distribution (Vd) of 2.86 L/kg, $AUG_{0-\infty}$ of 2.29 µM·hr, and a $t_{1/2}$ of 1.6 hrs.

monkeys received a single IV bolus dose of a test compound at 1 mg/kg in a peripheral vein followed by approximate 1.0 mL saline flush. Blood samples (approximately 1.0 mL) were collected at specified time points (5 min (IV only), 15, 30 min, 1, 2, 4, 6, and 24 hrs) into tubes containing $K_3$EDTA. The samples collected were placed on wet ice/ice block and processed for plasma within 15 min. For each sample, plasma was separated and stored frozen at approximately −20° C. until shipped on dry ice for analysis.

TABLE 5

Pharmacokinetic parameters of the racemic compound and its R- and S-isomers in monkeys

| Compound Administered | Route | Dose (mg/kg) | Cl-obs (mL/min/kg) | Cmax (µM) | Tmax (hrs) | Vz_obs (L/kg) | AUCall (hr · µM) | AUCINF_obs (hr · µM) | HL_Lambda_z (hrs) |
|---|---|---|---|---|---|---|---|---|---|
| Racemic | IV | 1 | 21.27 | | | 5.41 | 2.19 | 2.24 | 2.9 |
| S-isomer | | | 46.49 | | | 8.77 | 1.02 | 1.05 | 2.3 |
| R-isomer | | | 15.17 | | | 7.09 | 3.52 | 3.58 | 4.3 |
| Racemic | PO | 10 | | 5.76 | 3.3 | | 46.20 | 46.92 | 3.5 |
| S-isomer | | | | 1.89 | 2.7 | | 9.66 | 9.93 | 4.7 |
| R-isomer | | | | 8.11 | 2.0 | | 82.77 | 83.07 | 2.7 |

Example 17

Pharmacokinetic Studies of (4-fluorophenyl)(4-((5-methyl-1H-pyrazol-3-yl)amino)quinazolin-2-yl)methanol hydrochloride and its R- and S-enantiomers in Monkeys Male cynomolgus monkeys were dosed orally or intravenously in a single crossover design with (4-fluorophenyl)(4-((5-methyl-1H-pyrazol-3- yl)amino)quinazolin-2-yl)metha- Plasma samples, calibration, and quality control standards (75 µL) were extracted with five volumes of acetonitrile containing an internal standard (25 ng/mL N-(5-cyclopropyl-1H-pyrazol-3-yl)-2-(difluoro(4-fluorophenyl)methyl)quinazolin-4-amine) and analyzed using LC-MS/MS (Sciex 4000 Qtrap) on a Regis RegisCell 5 µm column (4.6×250 mm), eluting isocratically with hexane/isopropyl alcohol (85:15) at a flow rate of 1.75 mL/min over 9.5 min, and monitoring the 350/332 Da parent mass/fragment mass transition. Each enantiomer's peak area was integrated separately to quantify the R- and S-enantiomer levels, while both peaks were integrated together as a single integral to quantify the level of the racemic compound.

Pharmacokinetic parameters were then calculated from the normalized LC-MS/MS peak areas using the noncompartmental model and linear trapezoidal estimation method using the WinNonlin software (v5.2, Pharsight Corporation, Mountain View, Calif.).

The pharmacokinetic properties of racemic (4-fluorophenyl)(4-((5-methyl-1H-pyrazol-3-yl)amino)quinazolin-2-yl) methanol hydrochloride and its enantiomers were determined. The results are summarized in Table 5.

For IV administration of the racemic compound, the racemic compound has a clearance (Cl) of 21.27 mL/min/kg, a volume of distribution ($V_d$) of 5.41 L/kg, and a half-life ($t_{1/2}$) of 2.9 hrs. For oral administration of the racemic compound, the racemic compound has a $C_{max}$ of 5.76 µM and $AUC_{0-\infty}$ of 46.92 µM·hr. The bioavailability of the racemic compound was calculated as >100%, which may indicate nonlinear pharmacokinetics.

For IV administration of the S-isomer, the S-isomer has a clearance (Cl) of 46.49 mL/min/kg, a volume of distribution ($V_d$) of 8.77 L/kg, and a half-life ($t_{1/2}$) of 2.3 hrs. For oral administration of the S-isomer, the S-isomer has a $C_{max}$ of 1.89 µM and $AUC_{0-\infty}$ of 9.93 µM·hr. The bioavailability of the S-isomer was calculated as 89%.

For IV administration of the R-isomer, the R-isomer has a clearance (Cl) of 15.17 mL/min/kg, a volume of distribution ($V_d$) of 7.09 L/kg, and a half-life ($t_{1/2}$) of 4.3 hrs. For oral administration of the R-isomer, the R-isomer has a $C_{max}$ of 8.11 µM and $AUC_{0-\infty}$ of 83.07 µM·hr. The bioavailability of the R-isomer was calculated as >100%.

After oral administration of the S-isomer, both enantiomers were present in plasma in almost equal proportions, having similar AUC and $C_{max}$ values. Notably, the R-isomer was present as an impurity (about 2%) in the S-isomer formulation, but this impurity level is unlikely to account for this observation.

Example 18

CYP450 Inhibition

The ability of the R and S enantiomers of (4-fluorophenyl)(4-((5-methyl-1H-pyrazol-3-yl)amino)quinazolin-2-yl) methanol to inhibit the common drug metabolizing isoforms of cytochrome P450 (CYP) was evaluated against the following isoforms: CYP1A2, CYP2B6, CYP2C8, CYP2C9, CYP2C19, CYP2D6, and CYP3A4. The compounds were incubated in duplicate with eight test compound concentrations (final DMSO concentration of 0.20%) with human liver microsomes (0.25 or 0.50 mg/mL) and NADPH (1 mM) in the presence of CYP isoform specific probe susbtrates (phenacetin, bupropion, taxol, diclofenac, mephenyloin, dextromethorphan, testosterone) at the $K_m$ for 10-20 minutes at 37° C. Selective CYP isoform inhibitors (furafulline, ticlopidine, quercetin, sulfaphenazole, ticlopidine, quinidine, ketoconazole) were screened alongside the test compounds as positive controls. A summary of $IC_{50}$ values is presented in Table 7.

TABLE 6

Pharmacokinetic parameters of the racemic compound and its R- and S-isomers (Chiral analysis)

| Compound Administered | Route | Dose (mg/kg) | Analyte | Cl-obs (mL/min/kg) | Cmax (µM) | Tmax (hrs) | Vz_obs (L/kg) | AUCall (hr · µM) | AUCINF_obs (hr · µM) | HL_Lambda_z (hrs) |
|---|---|---|---|---|---|---|---|---|---|---|
| Racemic | IV | 1 | Racemic | 21.27 | | | 5.41 | 2.19 | 2.24 | 2.9 |
| | | | S-isomer | NA | | | NA | 0.63 | 0.64 | 3.6 |
| | | | R-isomer | NA | | | NA | 1.58 | 1.59 | 3.8 |
| S-isomer | IV | 1 | S-isomer | 46.49 | | | 8.77 | 1.02 | 1.05 | 2.3 |
| | | | R-isomer | NA | | | NA | 0.17 | 0.32 | NA |
| R-isomer | IV | 1 | R-isomer | 15.17 | | | 7.09 | 3.52 | 3.58 | 4.3 |
| | | | S-isomer | NA | | | NA | 0.22 | 0.39 | NA |
| Racemic | PO | 10 | Racemic | | 5.76 | 3.3 | | 46.20 | 46.92 | 3.5 |
| | | | S-isomer | | 0.63 | 4.0 | | 4.90 | 5.06 | 4.6 |
| | | | R-isomer | | 4.98 | 3.3 | | 39.97 | 40.53 | 3.4 |
| S-isomer | PO | 10 | S-isomer | | 1.89 | 2.7 | | 9.66 | 9.93 | 4.7 |
| | | | R-isomer | | 1.38 | 2.7 | | 7.58 | 7.97 | 7.4 |
| R-isomer | PO | 10 | R-isomer | | 8.11 | 2.0 | | 82.77 | 83.07 | 2.7 |
| | | | S-isomer | | 0.42 | 4.7 | | 5.02 | 5.17 | 3 |

Chiral analysis was used to determine the levels of each individual enantiomers in plasma after dosing with the racemic compound, the R-isomer, or the S-isomer. The results are summarized in Table 6. After administration of the racemic compound, the R-isomer was the predominant species for both oral and intravenous routes. The R-isomer accounted for over 85% of the $C_{max}$ and AUC values determined for the racemic compound.

After oral or intravenous administration of the R-isomer, very little the S-isomer was present in plasma, only about 6% relative to the AUC of the R-isomer, some of which may be accounted for the presence of the S-isomer (about 3%) as an impurity in the R-isomer formulation.

TABLE 7

| | $IC_{50}$ (µM) | | |
|---|---|---|---|
| CYP Isoform | Racemate | S enantiomer | R enantiomer |
| 1A2 | <0.31 | <0.31 | 1.7 |
| 2B6 | >40 | >40 | >40 |
| 2C8 | 23.1 | 22.7 | 26.9 |
| 2C9 | 17.4 | 24.6 | 15.2 |
| 2C19 | 14.7 | 15.9 | 11.8 |
| 2D6 | >40 | >40 | >40 |
| 3A4 | 10.9 | 10.5 | 14.8 |

Example 19

In Vivo Efficacy Study in the Mouse TELJAK Mouse Model

This efficacy study was conducted to determine the effect of the R and S enantiomers of (4-fluorophenyl)(4-((5-methyl-1H-pyrazol-3-yl)amino)quinazolin-2-yl)methanol on tumor progression and survival. In this Jak2 dependent murine oncology model, SCID mice are inoculated with BaF3/TEL-JAK cells develop a high peripheral tumor burden as measured by white cell count and massive splenomegaly, with a median time to endpoint (lethality) of 11 days.

Figure 4:
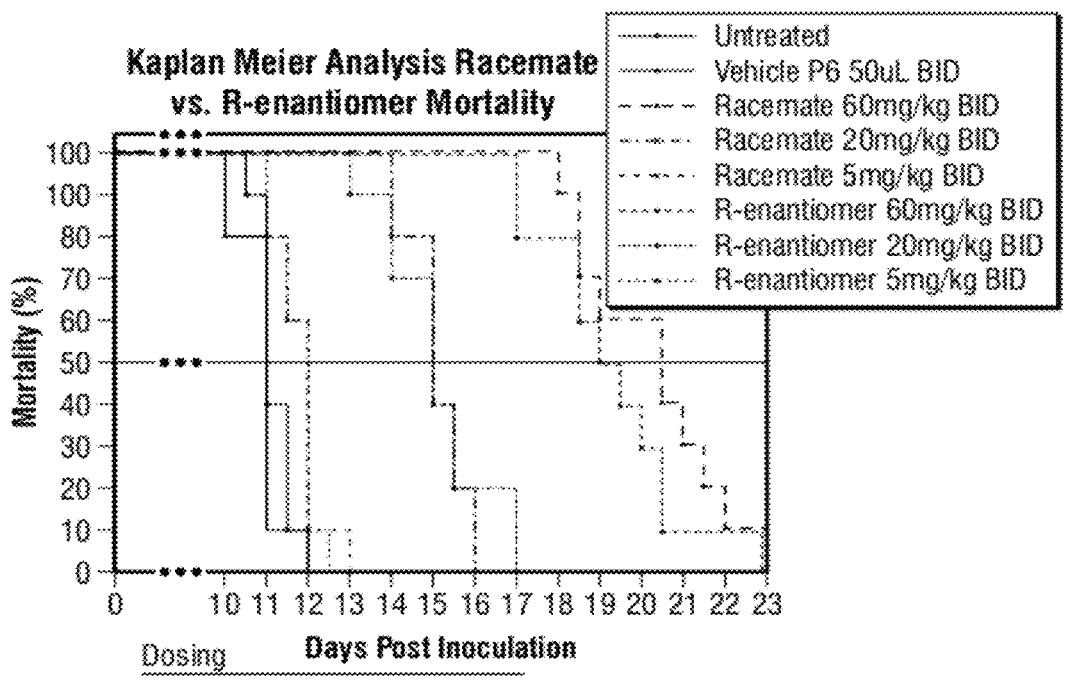
FIG. 4 illustrates the results of the Kaplan Meier survival analysis for (R)-(4-fluorophenyl)(4-((5-methyl-1H-pyrazol-3-yl)amino)quinazolin-2-yl)methanol compared to the racemate.
Figure 5:
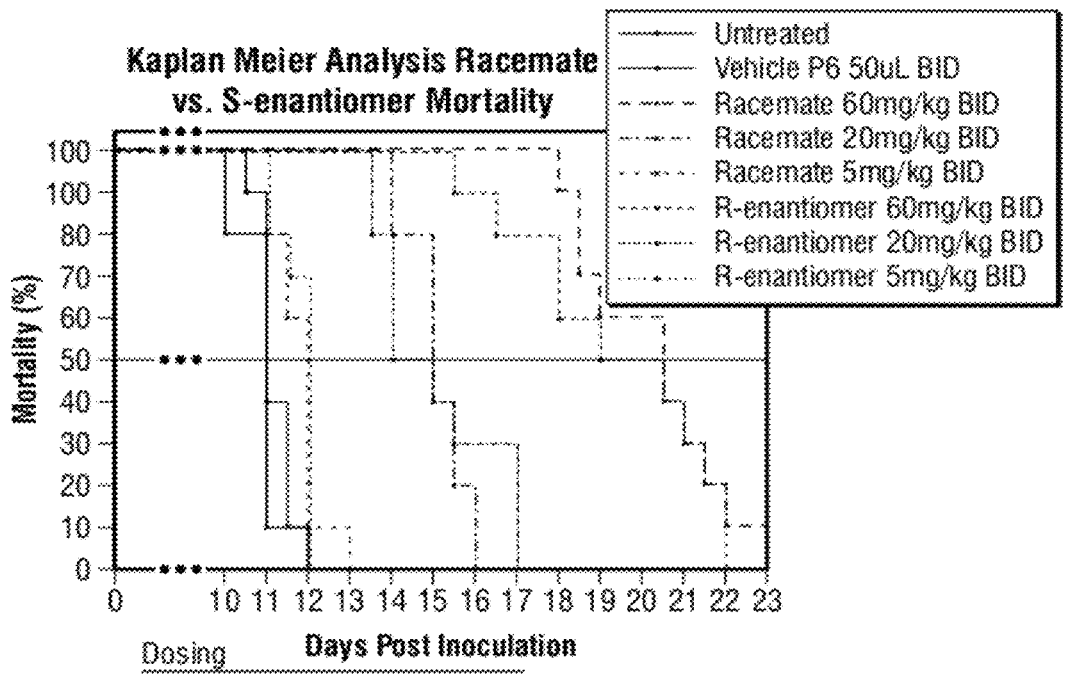
FIG. 5 illustrates the results of the Kaplan Meier survival analysis for (S)-(4-fluorophenyl)(4-((5-methyl-1H-pyrazol-3-yl)amino)quinazolin-2-yl)methanol compared to the racemate.

CB17 SCID mice (Harlan Laboratories) were inoculated with 5e5 BaF3/TEL-JAK cells via tail vein on day 0. Cells were allowed to establish in the animal, and on day 3, dosing was initiated as follows: Vehicle (Pharmatek#6) was administered 50 µL BID to a first group, the racemate (4-fluorophenyl)(4-((5-methyl-1H-pyrazol-3-yl)amino)quinazolin-2-yl)methanol was prepared in Pharmatek #6 and administered at 120 mg/kg/day, 40 mg/kg/day and 10 mg/kg/day, all BID to the second, third and fourth groups, respectively, the (R)-(4-fluorophenyl)(4-((5-methyl-1H-pyrazol-3-yl)amino)quinazolin-2-yl)methanol prepared in Pharmatek #6 was administered to the fifth, sixth and seventh groups at 120 mg/kg/day, 40 mg/kg/day and 10 mg/kg/day, all BID and (S)-(4-fluorophenyl)(4-((5-methyl-1H-pyrazol-3-yl)amino)quinazolin-2-yl)methanol prepared in Pharmatek #6 was administered to the eighth, ninth and tenth groups at 120 mg/kg/day, 40 mg/kg/day and 10 mg/kg/day, all BID. Each treatment group (16 animals per group) received a twice daily dosing for a two week period. An untreated group of 13 animals served as control. FIG. 4 shows the results of the Kaplan Meier survival analysis for (R)-(4-fluorophenyl)(4-((5-methyl-1H-pyrazol-3-yl)amino)quinazolin-2-yl)methanol compared to the racemate. FIG. 5 shows the results of the Kaplan Meier survival analysis for (S)-(4-fluorophenyl)(4-((5-methyl-1H-pyrazol-3-yl)amino)quinazolin-2-yl)methanol compared to the racemate. The percent increase in life span (% ILS) for each compound relative to vehicle treated animals is shown in Table 8.

TABLE 8

| Compound | % ILS | | |
|---|---|---|---|
| | 10 mg/kg/day | 40 mg/kg/day | 120 mg/kg/day |
| Racemate | 9 | 36 | 86 |
| S-enantiomer | 9 | 32 | 80 |
| R-enantiomer | 9 | 36 | 75 |

Example 20

Phase I Clinical Study of Racemic (4-fluorophenyl)(4-((5-methyl-1H-pyrazol-3-yl)amino)quinazolin-2-yl)methanol Phase I clinical study of racemic (4-fluorophenyl)(4-((5-methyl-1H-pyrazol-3-yl)amino)quinazolin-2-yl)methanol HBr salt was performed in volunteers in a double-blind, placebo-controlled, three-part study where in part one, subjects received a single oral dose ranging from 60-750 mg/day of the racemate, where in part two, subjects received a QD dose ranging from 240-720 mg/day of the racemate for 14 days continuously, and in one cohort of the part two study, BID dose of 360 mg of the racemate for 14 days continuously (for a total 720 mg/day), and where in part three a randomized, open-label, two-sequence, two-period, crossover food effect following a single dose was studied. For all parts of the study, PK parameters were evaluated in plasma and in parts one and two, in urine, for racemic (4-fluorophenyl)(4-((5-methyl-1H-pyrazol-3-yl)amino)quinazolin-2-yl)methanol including chiral analysis of its R and S enantiomers. The following PK parameters were computed from plasma concentration data: area under the plasma concentration-time curve from time 0 to time of last quantifiable concentration ($AUC_{0-\tau}$), area under the plasma concentration-time curve from time 0 to infinity ($AUC_{0-\infty}$), maximum observed plasma concentration ($C_{max}$), time to reach $C_{max}$ ($t_{max}$), terminal elimination rate constant ($\lambda z$), terminal half-life ($t_{1/2}$), apparent clearance after extravascular administration (CL/F), and apparent volume of distribution during the terminal phase after extravascular administration (Vz/F). For urine collection data, the following parameters were calculated: total amount of drug excreted in urine from time 0 to 48 hours ($Ae_{0-48}$), —and fraction of drug excreted in urine (Fe). The study was also designed to assess the safety, tolerability and pharmacodynamic effects of the single and multiple oral doses of racemic (4-fluorophenyl)(4-((5-methyl-1H-pyrazol-3-yl)amino)quinazolin-2-yl)methanol on human subjects. The pharmacodynamic effects are based on measurement of STAT phosphorylation levels following ex vivo stimulation with cytokines signaling through JAK2 and JAK1. Also for part two of the study only, flow cytometry was performed to determine the prevalence of cellular subsets as identified by cell-type specific cell surface markers.

Example 21

Catalyst Screening and Optimization

Several asymmetric transfer hydrogenation and hydrogenation reactions of (4-fluorophenyl)(4-(5-methyl-4H-pyrazol-3-ylamino)quinazolin-2-yl)methanone were performed under a variety of conditions to obtain full conversion in the required transformation with high enantiomeric selectivity (e.g., >95% ee). The conversion and chiral purity of the products were determined using a normal phase Phenomenex Lux 5µ Cellulose-2 column eluting with EtOH/Hexane (30/70). Conversion data was also corroborated by reverse phase C-18 and by LCMS. In the examples below, "substrate" and "ketone" refer to (4-fluorophenyl)(4-(5-methyl-4H-pyrazol-3-ylamino)quinazolin-2-yl)methanone, and "alcohol" refers to (4-fluorophenyl)(4-((5-methyl-1H-pyrazol-3-yl)amino)quinazolin-2-yl)methanol. The substrate can be prepared by methods known to those of skill in the art, including methods described elsewhere herein and in U.S. Pub. No. US 2010/0317659, the disclosure of which is incorporated herein by reference in its entirety.

The following analytical method was used in the determination of % conversion for the hydrogenation of (4-fluorophenyl)(4-(5-methyl-4H-pyrazol-3-ylamino)quinazolin-2-yl)-methanone (HPLC): Column: Phenomenex Luna C-18 (2) 100A, 150×4.6 mm, 5µ; Temperature: 30° C.; Mobile Phase A: MeCN, and Mobile Phase B: $H_2O$+0.1% AcOH; Flow rate: 1 mL/min; UV detection: 254 nm; Injection volume: 5 µL; Sample solvent: MeOH. Solvent program used is summarized in Table 9. Retention times for alcohol and ketone, $t_{alcohol}$ and $t_{ketone}$, are 8.6 and 11.8 min, respectively.

The following analytical method was used for the chiral purity determination of hydrogenated products (HPLC): Column: Phenomenex Lux 5µ Cellulose-2–250 mm×4.6 mm; Temperature: 40° C.; Solvent system: 70% Hexane, 30% EtOH; Flow rate: 1 mL/min; UV detection: 254 nm; Injection volume: 5 µL; Sample solvent: EtOH; and Run Time: 20 min. Retention times for amino alcohols ($t_1$ and $t_2$) and ketone are 5.4, 14.4, and 6.6 min, respectively.

TABLE 9

| Time (min) | Solvent A (%) | Solvent B (%) |
|---|---|---|
| 0 | 10 | 90 |
| 2.5 | 10 | 90 |
| 14.5 | 95 | 5 |
| 16.0 | 95 | 5 |
| 16.5 | 10 | 90 |

A. Screening of Ruthenium Catalysed Transfer Hydrogenation

Screening of transfer hydrogenation with catalysts [(S,S)-MsDPEN RuCl(p-cymene)] (Noyori et. al., *Org. Biomol. Chem.*, 2006, 4, 393; Wills et. al., *Tetra. Asymm.*, 1999, 10, 2045) and [(R,R)-Teth-TsDPEN RuCl] (Wills et. al., *J. Am. Chem. Soc.*, 2005, 127, 7318) was undertaken at molar substrate to catalyst ratio (S/C) 50/1 in DMF and DCE with HCOOH/Et$_3$N (10 equiv.) as follows: in Radley's carousel reactor, 87 mg substrate (0.25 mmol), 2 mol % catalyst (0.05 mmol) and 10 equiv. HCOOH/Et$_3$N were heated for 18 hrs at 50° C. in 3 mL of solvent. The % conversion and % ee were determined by HPLC. Results are provided in Table 10.

TABLE 10

| Entry | Solvent | HCOOH/Et$_3$N | % Ketone | % Alcohol | % Impurities | ee (%) |
|---|---|---|---|---|---|---|
| | | | (S,S)-Ms | | | |
| 1 | DMF | 5:2 | 98 | 0 | 2 | ND |
| 2 | DCE | 5:2 | 98 | 0 | 2 | ND |
| 3 | DMF | 1:1 | 35 | 65 | 0 | 36 (1) |
| 4 | DCE | 1:1 | 84 | 16 | 0 | 40 (2) |
| | | | (R,R)-Teth-Ts | | | |
| 5 | DMF | 5:2 | 100 | 0 | 0 | ND |
| 6 | DCE | 5:2 | 95 | 2 | 3 | ND |
| 7 | DMF | 1:1 | 60 | 39 | 0 | 50 (1) |
| 8 | DCE | 1:1 | 47 | 53 | 0 | 20 (2) |

B. Solvent Screening

Further screening with [(S,S)-MsDPEN RuCl(p-cymene)] was undertaken in various solvents at load of S/C 50/1, at 50° C. with two different H-sources (10 eq.). Each reaction was conducted as follows: in Radley's carousel reactor, 87 mg substrate (0.25 mmol), 2 mol % catalyst (0.05 mmol) and 10 equiv. HCOOH/Et$_3$N were heated for 18 hrs at 50° C. in 3 mL of solvent. The % conversion and % ee were determined by HPLC. Results are presented in Table 11.

TABLE 11

| Entry | Solvent | H-source | % Ketone | % Alcohol | % Impurities | ee (%) |
|---|---|---|---|---|---|---|
| 1 | DCE | Et$_3$N/HCOOH (1:1) | 82 | 18 | 0 | ND |
| 2 | MeOH | Et$_3$N/HCOOH (1:1) | 30 | 56 | 12 | 35 (1) |
| 3 | THF | Et$_3$N/HCOOH (1:1) | 6 | 94 | 0 | 43 (1) |
| 4 | EtOAc | Et$_3$N/HCOOH (1:1) | 84 | 16 | 0 | 40 (1) |
| 5 | DCE | 2M NaCOOH | 98 | 2 | 0 | ND |
| 6 | MeOH | 2M NaCOOH | 74 | 26 | 0 | 54 (1) |
| 7 | THF | 2M NaCOOH | 73 | 27 | 0 | 52 (1) |
| 8 | EtOAc | 2M NaCOOH | 87 | 13 | 0 | ND |

C. Screening with In-Situ Catalysts

Further screening of transfer hydrogenation was undertaken with catalysts formed in situ at S/C 50/1 in THF at 50° C. with 1:1 HCOOH/Et$_3$N (10 eq.) as follows: in Radley's carousel reactor, 3 mL of solvent, 87 mg substrate (0.25 mmol), 2 mol % catalyst (0.05 mmol) and 10 equiv. HCOOH/Et$_3$N were heated at 18 hrs at 50° C. The % conversion and % ee were determined by HPLC. Results are presented in Table 12.

TABLE 12

| Precursor | Ligand | % Ketone | % Alcohol | % Impurities | ee (%) |
|---|---|---|---|---|---|
| [RuCl$_2$(benzene)]$_2$ | (R,R)-TsDPEN | 79 | 21 | 0 | 14(2) |
| [RuCl$_2$(p-cymeme)$_2$ | (R,R)-TsDPEN | 34 | 66 | 0 | 54(2) |
| [RuCl$_2$(mesitylene)]$_2$ | (R,R)-TsDPEN | 74 | 26 | 0 | 54(2) |
| [RuCl$_2$(p-cymeme)]$_2$ | (R,R)-1NphDPEN | 47 | 53 | 0 | 40(2) |
| [RuCl$_2$(p-cymeme)]$_2$ | (R,R)-4ClPhDPEN | 38 | 62 | 0 | 50(2) |
| [RuCl$_2$(p-cymeme)]$_2$ | (R,R)-4MeOPhDPEN | 44 | 56 | 0 | 54(2) |
| [RuCl$_2$(p-cymeme)]$_2$ | (R,R)-BuDPEN | 71 | 29 | 0 | 52(2) |
| [RuCl$_2$(p-cymeme)]$_2$ | (R,R)-TsDACH | 9 | 91 | 0 | 78(2) |

D. Tethered Transfer Hydrogenation Catalysts

Additional transfer hydrogenation reactions were undertaken with tethered transfer hydrogenation catalysts at load of S/C 50/1 in THF as follows: in Radley's carousel reactor, 3 mL of solvent, 87 mg substrate (0.25 mmol), 2 mol % catalyst (0.05 mmol) and 10 equiv. HCOOH/Et$_3$N were heated for 18 hrs at 50° C. The % conversion and % ee were determined by HPLC. Results are presented in Table 13.

TABLE 13

| Entry | Catalyst | % Ketone | % Alcohol | % Impurities | ee (%) |
|---|---|---|---|---|---|
| 1 | [(R,R)-TethTsDPEN RuCl] | 67 | 33 | 0 | 64(2) |
| 2 | [(R,R)-TethMsDPEN RuCl] | 41 | 59 | 0 | 59(2) |
| 3 | [(S,S)-TethTsDPEN RuCl] | 49 | 51 | 0 | 61(1) |

E. Screening of Ruthenium Catalysts

Screening of selected ruthenium catalysts was carried out at catalyst loading of 50/1 in MeOH in BIOTAGE ENDEAVOR™ using the following reaction conditions: 3 mL of solvent, 87 mg substrate (0.25 mmol) and 2 mol % catalyst (0.005 mmol) were heated for 18 hrs at 65° C. The % conversion and % ee were determined by HPLC. Results are presented in Table 14.

TABLE 14

| Entry | Catalyst | % Ketone | % Alcohol | % Impurities | ee (%) |
|---|---|---|---|---|---|
| 1 | [(S)-XylPPhos RuCl$_2$](DMF)$_n$ | 86 | 12 | 2 | 33(1) |
| 2 | [(S)-TolBINAP RuCl$_2$](DMF)$_n$ | 94 | 6 | 0 | ND |
| 3 | [(R)-MeBoPhoz RuCl$_2$](DMF)$_n$ | 91 | 9 | 0 | Rac. |
| 4 | [(R)-XylPhanephos RuCl$_2$](DMF)$_n$ | 1 | 99 | 0 | 6(1) |
| 5 | [(R)-H$_8$-BINAM-P RuCl$_2$](DMF)$_n$ | 92 | 8 | 0 | ND |
| 6 | [(S)-BINAP RuCl$_2$(MeCN)$_2$] | 93 | 7 | 0 | ND |
| 7 | [(S)-TethTsDPEN RuCl] | 11 | 89 | 0 | 59(1) |
| 8 | [(R,R)-TsDPEN Ru(p-cymene)]OTf | 98 | 2 | 0 | ND |

F. Screening of Rhodium Catalysts

Screening of rhodium catalysts was carried out at catalyst loading of 50/1 in MeOH and 30 bar H$_2$ in BIOTAGE ENDEAVOR™ using the following reaction conditions: 3 mL of solvent, 87 mg substrate (0.25 mmol) and 2 mol % catalyst (0.005 mmol) were heated for 18 hrs at 65° C. The % conversion and % ee were determined by HPLC. Results are presented in Table 15.

TABLE 15

| Catalyst | % Ketone | % Alcohol | % Impurities | ee (%) |
|---|---|---|---|---|
| [(S)-TolBINAP Rh(COD)]BF$_4$ | 7 | 90 | 3 | 80(2) |
| [(S)-PPhos Rh(COD)]BF$_4$ | 54 | 46 | 0 | 50(2) |
| [(S)-Phanephos Rh(COD)]BF$_4$ | 100 | 0 | 0 | — |
| [(R)-BINAM-P Rh(COD)]BF$_4$ | 96 | 4 | 0 | ND |
| [(S)-MeBoPhoz Rh(COD)]OTf | 0 | 100 | 0 | 60(1) |
| [(S$_a$,R$_c$)-(1Nph)-Quinaphos Rh(COD)]BF$_4$ | 95 | 5 | 0 | ND |
| [(S)-TCFP Rh(COD)]BF$_4$ | 0 | 100 | 0 | 68(1) |
| [(S,S)-Norphos Rh(COD)]BF$_4$ | 96 | 4 | 0 | — |
| [(R,R)-BDPP Rh(COD)]BF$_4$ | 1 | 99 | 0 | Rac. |
| [(S,S)-Chiraphos Rh(COD)]BF$_4$ | 98 | 2 | 0 | ND |
| [(R,R)-DIOP Rh(COD)]BF$_4$ | 99 | 1 | 0 | ND |
| [(S,S,R,R)-Tangphos Rh(COD)]BF$_4$ | 3 | 97 | 0 | 93(1) |
| [(S,S)-MeBPE Rh(COD)]BF$_4$ | 1 | 99 | 0 | 58(1) |
| [(S,S)-PhBPE Rh(COD)]BF$_4$ | 0 | 100 | 0 | 85(1) |
| [CatASium M(S)Rh(COD)]BF$_4$ | 25 | 75 | 0 | 20(2) |
| [CatASium MNN(R)Rh(COD)]BF$_4$ | 2 | 98 | 0 | 37(1) |
| [(R)-MeBoPhoz Rh(COD)]BF$_4$ | 95 | 5 | 0 | ND |
| [(S)-BINAP Rh(COD)]BF$_4$ | 8 | 92 | 0 | 77(2) |
| [(S)-TolPPhos Rh(COD)]BF$_4$ | 16 | 84 | 0 | 81(2) |
| [(S)-XylPhanephos Rh(COD)]BF$_4$ | 0 | 100 | 0 | 7(2) |

G. Catalyst Screening with BoPhoz Ligands

Catalyst screening was undertaken with BoPhoz ligands and [Rh(COD)$_2$]BF$_4$ in MeOH or THF at catalyst load of S/C 100/1 at 30 bar H$_2$ in BIOTAGE ENDEAVOR™ using the following reaction conditions: 3 mL of solvent, 87 mg substrate (0.25 mmol) and 1 mol % catalyst (0.0025 mmol) were heated for 18 hrs at 65° C. In all these cases, the substrate was present during catalyst formation due to solubility issues (i.e., no stock solution could be prepared for later addition). The % conversion and % ee were determined by HPLC. Results are presented in Table 16.

TABLE 16

| Solvent | Ligand | % Ketone | % Alcohol | % Impurities | ee (%) |
|---|---|---|---|---|---|
| MeOH | (R)-MeBoPhoz | 2 | 98 | 0 | 40(2) |
| | (R)-BnBoPhoz | 0 | 100 | 0 | 40(2) |
| | (R)-Phenethylamine (R)-BoPhoz | 0 | 100 | 0 | 10(2) |
| | (S)-Naphthethylamine (R)-BoPhoz | 0 | 100 | 0 | 7(2) |
| THF | (R)-MeBoPhoz | 13 | 97 | 0 | 33(2) |
| | (R)-BnBoPhoz | 12 | 88 | 0 | 66(2) |

TABLE 16-continued

| Solvent | Ligand | % Ketone | % Alcohol | % Impurities | ee (%) |
|---|---|---|---|---|---|
| | (R)-Phenethylamine (R)-BoPhoz | 2 | 98 | 0 | 27(2) |

TABLE 16-continued

| Solvent | Ligand | % Ketone | % Alcohol | % Impurities | ee (%) |
|---|---|---|---|---|---|
| | (S)-Naphthethylamine (R)-BoPhoz | 0 | 100 | 0 | 10(2) |

H. Rhodium Catalysts in THF

Certain rhodium catalysts in THF at catalyst load S/C 50/1 at 30 bar H$_2$ were used in BIOTAGE ENDEAVOR™ reactors with the following reaction conditions: 3 mL of solvent, 87 mg substrate (0.25 mmol) and 2 mol % catalyst (0.005 mmol) were heated for 18 hrs at 65° C. The % conversion and % ee were determined by HPLC. Results are presented in Table 17.

TABLE 17

| Catalyst | % Ketone | % Alcohol | % Impurities | ee (%) |
|---|---|---|---|---|
| [(S)-MeBoPhoz Rh(COD)]Otf | 92 | 3 | 0 | ND |
| [(S)-TCFP Rh(COD)]BF$_4$ | 75 | 5 | 0 | ND |
| [(S,S)-PhBPE Rh(COD)]BF$_4$ | 66 | 34 | 0 | 53(2) |

TABLE 17-continued

| Catalyst | % Ketone | % Alcohol | % Impurities | ee (%) |
|---|---|---|---|---|
| [(S,S,R,R)-Tangphos Rh(COD)]BF$_4$ | 1 | 99 | 0 | 23(1) |

I. Ruthenium Noyori Type Catalysts

Screening was undertaken with Noyori type bis-phosphine Ruthenium diamine catalysts (Noyori et. al., *Angew. Chem. Int. Ed.,* 1998, 37, 1703; Noyori et. al., *Angew. Chem. Int. Ed.* 2001, 40, 1) in IPA, 1M KOtBu in tBuOH (20%) at the catalyst load of 50/1, and 30 bar H$_2$ in BIOTAGE ENDEAVOR™ using the following reaction conditions: 3 mL of solvent, 87 mg substrate (0.25 mmol), 2 mol % catalyst (0.005 mmol) and 1M KOtBu in tBuOH (20%) were heated for 18 hrs at 65° C. The % conversion and % ee were determined by HPLC. Results are presented in Table 18.

TABLE 18

| Catalyst | % Ketone | % Alcohol | % Impurities | ee (%) |
|---|---|---|---|---|
| [(R)-XylPPhos RuCl$_2$ (R)-DAIPEN] | 29 | 71 | 0 | 82(1) |
| [(S)-XylPPhos RuCl$_2$ (R)-DAIPEN] | 35 | 65 | 0 | 85(2) |
| [(R)-PPhos RuCl$_2$ (R)-DAIPEN] | 0 | 100 | 0 | 79(1) |
| [(S)-PPhos RuCl$_2$ (R)-DAIPEN] | 0 | 100 | 0 | 85(2) |
| [(R)-XylPPhos RuCl$_2$ (R,R)-DPEN] | 97 | 1 | 2 | ND |
| [(R)-XylPPhos RuCl$_2$ (S,S)-DPEN] | 87 | 9 | 4 | ND |
| [(R)-PPhos RuCl$_2$ (R,R)-DPEN] | 78 | 22 | 0 | 64(1) |
| [(S)-PPhos RuCl$_2$ (R,R)-DPEN] | 25 | 74 | 1 | 78(1) |
| [(S)-PPhos RuCl$_2$ (S)-DAIPEN] | 2 | 98 | 0 | 74(2) |
| [(R)-PPhos RuCl$_2$ (S)-DAIPEN] | 1 | 99 | 0 | 78(1) |
| [(R)-BINAP RuCl$_2$ (R)-DAIPEN] | 7 | 93 | 0 | 68(1) |
| [(S)-BINAP RuCl$_2$ (R)-DAIPEN] | 12 | 88 | 0 | 59(2) |
| [(S)-XylBINAP RuCl$_2$ (S)-DAIPEN] | 13 | 87 | 0 | 40(2) |
| [(R)-BINAP RuCl$_2$ (R,R)-DPEN] | 94 | 6 | 0 | ND |
| [(R)-XylBINAP RuCl$_2$ (R,R)-DPEN] | 98 | 2 | 0 | ND |
| [(S)-PPhos RuCl$_2$ (R,R)-DACH] | 79 | 21 | 0 | 52(1) |
| [(R)-PPhos RuCl$_2$ (R,R)-DPPN] | 54 | 46 | 0 | 78(1) |
| [(R)-PPhos RuCl$_2$ (S,S)-DPPN] | 58 | 42 | 0 | 67(1) |
| [(R)-BINAP RuCl$_2$ (S,S)-Damtar] | 87 | 13 | 0 | 54(1) |
| [(S)-PPhos RuCl$_2$ (R,R)-Damtar] | 76 | 24 | 0 | 25(2) |
| [(R)-XylPPhos RuCl$_2$ (ampy)] | 91 | 9 | 0 | ND |
| [(R)-PPhos RuCl$_2$ (ampy)] | 75 | 25 | 0 | 4(1) |
| [(R)-MeBoPhoz RuCl$_2$ (ampy)] | 84 | 16 | 0 | 75(1) |
| [(S)-Phanephos RuCl$_2$ (ampy)] | 63 | 37 | 0 | 16(2) |
| [(R)-TolBINAP RuCl$_2$ (R)-DAIPEN] | 2 | 98 | 0 | 60(1) |
| [(S)-BINAP RuCl$_2$ Me$_2$EN] | 85 | 15 | 0 | Rac. |
| [(R)-PPhos RuCl$_2$ (R,R)-DCEN] | 53 | 47 | 0 | 74(1) |
| [(R)-XylPPhos RuCl$_2$ (R,R)-DCEN] | 98 | 2 | 0 | ND |
| [(R)-TolPPhos RuCl$_2$ (R,R)-DCEN] | 87 | 12 | 0 | 60(1) |
| [(R)-BINAP RuCl$_2$ (PPh$_2$CH$_2$CH$_2$NH$_2$)] | 0 | 100 | 0 | 76(1) |
| [(R)-BINAP RuCl (R,R)-DACH]BF$_4$ | 0 | 100 | 0 | 7(2) |
| [(R)-FerroPHOX RuCl$_2$ (PPh$_2$CH$_2$CH$_2$NH$_2$)] | 91 | 9 | 0 | ND |

J. Solvent Screening

Screening with [(S)-PPhos RuCl$_2$ (R)-DAIPEN] in various solvents and 1M KOtBu in tBuOH (20%) at S/C 100/1 and 30 bar H$_2$ was conducted as follows: in BIOTAGE ENDEAVOR™, 3 mL of solvent, 87 mg substrate (0.25 mmol) 1 mol % catalyst (0.0025 mmol) and 1 M KOtBu in tBuOH (20%) were heated for 18 hrs at 65° C. The % conversion and % ee were determined by HPLC. Results are presented in Table 19.

TABLE 19

| Solvent | % Ketone | % Alcohol | % Impurities | ee (%) |
|---|---|---|---|---|
| MeOH | 0 | 100 | 0 | 62(2) |
| EtOH | 0 | 100 | 0 | 55(2) |
| IPA | 0 | 100 | 0 | 68(2) |
| MeOH/tBuOH (1:1) | 0 | 100 | 0 | 71(2) |
| MeOH/THF (1:1) | 0 | 100 | 0 | 57(2) |
| EtOH/THF (1:1) | 0 | 100 | 0 | 60(2) |
| IPA/THF (1:1) | 0 | 100 | 0 | 60(2) |
| THF | 5 | 95 | 0 | 42(2) |

K. Product Stability

Product stability or loss of selectivity with respect to epimerization of the chiral centre over time within the reaction media was determined using two reactions from Table 18 (entries 3 and 4). The residue obtained from natural evaporation was re-dissolved in IPA and heated to 70° C. over 24 hrs. Results are presented in Table 20.

TABLE 20

| End point | +24 Hours in IPA at 70° C. |
|---|---|
| 79% ee (1) | 78% ee (1) |
| 85% ee (2) | 85% ee (2) |

L. Optimization Using [(S)-PPhos RuCl$_2$ (R)-DAIPEN]

Following the results obtained previously with [(S)-PPhos RuCl$_2$ (R)-DAIPEN], a screen of temperature, pressure and base concentration was undertaken at catalyst load S/C 100/1 in IPA with 5-100% 1M KOtBu in tBuOH, 50-65° C. and 10-30 bar H$_2$ was conducted as follows: in BIOTAGE ENDEAVOR™, 3 mL of solvent, 87 mg substrate (0.25 mmol) 1 mol % catalyst (0.0025 mmol) and 5-100% 1M KOtBu in tBuOH were heated for 18 hrs at 65° C. The % conversion and % ee were determined by HPLC. Results are presented in Table 21.

TABLE 21

| Temp. (° C.) | Pressure (Bar H$_2$) | Base (%) | % Ketone | % Alcohol | % Impurities | ee (%) |
|---|---|---|---|---|---|---|
| 50 | 10 | 20 | 13 | 87 | 0 | 90 (2) |
| 50 | 30 | 20 | 2 | 98 | 0 | 91 (2) |
| 65 | 10 | 20 | 0 | 100 | 0 | 75 (2) |
| 65 | 30 | 20 | 0 | 100 | 0 | 85 (2) |
| 65 | 30 | 5 | 0 | 100 | 0 | 77 (2) |
| 65 | 30 | 10 | 0 | 100 | 0 | 70 (2) |
| 65 | 30 | 25 | 0 | 100 | 0 | 68 (2) |
| 65 | 30 | 100 | 2 | 98 | 0 | 57 (2) |

M. Temperature Screening

A series of reactions were undertaken to determine the limits of the reaction with regard to temperature at S/C 100/1 in IPA with 5% or 10% 1M KOtBu in tBuOH and 30 bar as follows: in BIOTAGE ENDEAVOR™, 3 mL of solvent, 87 mg substrate (0.25 mmol) 1 mol % catalyst (0.0025 mmol) and 5% or 10% 1M KOtBu in tBuOH were heated for 18 hrs at 25-50° C. The % conversion and % ee were determined by HPLC. Results are presented in Table 22.

TABLE 22

| Temp. (° C.) | Base (%) | % Ketone | % Alcohol | % Impurities | ee (%) |
|---|---|---|---|---|---|
| 25 | 10 | 99 | 1 | 0 | ND |
| 25 | 5 | 98 | 2 | 0 | ND |
| 30 | 10 | 96 | 4 | 0 | ND |
| 30 | 5 | 94 | 6 | 0 | ND |
| 40 | 10 | 71 | 29 | 0 | 87(2) |
| 40 | 5 | 62 | 38 | 0 | 92(2) |
| 50 | 10 | 2 | 98 | 0 | 91(2) |
| 50 | 5 | 1 | 99 | 0 | 94(2) |

N. Base Screening

The role of base in the reaction was investigated at S/C 100/1 in IPA with 0-5% 1M KOtBu in tBuOH, and 30 bar H$_2$. Reactions were also performed with 10% solvent additives toluene and H$_2$O (entries 6 and 7, Table 23). The reactions were conducted as follows: In BIOTAGE ENDEAVOR™, 3 mL of solvent, 87 mg substrate (0.25 mmol) 1 mol % catalyst (0.0025 mmol) and 0% or 5% 1M KOtBu in tBuOH were heated for 18 hrs at 50° C. The % conversion and % ee were determined by HPLC. Results are presented in Table 23.

TABLE 23

| Base (%) | Solvent Additive | % Ketone | % Alcohol | % Impurities | ee (%) |
|---|---|---|---|---|---|
| 0 | — | 100 | 0 | — | — |
| 1 | — | 2 | 98 | 0 | 94.5(2) |
| 2 | — | 2 | 98 | 0 | 94.0(2) |
| 3 | — | 1 | 99 | 0 | 93.8(2) |
| 4 | — | 1 | 99 | 0 | 94.0(2) |
| 5 | Tolune (10%) | 2 | 98 | 0 | 92.5(2) |
| 5 | H$_2$O (10%) | 0 | 100 | 0 | 93.0(2) |

The samples from entries 2-7 were then combined and evaporated to dryness and the resulting solid was re-analysed by HPLC. This confirmed the results reported were accurate especially with respect to conversion (Isolated solid: 1% SM, 99% products with 93.5% ee].

O. Screening of Catalyst Loading and Base Concentrations

A series of reactions were undertaken with PPhos RuCl$_2$ DAIPEN at various catalyst loadings in IPA with 1-5% 1M KOtBu in tBuOH and 30 bar H$_2$. The reactions were conducted as follows: in BIOTAGE ENDEAVOR™, 3 mL of solvent, 87 mg substrate (0.25 mmol) 0.4 to 1 mol % catalyst and 1-5% 1M KOtBu in tBuOH were heated for 18 hrs at 50° C. The % conversion and % ee were determined by HPLC. Results are presented in Table 24.

TABLE 24

| Loading | B/C | Base (%) [M] | % Ketone | % Alcohol | % Impurities | ee (%) |
|---|---|---|---|---|---|---|
| 100 | 5 | 5 [0.0042] | 1 | 99 | 0 | 93.5 (2) |
| 150 | 7.5 | 5 [0.0042] | 3 | 97 | 0 | 93.4 (2) |
| 200 | 10 | 5 [0.0042] | 4 | 96 | 0 | 93.2 (2) |
| 250 | 12.5 | 5 [0.0042] | 59 | 41 | 0 | 93.0 (2) |
| 100 | 3 | 3 [0.0025] | 2 | 98 | 0 | 94.0 (2) |
| 150 | 3 | 2 [0.0016] | 5 | 95 | 0 | 94.2 (2) |
| 200 | 3 | 1.5 [0.00125] | 3 | 97 | 0 | 94.2 (2) |
| 250 | 3 | 1.2 [0.001] | 2 | 98 | 0 | 94.5 (2) |

P. Screening for Substrate Concentration

The substrate concentration was investigated using [(S)-PPhos RuCl$_2$ (R)-DAIPEN] at catalyst loading of 250/1 in IPA with 0.8% 1M KOtBu in tBuOH and 30 bar H$_2$. The reactions were conducted as follows: in BIOTAGE ENDEAVOR™, 4 mL of solvent, 0.2 to 1.2 mmol substrate, 0.4 mol % catalyst and 3 equivalent 1M KOtBu in tBuOH based on catalyst were heated for 18 hrs at 50° C. The % conversion and % ee were determined by HPLC. Results are presented in Table 25.

TABLE 25

| Conc. (M) [g/L] | B/C | Base (M) | % Ketone | % Alcohol | % Impurities | ee (%) |
|---|---|---|---|---|---|---|
| 0.05 [17] | 3 | 0.0006 | 71 | 29 | 0 | 95.0 (2) |
| 0.1 [34] | 3 | 0.0012 | 6 | 94 | 0 | 94.7 (2) |
| 0.2 [68] | 3 | 0.0024 | 7 | 93 | 0 | 94.2 (2) |
| 0.3 [102] | 3 | 0.0036 | 29 | 71 | 0 | 94.1 (2) |
| 0.05 [17] 10% H$_2$O | 3 | 0.0006 | 0 | 100 | 0 | 94.0 (2) |
| 0.1 [34] 10% H$_2$O | 3 | 0.0012 | 0 | 100 | 0 | 94.0 (2) |
| 0.2 [68] 10% H$_2$O | 3 | 0.0024 | 1.5 | 98.5 | 0 | 95.3 (2) |
| 0.3 [102] 10% H$_2$O | 3 | 0.0036 | 2 | 98 | 0 | 95.9 (2) |

Q. Catalyst Loading

Several reactions were undertaken using [(S)-PPhos RuCl$_2$ (R)-DAIPEN] at catalyst loading of S/C 500/1 and 1000/1 in IPA/H$_2$O (9:1) with 3 eq. 1M KOtBu in tBuOH to catalyst and 30 bar H$_2$. The reactions were conducted as follows: In BIOTAGE ENDEAVOR™, 4 mL of solvent, 0.2 to 1.2 mmol substrate, 0.1 mol % catalyst and 3 equivalent 1M KOtBu in tBuOH based on catalyst were heated for 18 hrs at 50° C. The % conversion and % ee were determined by HPLC. Results are presented in Table 26.

TABLE 26

| Conc. (M) [g/L] | Loading | Base (M) | % Ketone | % Alcohol | % Impurities | ee (%) |
|---|---|---|---|---|---|---|
| 0.3 [104] | 500 | 0.0018 | 4 | 96 | 0 | 96.0(2) |
| 0.3 [104] | 1000 | 0.0009 | 6 | 94 | 0 | 96.2(2) |
| 0.5 [174] | 500 | 0.003 | 4 | 96 | 0 | 94.8(2) |
| 0.5 [174] | 1000 | 0.0015 | 24 | 76 | 0 | 94.7(2) |

R. Reactions with Catalyst Loading 500/1

Reactions were undertaken in the BIOTAGE ENDEAVOR™ using all the different isomers of [PPhos RuCl$_2$ DAIPEN] to determine their performance with a new batch of starting material at catalyst loading of S/C 500/1 in IPA/H$_2$O (9:1) with 3 eq. 1M KOtBu in tBuOH to catalyst and 30 bar H$_2$. The reactions were conducted as follows: In BIOTAGE ENDEAVOR™, 4 mL of solvent, 1.2 mmol substrate, 0.2 mol % catalyst and 3 equivalent 1M KOtBu in tBuOH based on catalyst were heated for 18 hrs at 50° C. The % conversion and % ee were determined by HPLC. Results are presented in Table 27.

TABLE 27

| Catalyst | % Ketone | % Alcohol | % Impurities | ee (%) |
|---|---|---|---|---|
| [(S)-PPhos RuCl₂ (R)-DAIPEN] | 50 | 50 | 0 | 94.6(2) |
| [(S)-PPhos RuCl₂ (S)-DAIPEN] | 5 | 96 | 0 | 95.0(2) |
| [(R)-PPhos RuCl₂ (S)-DAIPEN] | 36 | 64 | 0 | 95.0(1) |
| [(R)-PPhos RuCl₂ (R)-DAIPEN] | 4 | 96 | 0 | 95.0(1) |

S. Reactions with Catalyst Loading 250/1

A series of parallel reactions were undertaken using 420 mg (1.2 mmol) of substrate in 4 mL of IPA/H₂O (9:1) at catalyst loading of S/C 250/1 with 3 eq. 1M KOtBu in tBuOH to catalyst and 30 bar H₂. The reactions were conducted as follows: in BIOTAGE ENDEAVOR™, 4 mL of solvent, 1.2 mmol substrate, 0.4 mol % catalyst and 3 equiv. 1M KOtBu in tBuOH based on catalyst were heated for 18 hrs at 50° C. The % conversion and % ee were determined by HPLC. Results are presented in Table 28.

TABLE 28

| Catalyst | Parallel Reactions | Isolated Yield (g) | % Ketone | % Alcohol | % Impurities | ee (%) |
|---|---|---|---|---|---|---|
| [(S)-PPhos RuCl₂ (S)-DAIPEN] | 14 | 5.0 | 6.2 | 93.8 | 0 | 95.7(2) |
| [(R)-PPhos RuCl₂ (R)-DAIPEN] | 13 | 4.4 | 1.6 | 98.4 | 0 | 96.7(1) |
| [(S)-PPhos RuCl₂ (S)-DAIPEN] | 17 | 5.5 | 1.5 | 98.5 | 0 | 96.5(2) |

Each vial was individually analysed for conversion and selectivity before combination to give the final material. In all cases, MeOH was used as the wash solvent for ensuring maximum dissolution for analysis and transfer of solids.

T. Reactions in 25 mL Parr Vessel a). Reactions with [(S)-PPhos RuCl₂ (R)-DAIPEN]

Two reactions were conducted in a 25 mL Parr vessel using [(S)-PPhos RuCl₂ (R)-DAIPEN] at S/C 500/1 or 1000/1 in IPA/H₂O (9:1) with 3 eq. 1M KOtBu in tBuOH to catalyst and 30 bar H₂. The reactions were conducted as follows: 4 mL of solvent, 0.2-1.2 mmol substrate, 0.4 mol % catalyst and 3 equivalent 1M KOtBu in tBuOH based on catalyst were heated for 18 hrs at 50° C. The % conversion and % ee were determined by HPLC. Results are presented in Table 29.

TABLE 29

| Conc. (M) [g/L] | Loading | Base (M) | % Ketone | % Alcohol | % Impurities | ee (%) |
|---|---|---|---|---|---|---|
| 0.3 [104] | 500 | 0.0018 | 7 | 93 | 0 | 87.7(2) |
| 0.3 [104] | 1000 | 0.0009 | 16 | 84 | 0 | 87.7(2) |

Some loss of selectivity was observed, likely, due to the difference in internal temperature regulation when moving from BIOTAGE ENDEAVOR™ to Parr vessel due to differences in reactor design. Further experiments were conducted on the scale-up and optimisation using standalone Parr autoclaves.

b). Reactions with [(S)-PPhos RuCl₂ (S)-DAIPEN]

A series of reactions were conducted in a 25 mL Parr vessel using [(S)-PPhos RuCl₂ (S)-DAIPEN] at S/C 500/1 or 1000/1 in IPA/H₂O (9:1) with 1M KOtBu in tBuOH (0.0036M) and 30 bar H₂. The reactions were conducted as follows: 8 mL of solvent, 2.4 mmol substrate, 0.1 mol % catalyst and 0.0036 M 1M KOtBu in tBuOH were heated for 18 hrs at 40° C. The % conversion and % ee were determined by HPLC. Results are presented in Table 30.

TABLE 30

| Loading | Time (hr) | % Ketone | % Alcohol | % Impurities | ee (%) |
|---|---|---|---|---|---|
| 1000 | 70 | 1.6 | 98.4 | 0 | 92.7(2) |
|  | Recryst. | 0.68 | 99.32 | 0 | 98.9(2) |
| 500 | 18 | 3 | 97 | 0 | 91.9(2) |
| 250 | 4 | 28 | 72 | 0 | 92.6(2) |
| 250 | 24 | 2 | 98 | 0 | 92.8(2) |
|  | Recryst. | 0.86 | 99.14 | 0 | 97.6(2) |

In two experiments, recrystallisation of the crude material was attempted. The solvent was removed by rotary evaporation at then neat IPA was added at reflux until no more solid remained (~35 mL/g).

c). Reactions with [(S)-PPhos RuCl₂ (S)-DAIPEN] and 3 eq. 1M KOtBu in tBuOH

Reactions were conducted in a 25 mL Parr vessel using [(S)-PPhos RuCl₂ (S)-DAIPEN] at S/C 250/1-1000/1 in IPA/H₂O (1:1) with 3 eq. 1M KOtBu in tBuOH to catalyst and 30 bar H₂. The reactions were conducted as follows: 8 mL of solvent, 2.4 mmol substrate, 0.1 mol % catalyst and 3 eq. 1M KOtBu in tBuOH to catalyst were heated for 18 hrs at 40° C. The % conversion and % ee were determined by HPLC. Results are presented in Table 31.

TABLE 31

| Loading | Time (hr) | % Ketone | % Alcohol | % Impurities | ee (%) |
|---|---|---|---|---|---|
| 1000 | 18 | 5 | 95 | 0 | 95.1(2) |
|  | Recryst. | 3.5 | 96.5 | 0 | 98.1(2) |
| 500 | 18 | 5 | 95 | 0 | 95.0(2) |
| 250 | 18 | 5 | 95 | 0 | 95.0(2) | d). Temperature Screening

A series of reactions were conducted in a 25 mL Parr vessel using [(S)-PPhos RuCl₂ (S)-DAIPEN] at S/C 250/1 in IPA/H₂O (9:1) with 3 eq. 1M KOtBu in tBuOH to catalyst and 30 bar H₂. The reactions were conducted as follows: 8 mL of solvent, 2.4 mmol substrate, 0.1 mol % catalyst and 3 eq. 1M KOtBu in tBuOH to catalyst were heated for 18-70 hrs at 30-40° C. The % conversion and % ee were determined by HPLC. Results are presented in Table 32.

TABLE 32

| Temp. (° C.) | Time (hr) | % Ketone | % Alcohol | % Impurities | ee (%) |
|---|---|---|---|---|---|
| 40 | 24 | 2 | 98 | 0 | 92.8(2) |
|  | Recryst. | 0.86 | 99.14 | 0 | 97.6(2) |
| 35 | 24 | 3 | 97 | 0 | 92.9(2) |
| 30 | 70 | 3 | 97 | 0 | 94.2(2) |
|  | Recryst. | 0.94 | 99.06 | 0 | 97.9(2) | e). Reactions in 100 mL Parr Vessel

Reactions were conducted in a 100 mL Parr vessel using [(S)-PPhos RuCl₂ (S)-DAIPEN] at S/C 250/1 and 1000/1 in IPA/H₂O (9:1) with 3 eq. 1M KOtBu in tBuOH to catalyst and 30 bar H₂. The reactions were conducted as follows: 40 mL of solvent, 12 mmol substrate, 0.1 mol % catalyst and 3 eq. 1M KOtBu in tBuOH to catalyst were heated for over 18 hrs at 40° C. The % conversion and % ee were determined by HPLC. Results are presented in Table 33.

TABLE 33

| Temp. (° C.) | Loading/ Time (hr) | % Ketone | % Alcohol | % Impurities | ee (%) |
| --- | --- | --- | --- | --- | --- |
| 40 | 250/18 | 3 | 97 | 0 | 96.5(2) |
|  | Recryst. | 1.52 | 98.48 | 0 | 98.5(2) |
| 40 | 1000/70 | 12 | 88 | 0 | 97.9(2) | f). Screening for Pressure in Parr Vessel

Reactions were conducted in a 25 mL Parr vessel using [(S)-PPhos RuCl$_2$ (S)-DAIPEN] at S/C 250/1 in IPA/H$_2$O (9:1) with 3 eq. 1M KOtBu in tBuOH to catalyst and 5-30 bar H$_2$. The reactions were conducted as follows: 8 mL of solvent, 2.4 mmol substrate, 0.1 mol % catalyst and 3 eq. 1M KOtBu in tBuOH to catalyst were heated for over 24 hrs at 40° C. All reactions were purged to the pressure value of the individual reaction. The % conversion and % ee were determined by HPLC. Results are presented in Table 34.

TABLE 34

| Pressure (Bar H$_2$) | % Ketone | % Alcohol | % Impurities | ee (%) |
| --- | --- | --- | --- | --- |
| 30 | 2 | 98 | 0 | 92.8(2) |
| Recryst. | 0.86 | 99.14 | 0 | 97.6(2) |
| 20 | 3 | 97 | 0 | 93.2(2) |
| 10 | 4 | 96 | 0 | 93.9(2) |
| 5 | 38 | 62 | 0 | 92.9(2) | g). Screening Additional Heating Time in a Parr Vessel

Reactions were conducted in a 25 mL Parr vessel using [(S)-PPhos RuCl$_2$ (S)-DAIPEN] at S/C 250/1 in IPA/H$_2$O (9:1) with 3 eq. 1M KOtBu in tBuOH to catalyst at 40° C., and 30 bar H$_2$ were heated for over 18 hrs heating, with additional heating for 6 hrs. The reactions were conducted as follows: 8 mL of solvent, 2.4 mmol substrate, 0.1 mol % catalyst and 3 eq. 1M KOtBu in tBuOH based on catalyst were heated for 18 hrs at 40° C. An additional heating for 6 hrs was carried out at 60° C. The % conversion and % ee were determined by HPLC. Results are presented in Table 35.

TABLE 35

| Addition (6 hr period) | Time (hr) | % Ketone | % Alcohol | % Impurities | ee (%) |
| --- | --- | --- | --- | --- | --- |
| 60° C. | 24 | 2 | 98 | 0 | 92.8(2) |
|  | 18 + 6 | 1.12 | 98.88 | 0 | 92.0(2) |
|  | Recryst. | 0.72 | 99.38 | 0 | 97.9(2) |
| 3 eq. Base | 18 + 6 | 1.81 | 98.19 | 0 | 94.2(2) | h). Additional Heating Time in a Parr Vessel at S/C 1000/1

Reactions were conducted in a 25 mL Parr vessel using [(S)-PPhos RuCl$_2$ (S)-DAIPEN] at S/C 1000/1 in IPA/H$_2$O (1:1) with 3 eq. 1M KOtBu in tBuOH to catalyst were heated at 40° C., and 30 bar H$_2$ for over 18 hrs, with additional heating for 6 hrs at 60° C. The reactions were conducted as follows: 8 mL of solvent, 2.4 mmol substrate, 0.1 mol % catalyst and 3 eq. 1M KOtBu in tBuOH based on catalyst were heated for 18 hrs at 40° C. An additional heating for 6 hrs was carried out at 60° C. The % conversion and % ee were determined by HPLC. Results are presented in Table 36.

TABLE 36

| Addition (6 hr period) | Time (hr) | % Ketone | % Alcohol | % Impurities | ee (%) |
| --- | --- | --- | --- | --- | --- |
| 60° C. | 18 | 5 | 95 | 0 | 95.1(2) |
|  | 18 + 6 | 7 | 93 | 0 | 94.0(2) |
| 3 eq. Base | 18 + 6 | 3 | 97 | 0 | 90.8(2) | i). Screening in a 25 mL Parr Vessel with [(S)-PPhosRuCl$_2$(S)-DAIPEN] Catalyst Reactions were conducted in a 25 mL Parr vessel using [(S)-PPhosRuCl$_2$(S)-DAIPEN] at S/C 250/1 in IPA/H$_2$O (9:1 or 1:1) with 3 eq. 1M KOtBu as follows: 8 mL of solvent, 2.4 mmol substrate, 0.1 mol % catalyst and 3 eq. 1M KOtBu in tBuOH based on catalyst were heated at 30-35° C. and 30 bar H$_2$ for over 18 hrs. The % conversion and % ee were determined by HPLC. Results are presented in Table 37.

TABLE 37

| Solvent | Time (hr) | % Ketone | % Alcohol | % Impurities | ee (%) |
| --- | --- | --- | --- | --- | --- |
| IPA/H$_2$O (9:1) | 18 | 5 | 95 | 0 | 95.2(1) |
| IPA/H$_2$O (1:1) | 18 | 2 | 98 | 0 | 93.8(1) | j). Screening in a 100 mL Parr Vessel with [(S)-PPhosRuCl$_2$(S)-DAIPEN] Catalyst Reactions were conducted in a 100 mL Parr vessel using [(S)-PPhosRuCl$_2$(S)-DAIPEN] at S/C 250/1 in IPA/H$_2$O (9:1 or 1:1) with 3 eq. 1M KOtBu in tBuOH as follows: 40 mL of solvent, 12 mmol substrate, 0.4 mol % catalyst and 3 eq. 1M KOtBu in tBuOH based on catalyst were heated for over 18 hrs at 40° C. and 30 bar H$_2$. The % conversion and % ee were determined by HPLC. Results are presented in Table 38.

TABLE 38

| Solvent | Time (hr) | % Ketone | % Alcohol | % Impurities | ee (%) |
| --- | --- | --- | --- | --- | --- |
| IPA/H$_2$O (9:1) | 18 | 6 | 94 | 0 | 93.6(1) |
| IPA/H$_2$O (1:1) | 18 | 2 | 98 | 0 | 94.0(1) | k). Screening in a 300 mL Parr Vessel with [(S)-PPhosRuCl$_2$(S)-DAIPEN] and [(R)-PPhosRuCl$_2$(R)-DAIPEN]

Reactions were conducted in a 300 mL Parr vessel using [(S)-PPhosRuCl$_2$(S)-DAIPEN] and [(R)-PPhosRuCl$_2$(R)-DAIPEN] at S/C 250/1 in IPA/H$_2$O (9:1) with 3 eq. 1M KOtBu in tBuOH as follows: 160 mL of solvent, 48 mmol substrate, 0.4 mol % catalyst and 3 eq. 1M KOtBu in tBuOH based on catalyst were heated for over 18 hrs at 40° C. and 30 bar H$_2$. The % conversion and % ee were determined by HPLC. Results are presented in Table 39.

TABLE 39

| Catalyst | % Ketone | % Alcohol | % Impurities | ee (%) |
| --- | --- | --- | --- | --- |
| [(S)-PPhos RuCl$_2$ (S)-DAIPEN] | 0.65 | 99.35 | 0 | 95.1(2) |
| White solid | 0.62 | 99.38 | 0 | 99.0(2) |
| Dark brown solution | 0 | 100 | 0 | 66(2) |
| Isolated yield: 14.0 g, 83.5% | | | | |
| [(R)-PPhos RuCl$_2$ (R)-DAIPEN] | 1.60 | 98.4 | 0 | 96.0(1) |
| Off white solid | 1.35 | 98.65 | 0 | >99(1) |
| Dark brown solution | 0 | 100 | 0 | 72(1) |
| Isolated yield: 14.0 g, 83.5% | | | | | l). Screening in a 600 mL Parr Vessel with [(S)-PPhosRuCl$_2$(S)-DAIPEN] and [(R)-PPhosRuCl$_2$(R)-DAIPEN]

Reactions were conducted in a 600 mL Parr vessel using [(S)-PPhosRuCl$_2$(S)-DAIPEN] and [(R)-PPhosRuCl$_2$(R)-

DAIPEN] at S/C 250/1 in IPA/H$_2$O (9:1) with 3 eq. 1M KOtBu in tBuOH to catalyst at 40° C., and 30 bar H$_2$ for over 18 hrs heating. The reactions were conducted as follows: 320 mL of solvent, 96 mmol substrate, 0.4 mol % catalyst and 3 eq. 1M KOtBu in tBuOH based on catalyst were heated for over 18 hrs at 40° C. The % conversion and % ee were determined by HPLC. Results are presented in Table 40.

TABLE 40

| Catalyst | % Ketone | % Alcohol | % Impurities | ee (%) |
|---|---|---|---|---|
| [(S)-PPhos RuCl$_2$ (S)-DAIPEN] | 1.88 | 98.12 | 0 | 95.6(2) |
| White solid | 1.75 | 98.25 | 0 | 99.4(2) |
| Dark brown solution | 0 | 100 | 0 | 67(2) |
| Isolated yield: 29.5 g, 88% | | | | |
| [(R)-PPhos RuCl$_2$ (R)-DAIPEN] | 1.5 | 98.5 | 0 | 96.1(1) |
| Off white solid | 1.32 | 98.68 | 0 | >99(1) |
| Dark brown solution | 0 | 100 | 0 | 68(1) |
| Isolated yield: 30.5 g, 91% | | | | |

Example 22

Achiral Reduction

In this reaction, catalytic achiral reduction of (4-fluorophenyl)(4-(5-methyl-4H-pyrazol-3-ylamino)quinazolin-2-yl)methanone was conducted with a heterogeneous Pd/C catalyst to operate under transfer hydrogenation conditions.

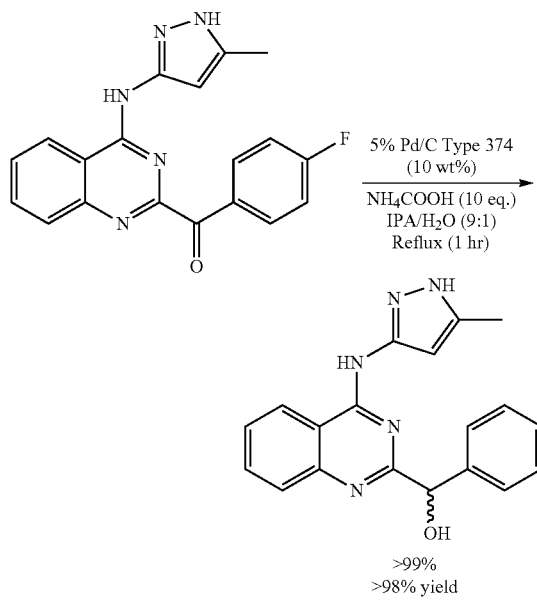

The reaction was conducted using a 5% Pd/C Type 374 at 10 wt % in IPA/H$_2$O (9:1) with NH$_4$COOH (10 eq.) at reflux for over 1 hr. Sampling of the reaction after 1 hr showed full conversion, the reaction was then filtered while still hot to allow efficient removal of the catalyst and the products were precipitated from the filtrate with H$_2$O. The product isolated was a white solid with >99% conversion and >98% isolated yield.

Example 23

Based on the screening reactions described in Example 20, the following conditions were selected as suitable for a benchmark.

A. Benchmark Procedure

A Parr vessel was charged with (4-fluorophenyl)(4-(5-methyl-4H-pyrazol-3-ylamino)quinazolin-2-yl)methanone (1.67 g, 4.8 mmol), (R)-PPhos RuCl$_2$ (R)-DAIPEN (5.4 mg, S/C 1,000/1) and a solution of i-PrOH—H$_2$O (9:1 v/v, 16 mL). The vessel was sealed and purged with N$_2$ by filling to 3 bar for 1 min and then venting, a further 5 purges was done with stirring (1500 rpm). A solution of t-BuOK/t-BuOH (1M, 14 μL) in i-PrOH—H$_2$O (9:1 v/v, 1 mL) was added and the reaction purged with N$_2$ according to the previous sequence. The vessel was then purged with H$_2$ by filling to 30 bar for 1 min and venting, a further 5 purges was done with stirring (1500 rpm). The reaction was then heated to 40° C. and maintained at this temperature and pressure for 16 hrs.

Benchmark reaction conditions were tested initially, details of a reaction procedure are given below. A number of experimental variations were then compared and analysed for reaction conversion. The crude reaction slurry was diluted with THF to obtain a homogeneous solution for analysis.

Table 41 below provides data for conditions screening, (R)-PPhos RuCl$_2$ (R)-DAIPEN or (S)-PPhos RuCl$_2$ (S)-DAIPEN pre-catalyst.

B. Screening of Conditions to Increase Solubility

The following conditions were varied in attempts to increase solubility of the substrate: increased reaction temperature (40° C. vs 60° C.), increased reaction volume, adjustments in solvent system for improved solubility, and intermittent shaking of reactor. The reaction conditions and results are summarized in Table 42. Notes to Table 42 are: a. Conversion calculated as % peak area for product vs. starting material, (prod/prod+sm)×100, peak area at 210 nm using HPLC analysis (reverse phase method) as 254 nm; b. Incomplete conversion resulted in partial overlap of the first enantiomer and starting material giving some error in ee measurement, number in parenthesis denotes the major peak 1=early eluting 2=late eluting; c. A solution of (R)-PPhos RuCl$_2$ (R)-DAIPEN in i-PrOH—H$_2$O (9:1 v/v, 1 mL) and t-BuOK/t-BuOH was heated to 50° C. for 10 min under N$_2$ before addition to the reaction; d. Equivalents relative to catalyst; e. Pressure reduced over course of reaction due to H$_2$ consumption; f. Sample taken from reaction slurry; and g. mol % relative to substrate.

The results from sampling the reaction at various positions of the reactor are given in more detail below in Table 43. Notes to Table 43: a. Conversion calculated as % peak area for product vs. starting material, (prod/prod+sm)×100, peak area at 210 nm using HPLC analysis (reverse phase method) as 254 nm; b. Incomplete conversion resulted in partial overlap of the first enantiomer and starting material giving some error in ee measurement, number in parenthesis denotes the major peak 1=early eluting 2=late eluting; c. A solution of (R)-PPhos RuCl$_2$ (R)-DAIPEN in i-PrOH—H$_2$O (9:1 v/v, 1 mL) and t-BuOK/t-BuOH was heated to 50° C. for 10 min under N$_2$ before addition to the reaction; d. Equivalents relative to catalyst.

C. Hydrogen Pressure

Experiments were conducted to demonstrate the effect of pressure (5 bar and 30 bar) and catalyst loading (2,000/1, 4,000/1, 5,000/1 and 10,000/1) on the conversion and selectivity. The results are given below in Table 44. Notes to Table 44: a. Conversion calculated as % peak area for product vs. starting material, (prod/prod+sm)×100, peak area at 210 nm using HPLC anaylsis (reverse phase method) as 254 nm; b. Incomplete conversion resulted in partial overlap of the first enantiomer and starting material giving some error in ee measurement, number in parenthesis denotes the major peak 1=early eluting 2=late eluting; c. A solution of (R)-PPhos RuCl$_2$ (R)-DAIPEN in i-PrOH—H$_2$O (9:1 v/v, 1 mL) and t-BuOK/t-BuOH was heated to 50° C. for 10 min under N$_2$ before addition to the reaction; d. Equivalents relative to catalyst; e. Pressure reduced over course of reaction due to $H_2$ consumption; f. Sample taken from reaction slurry; and g. mol % relative to substrate.

D. Mixing Efficiency

During the course of reaction optimisation it was observed that minor differences in the baffle lengths within the reaction vessel cause varying mixing efficiencies. The observed differences in conversion depending on the baffle position indicated that efficient stirring was required for higher conversion. Results are provided in Table 45.

E. Effect of Co-Solvents

A comparison of co-solvents was done to increase reactivity by higher substrate solubility. For comparison, conditions giving low conversion using the standard solvent mixture (IPA-$H_2O$, 9:1) were chosen. The reaction mixture was heated to 60° C. for 16 hrs and catalyst loading of 4000/1 S/C was used. The results are given below in Table 45.

TABLE 41

| Entry | Method Variation | Catalyst | Loading (S/C) | Additive (eq.) | Time (hr) | Temp. (° C.) | $H_2$ (bar) | Solvent (conc./M) | Conv. (%)[a] | ee (%)[b] |
|---|---|---|---|---|---|---|---|---|---|---|
| 1 | None | (R,R) | 1000 | — | 16 | 40 | 30 | 0.28 | 84.7 | >94.4 |
| 2 | IPA-$H_2O$ (1:1) | (R,R) | 1000 | — | 16 | 40 | 30 | 0.28 | 83.6 | — |
| 3 | Increased conc. | (R,R) | 1000 | — | 16 | 40 | 30 | 0.53 | 85.5 | — |
| 4 | Weak base | (R,R) | 1000 | HCOONa (10%) | 16 | 40 | 30 | 0.28 | 4.4 | — |
| 5 | Pre-activated catalyst (0.3% t-BuOK) | (R,R) | 1000 | — | 64 | 40 | 30 | 0.28 | 89.9 | >91.8 |
| 6 | Pre-activated catalyst (0.6% t-BuOK) | (R,R) | 1000 | — | 64 | 40 | 30 | 0.28 | 90.0 | >95.4 |

[a] Conversion calculated as % peak area for product vs. starting material, (prod/prod + sm) × 100, peak area at 210 nm using HPLC anaylsis (reverse phase method) as 254 nm.
[b] Incomplete conversion resulted in partial overlap of the first enantiomer and starting material giving some error in ee measurement.

TABLE 42

| Entry | Method Variation | Scale (g) | Catalyst | Loading (S/C) | Additive (eq.) | Time (hr) | Temp. (° C.) | $H_2$ (bar) | Solvent (conc./M) | Conv. (%)[a] | ee (%)[b] |
|---|---|---|---|---|---|---|---|---|---|---|---|
| 1 | None | 1.67 | (R,R) | 1000 | — | 16 | 40 | 30 | 0.3 | 84.7 | >94.4(1) |
| | | | | | Increased Temperature (60° C.) | | | | | | |
| 2 | 60° C. 3 eq. t-BuOK[d] | 1.67 | (R,R) | 1000 | — | 16 | 60 | 30 | 0.3 | 96.0 | >93.6(1) |
| 3 | 60° C., weak base | 1.67 | (R,R) | 1000 | — | 16 | 60 | 30 | 0.3 | 23.8 | — |
| 4 | 60° C. 6 eq. t-BuOK[d] | 3.34 | (R,R) | 2000 | HCOONa (10%)[g] | 16 | 60 | 30 | 0.6 | 91.2 | >93.2(1) |
| 5 | 60° C. 6 eq. t-BuOK[d] | 3.34 | (R,R) | 2000 | (R)-DAIPEN (1 eq.)[d] | 16 | 60 | 30 | 0.6 | 90.3 | >95.2(1) |
| | | | | | Increased Vessel Usage (~70%) | | | | | | |
| 6 | 60° C. 6 eq. t-BuOK[d] | 6.68 | (S,S) | 2000 | — | 64 | 60 | 30[e] | 0.6 | 98.0 | 99.2(2) |
| 7 | 60° C. 6 eq. t-BuOK[d] | 6.68 | (S,S) | 4000 | — | 64 | 60 | 30 | 0.6 | 98.9 | 96.8(2) |
| 8 | 60° C. 6 eq. t-BuOK[d] | 6.68 | (S,S) | 2000 | — | 16 | 60 | 30[e] | 0.6 | 97.8 | 97.3(2) |
| 9 | 60° C. 6 eq. t-BuOK[d] | 6.68 | (S,S) | 2000 | — | 16 | 40 | 30[e] | 0.6 | 38.4[f] | |

TABLE 43

| Entry | Method Variation | Scale (g) | Catalyst | Loading (S/C) | Sample Position | Conv. (%)[a] | ee (%)[b] |
|---|---|---|---|---|---|---|---|
| | Standard Vessel Usuage (~35%) | | | | | | |
| 1 | Preactivated catalyst, 60° C., 0.3M, 64 hrs | 1.67 | (R,R) | 1000 | Overall | 89.9 | >91.8(1) |
| 2 | | | | | Reactor-bottom | 97.9 | — |
| 3 | | | | | Reaction-top | ND | — |
| 4 | 60° C. (3 eq. t-BuOK)[d], 0.3M, 16 hrs | 1.67 | (R,R) | 1000 | Overall | 96.0 | >93.6(1) |
| 5 | | | | | Reactor-bottom | 98.2 | — |
| 6 | | | | | Reaction-top | 96.0 | — |
| 7 | 60° C. (6 eq. t-BuOK)[d], 0.6M, 16 hrs | 3.34 | (R,R) | 2000 | Overall | 91.2 | >93.2 |
| 8 | | | | | Reactor-bottom | 96.2 | — |
| 9 | | | | | Reaction-top | 41.7 | — |
| 10 | 60° C. (6 eq. t-BuOK)[d], 0.6M 16 hrs | 3.34 | (R,R) | 2000 | Overall | 90.3 | >95.2(1) |
| 11 | (R)-DAIPEN 1 eq.[d] | | | | Reactor-bottom | 91.8 | — |
| 12 | | | | | Reaction-top | 38.4 | — |
| | Increased Vessel Usage (~70%) | | | | | | |
| 13 | 60° C. (6 eq. t-BuOK)[d], 0.6M, 64 hrs | 6.68 | (S,S) | 2000 | Overall | 98.0 | 99.2(2) |
| 14 | | | | | Reactor-bottom | 98.1 | — |
| 15 | | | | | Reaction-top | 99.5 | — |

TABLE 43-continued

| Entry | Method Variation | Scale (g) | Catalyst | Loading (S/C) | Sample Position | Conv. (%)[a] | ee (%)[b] |
|---|---|---|---|---|---|---|---|
| 16 | 60° C. (6 eq. t-BuOK)[d], 0.6M, 64 hrs | 6.68 | (S,S) | 4000 | Overall | 98.9 | 96.8(2) |
| 17 | | | | | Reactor-bottom | 99.0 | — |
| 18 | | | | | Reaction-top | 96.9 | — |
| 19 | 60° C. (6 eq. t-BuOK)[d], 0.6M, 16 hrs | 6.68 | (S,S) | 2000 | Overall | 97.8 | 97.3(2) |
| 20 | | | | | Reactor-bottom | 97.8 | — |
| 21 | | | | | Reaction-top | 97.9 | — |

TABLE 44

| Entry | Method Variation | Scale (g) | Catalyst | Loading (S/C) | Additive (eq.) | Time (hr) | Temp. (° C.) | $H_2$ (bar) | Solvent (conc./M) | Conv. (%)[a] | ee (%)[b] |
|---|---|---|---|---|---|---|---|---|---|---|---|
| 1 | 60° C. (6 eq. t-BuOK)[d] | 6.68 | (S,S) | 4000 | — | 64 | 60 | 30 | 0.6 | 98.9 | 96.8(2) |
| 2 | 60° C. (6 eq. t-BuOK)[d] | 6.68 | (S,S) | 4000 | — | 16 | 60 | 30[e] | 0.6 | 98.8 | 96.4(2) |
| 3 | 70° C. (6 eq. t-BuOK)[d] | 6.68 | (S,S) | 10000 | — | 16 | 70 | 30[e] | 0.6 | 91.8 | 94.8(2) |
| 4 | 60° C. (6 eq. t-BuOK)[d] | 6.68 | (S,S) | 2000 | — | 16 | 60 | 5 | 0.6 | 94.9 | 96.2(2) |
| 5 | 70° C. (6 eq. t-BuOK)[d] | 6.68 | (S,S) | 2000 | — | 16 | 70 | 5 | 0.6 | 98.7 | 96.0(2) |
| 6 | 70° C. (6 eq. t-BuOK)[d] | 6.68 | (S,S) | 4000 | — | 16 | 70 | 5 | 0.6 | 97.8 | 94.9(2) |
| 7 | 80° C. (6 eq. t-BuOK)[d] | 6.68 | (S,S) | 5000 | — | 16 | 80 | 5 | 0.6 | 99.1 | 94.2(2) |
| 8 | 70° C. (6 eq. t-BuOK)[d] | 6.68 | (S,S) | 10000 | — | 88 | 70 | 5 | 0.6 | 99.7 | 95.4(2) |

TABLE 45

| Entry | Scale (g) | Catalyst | Loading (S/C) | Solvent 1 (v %) | Solvent 2 (v %) | Solvent 3 (v %) | Baffle (L/S)[h] | Time (hr) | Temp. (° C.) | $H_2$ (bar) | Solvent (conc./M) | Conv. (%)[a] | ee (%)[b] |
|---|---|---|---|---|---|---|---|---|---|---|---|---|---|
| 1 | 6.68 | (S,S) | 4000 | IPA (90) | $H_2O$ (10) | — | L | 16 | 60[f] | 5 | 0.6 | 38.5[c] | — |
| 2 | 6.68 | (S,S) | 4000 | IPA (80) | $H_2O$ (10) | THF (10) | S | 16 | 60[f] | 5 | 0.6 | 15.8[c] | — |
| 3 | 6.68 | (S,S) | 4000 | IPA (80) | $H_2O$ (10) | DMSO (10) | L | 16 | 60[f] | 5 | 0.6 | 90.1 | 98.9(2)[d] |
| 4 | 6.68 | (S,S) | 4000 | IPA (90) | | DMSO (10) | S | 16 | 60[g] | 5 | 0.6 | 19.7[c] | — |
| 5 | 6.68 | (S,S) | 4000 | IPA (70) | $H_2O$ (10) | DMSO (20) | L | 40[e] | 60[f] | 5 | 0.6 | 99.6[e] | 96.0(2) |
| 6 | 6.68 | (S,S) | 4000 | IPA (70) | $H_2O$ (10) | DMSO (20) | L | 16 | 60[f] | 5 | 0.6 | 98.9 | 96.6(2) |
| 7 | 6.68 | (S,S) | 4000 | IPA (80) | $H_2O$ (10) | MeOH (10) | L | 16 | 60[g] | 5 | 0.6 | 36.8[c] | — |
| 8 | 6.68 | (S,S) | 4000 | IPA (80) | $H_2O$ (10) | DMSO (10) | S | 16 | 60[g] | 5 | 0.6 | 50.6[c] | — |
| 9 | 6.68 | (S,S) | 4000 | IPA (80) | $H_2O$ (10) | DMSO (10) | L | 16 | 60[g] | 5 | 0.6 | 85.0 | — |

Notes to Table 45: a. Conversion calculated as % peak area for product vs. starting material, (prod/prod+sm)×100, peak area at 210 nm using HPLC anaylsis (reverse phase method) as 254 nm; b. Incomplete conversion resulted in partial overlap of the first enantiomer and starting material giving some error in ee measurement, number in parenthesis denotes the major peak 1=early eluting 2=late eluting; c. HPLC sample taken from crude reaction mixture as a suspension in THF as substrate has poor solubility; d. ee measured from HPLC of isolated solid; e. Available hydrogen consumed within initial 16 hrs before pressure was reset to 5 bar for a further 24 hrs; f. Hydrogen source via burette; f. Hydrogen supply via flow meter; h. L/S denotes the use of longer or shorter baffle.

Figure 6:
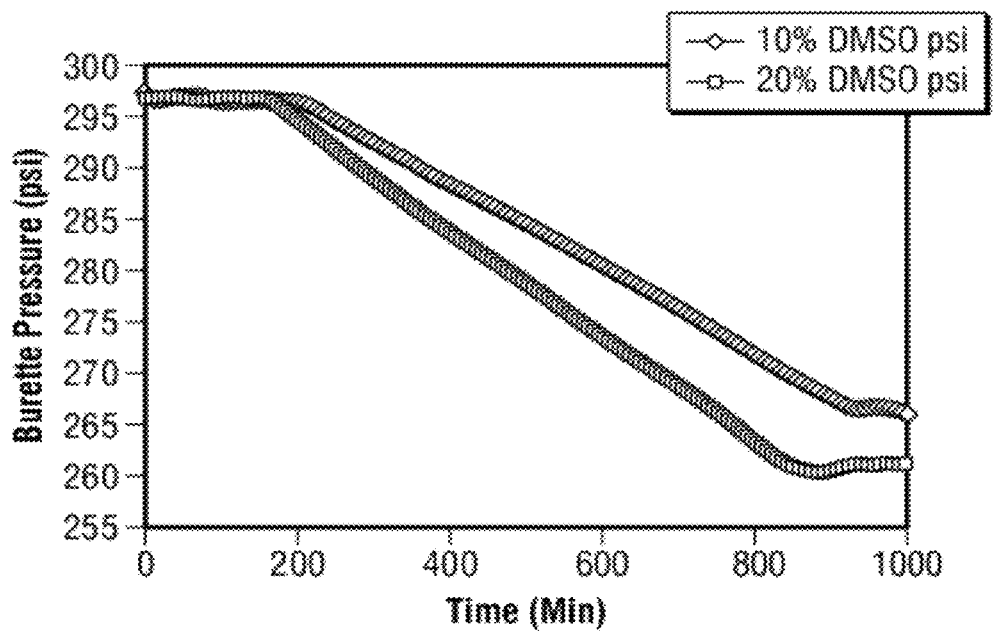
FIG. 6 provides comparison of hydrogen uptake for hydrogenation of (4-fluorophenyl)(4-(5-methyl-4H-pyrazol-3-ylamino)quinazolin-2-yl)methanone using 10% and 20% DMSO (v/v) co-solvent with isopropyl alcohol at 60° C., hydrogen pressure of 5 bar, and catalyst loading of 4000/1 S/C.

Comparison of hydrogen uptake for 10% and 20% DMSO (v/v) co-solvent is shown in FIG. 6.

F. Solubility Studies

Solubility tests were conducted by adding (4-fluorophenyl)(4-(5-methyl-4H-pyrazol-3-ylamino)quinazolin-2-yl)methanone in small portions to a number of solvents until a suspended solid persisted. A number of solvents were selected for this study based on their suitability as co-solvents for the reaction. The results are given below in Table 46.

TABLE 46

| Entry | Solvent(s) | Solubility (mg/mL) | Temp. (° C.) |
|---|---|---|---|
| 1 | DMSO | 12-149 | 20 |
| 2 | THF | <17 | 20 |
| 3 | IPA-$H_2O$ (9:1) | <7 | 20 |
| 4 | EtOAc | <6 | 20 |
| 5 | PhMe | <9 | 20 |

G. Reduced Catalyst Loading (50 mL Parr)

An attempt at reducing catalyst loading further was made in the 50 mL Parr vessel. A catalyst loading of 20,000/1 S/C was used with 30 bar pressure. Previous results at 10,000/1 S/C loading are included for comparison in Table 47. Notes to Table 47: a. Conversion calculated as % peak area for product vs. starting material, (prod/prod+sm)×100, peak area at 210 nm using HPLC anaylsis (reverse phase method) as 254 nm; b. Incomplete conversion resulted in partial overlap of the first enantiomer and starting material giving some error in ee measurement, number in parenthesis denotes the major peak 1=early eluting 2=late eluting; c. HPLC sample taken from crude reaction mixture as a suspension in THF as substrate has poor solubility; d. ee measured from HPLC of isolated solid; e. Available hydrogen consumed within initial 16 hrs before pressure was reset to 5 bar for a further 24 hrs; f. Hydrogen source via burette; g. Hydrogen supply via flow meter; h. L/S denotes the use of longer or shorter baffle.

H. Reaction Work-Up Method

During the course of the above described screening experiments, the analysis of the crude reactions was done after diluting with THF and heating to dissolve all solids. A number of reactions were subjected to a representative workup and isolation procedure. The solvents were first removed under reduced pressure and the crude solid taken in either 9:1 or 1:1 i-PrOH:H$_2$O mixtures, the slurry was then heated to 60-70° C. before cooling to room temperature and filtering. Results are provided in Table 48. Notes to Table 48: a. Conversion calculated as % peak area for product vs. starting material, (prod/prod+sm)×100, peak area at 210 nm using HPLC anaylsis (reverse phase method) as 254 nm; b. Incomplete conversion resulted in partial overlap of the first enantiomer and starting material giving some error in ee measurement, number in parenthesis denotes the major peak 1=early eluting 2=late eluting.

I. Scale Up Reactions in 300 mL Parr Reactor

Reaction scale up was done in the 300 mL Parr reactor. Various mechanical issues were encountered and therefore, the results were not truly representative. Another experiment was conducted after resolving mechanical issues. Although improved results were obtained, the product ee was still relatively low in comparison with previous results in the 50 mL Parr vessel. No further experiments were done using this vessel as better results were obtained in the larger 600 mL Parr vessel.

TABLE 47

| Entry | Scale (g) | Catalyst | Loading (S/C) | Solvent 1 (v %) | Solvent 2 (v %) | Solvent 3 (v %) | Baffle (L/S)[h] | Time (hr) | Temp. (° C.) | H$_2$ (bar) | Solvent (conc./M) | Conv. (%)[a] | ee (%)[b] |
|---|---|---|---|---|---|---|---|---|---|---|---|---|---|
| 1 | 6.68 | (S,S) | 10000 | IPA (80) | H$_2$O (10) | DMSO (10) | S | 64 | 60 | 5[g] | 0.6 | 58.1[c] | — |
| 2 | 6.68 | (S,S) | 10000 | IPA (80) | H$_2$O (10) | DMSO (10) | L | 64 | 70 | 5[f] | 0.6 | 99.6 | 95.0(2) |
| 3 | 6.68 | (S,S) | 20000 | IPA (80) | H$_2$O (10) | DMSO (10) | L | 48 | 70 | 30[f] | 0.6 | 99.8 | 97.2(2) |

TABLE 48

| Entry | Reaction Sample | Scale (g) | Isolation Solvents | Isolated mass (g) | Yield (%) | HPLC Prod. (%)[a] | ee (%)[b] |
|---|---|---|---|---|---|---|---|
| | No DMSO Cosolvent | | | | | | |
| 1 | Reaction mixture (THF solution) | 6.68 | — | — | — | 98.9 | 96.8(2) |
| 2 | Isolated solid | — | i-PrOH/H$_2$O (9:1, 30 mL) | 5.75 | 85.6 | 99.3 | 98.3(2) |
| 3 | Reaction mixture (THF solution) | 6.68 | — | — | — | 97.8 | 97.3(2) |
| 4 | Isolated solid | — | i-PrOH/H$_2$O (1:1, 45 mL) | 5.75 | 85.6 | 98.1 | 98.1(2) |
| | DMSO Cosolvent, 10% (v/v) | | | | | | |
| 5 | Reaction mixture (THF solution) | 6.68 | — | — | — | 90.1 | — |
| 6 | Isolated solid | — | i-PrOH/H$_2$O (1:1, 45 mL) | 5.95 | 88.6 | 92.3 | 98.9(2) |
| 7 | Reaction mixture (THF solution) | 6.68 | — | — | — | 99.6 | 95.0(2) |
| 8 | Isolated solid | — | i-PrOH/H$_2$O (9:1, 30 mL) | 5.50 | 81.9 | 99.8 | 98.8(2) |
| | DMSO Cosolvent, 20% (v/v) | | | | | | |
| 9 | Reaction mixture (THF solution) | 6.68 | — | — | — | 99.4 | 94.2(2) |
| 10 | Isolated solid | — | i-PrOH/H$_2$O (1:1, 45 mL) | 5.96 | 88.7 | 99.8 | 97.2(2) |

TABLE 49

| Entry | Scale (g) | Catalyst | Loading (S/C) | Cosolvent (v %) | Time (hr) | Temp. (° C.) | H$_2$ (bar) | Isolated yield (%) | Prod. (%)[a] | ee (%)[b] |
|---|---|---|---|---|---|---|---|---|---|---|
| 1 | 80.16 | (S,S) | 4000 | DMSO (10) | 22 | 70 | 5[f] | 89.0 | 99.5 | 99.1(2) |
| 2 | 80.16 | (S,S) | 10000 | DMSO (10) | 112 | 70 | 5[f] | 88.8 | 96.6 | 98.6(2) |

[a]Conversion calculated as % peak area for product vs. starting material, (prod/prod + sm) × 100, peak area at 210 nm using HPLC anaylsis (reverse phase method) as 254 nm.
[b]Incomplete conversion resulted in partial overlap of the first enantiomer and starting material giving some error in ee measurement, number in parenthesis denotes the major peak 1 = early eluting 2 = late eluting.
[c]HPLC sample taken from crude reaction mixture as a suspension in THF as substrate has poor solubility.
[d]ee measured from HPLC of isolated solid.
[e]Available hydrogen consumed within initial 16 hrs before pressure was reset to 5 bar for a further 24 hours.
[f]Hydrogen source via burette.
[g]Hydrogen supply via flow metre.
[h]Drying sample to constant mass ongoing, yield may be revised lower.

J. Scale Up Reactions in 600 mL Parr Reactor

The reaction conditions using DMSO (10% v/v) as co-solvent were used as the benefits in reaction rate were demonstrated previously. The 600 mL Parr vessel was equipped with an intermig impeller for efficient stirring.

Figure 7:
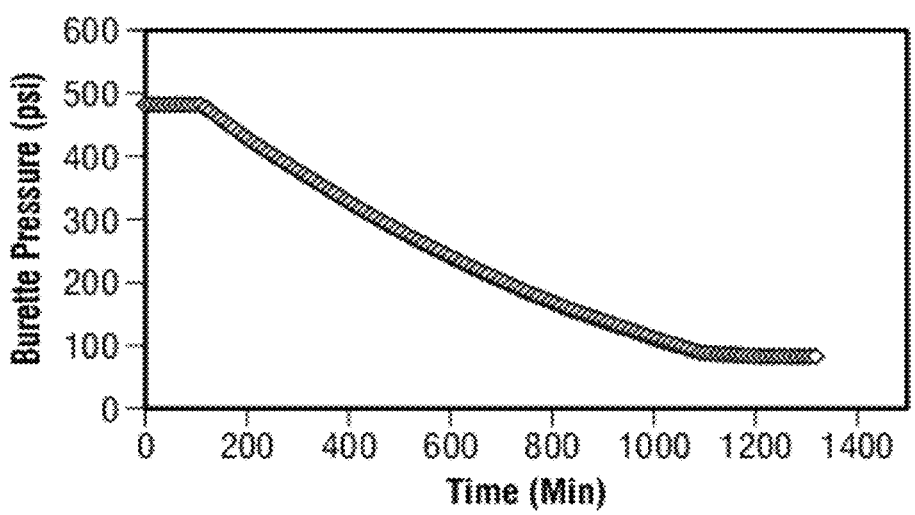
FIG. 7 provides hydrogen uptake with respect to time for hydrogenation of (4-fluorophenyl)(4-(5-methyl-4H-pyrazol-3-ylamino)quinazolin-2-yl)methanone using 10% DMSO (v/v) co-solvent with isopropyl alcohol at 70° C., hydrogen pressure of 5 bar, and catalyst loading of 4000/1 S/C.

Catalyst loading 4,000/1 S/C: The total reaction time was 22 hours as the uptake curve appeared to flatten out after around 20 hrs as seen FIG. 7. Only a minor amount of ketone was observed in the isolated product. The isolated product had good enantiopurity (99.1% ee). The isolated yield, 89%, was comparable to results obtained on a smaller scale in the 50 and 300 mL vessels. Results are provided in Table 49.

Figure 8:
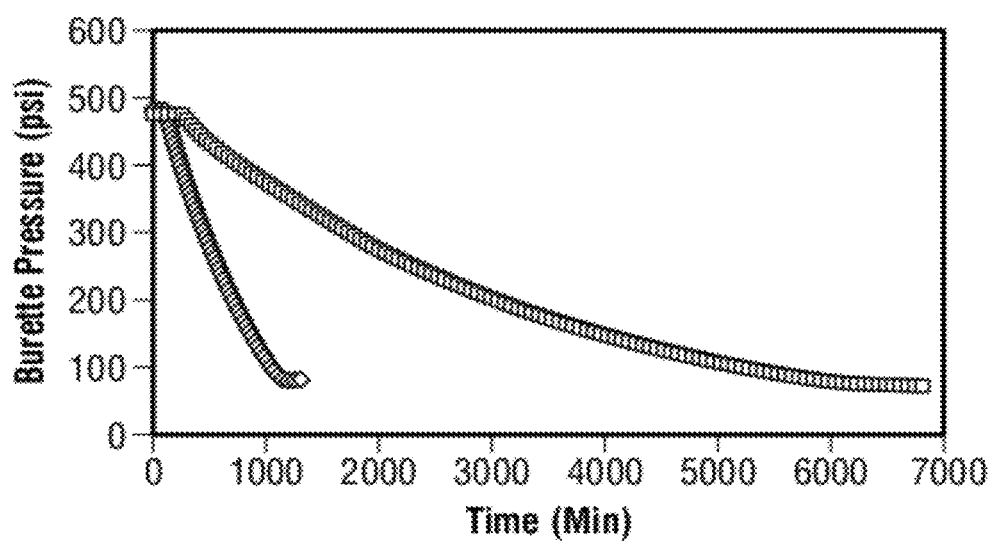
FIG. 8 provides hydrogen uptake with respect to time for hydrogenation of (4-fluorophenyl)(4-(5-methyl-4H-pyrazol-3-ylamino)quinazolin-2-yl)methanone using 10% DMSO (v/v) co-solvent with isopropyl alcohol at 70° C., hydrogen pressure of 5 bar, and catalyst loading of 10,000/1 S/C.

Catalyst loading 10,000/1 S/C: A reaction using reduced catalyst loading was also attempted using this vessel. DMSO (10% v/v) co-solvent was used. A relatively long reaction time was required until hydrogen uptake had appeared to flatten (112 hrs, see FIG. 8). Shorter reaction times were obtained using these conditions on a smaller scale (50 mL Parr) possibly due to difference in vessel mixing efficiency. The isolated product contained small quantities of ketone (3.4% by HPLC), although the product was isolated in good ee (98.6%). Results are provided in Table 49.

K. Ruthenium Content

Analysis of the ruthenium content was carried out in comparison with the catalyst loading. The estimated maximum ruthenium content in comparison with catalyst loading and actual results are shown in Table 50.

TABLE 50

| Entry | Loading (S/C) | Max. Ru Content (ppm)$^a$ | Actual Ru Content (ppm) |
|---|---|---|---|
| 1 | 2000 | 150 | 30 |
| 2 | 4000 | 75 | 3 |
| 3 | 4000 | 75 | 6 |
| 4 | 5000 | 60 | 8 |
| 5 | 4000 | 75 | 2 |
| 6 | 10000 | 30 | 2 |
| 7 | 10000 | 30 | <1 |
| 8 | 20000 | 15 | <1 |

$^a$Estimated based on initial catalyst loading and 0% ruthenium removal from product Example 24

Exemplary Scale Up Reaction in 600 mL Parr Vessel

A 600 mL Parr vessel was charged with (4-fluorophenyl)(4-(5-methyl-1H-pyrazol-3-ylamino)quinazolin-2-yl)methanone (80.16 g, 231 mmol), (S)-PPhos RuCl$_2$ (S)-DAIPEN (65.3 mg, S/C 4,000/1), a solution of i-PrOH—H$_2$O (9:1 v/v, 324 mL) and DMSO (36 mL). The vessel was sealed and purged with N$_2$ by filling to 3 bar for 1 min and then venting, further 5 purges were done with stirring (1500 rpm). A solution of t-BuOK/t-BuOH (1 M, 348 μL) in i-PrOH—H$_2$O (9:1 v/v, 10 mL) was added and the reaction purged with N$_2$ according to the previous sequence. The vessel was then purged with H$_2$ by filling to 5 bar for 2 min and venting, further 3 purges were done with stirring (1500 rpm). The reaction was then heated to 70° C. and maintained at this temperature and pressure for the indicated time.

The vessel was allowed to cool to room temperature before purging with nitrogen. The reaction slurry was diluted with H$_2$O (260 mL) and filtered. The solid was washed with i-PrOH—H$_2$O (1:1 v/v) (2×100 mL) and dried under high vacuum until constant mass was achieved. The reaction resulted in 71.75 g and isolated yield of 89.0%. HPLC analysis indicated 99.5% product and 0.5% starting material. The product enantiomeric excess of 99.1% in favour of the late eluting enantiomer.

Example 25

Two batches of (4-fluorophenyl)(4-(5-methyl-1H-pyrazol-3-ylamino)quinazolin-2-yl)methanone were screened for conversion at catalyst loads of S/C 500/1 and 2000/1. Batch 1 contained ~15% molar Et(i-Pr)$_2$N, Hunig's base and 2% molar Ac)Et. Batch 2 contained ~11% molar (3% w/w) AcOEt. The reaction were conducted in a BIOTAGE ENDEAVOR™ reactor with 1.13 g of a substrate, 0.3 mol % t-BuOK, in IPA/H$_2$O/DMSO (8:1:1, v/v/v) at 70° C. and 5 bar hydrogen for 16 hrs. Various batches of catalyst [(S)-PPhos-RuCl$_2$(S)-DAIPEN] and [(R)-PPhosRuCl$_2$(R)-DAIPEN] were used.

Batch 1 gave full conversion at both loads. Batch 2 gave full conversion with S/C 500/1, but no conversion with S/C 2000/1. Addition of 15 mol % of amine base led to slight increase of conversion for Batch 2. When recovered unreacted material was reused in reaction, improved conversions were obtained.

The results of these reactions suggested that purification of starting material combined with addition of base might resolve the poor reactivity of Batch 2.

Three basic purification procedures were used with Batch 2 (Table 51, Entries 5-7). The substrate nos. in column 2 of Table 51 are used in the Examples below to indicate the substrate batch used.

TABLE 51

| Batch No. | Substrate No. | Action (Typically performed on 5 g of subtrate) |
|---|---|---|
| 1 | 1 | None |
| 2 | 2 | None |
| 2 | 3 | Recovered material from prev. reaction |
| 2 | 4 | Drying in vacuo |
| 2 | 5 | Refluxing in IPA (70 mL), filtered upon cooling |
| 2 | 6 | Refluxing in IPA/H$_2$O (9/1) (70 mL), diluted with water (70 mL), filtered upon cooling |
| 2 | 7 | Suspended in IPA/H$_2$O (9/1) (30 mL), DIPEA (1 mol % added) Mixture stirred at 70° C. for 1 hr, diluted with water (30 mL), filtered upon cooling | a. Homogeneity of Reaction

Tests for solubility of starting material, product and their mixture at 70° C. were performed. The aim of these experiments was to find the minimum amount of DMSO necessary to dissolve reagents and create homogeneous reaction mixture. One tube contained starting material, the second one a mixture of starting material and product (1/1) to simulate situation when reaction is half complete and the third tube contained product. Experiments were started in 5 mL of IPA/DMSO/water (8/1/1), where none of the mixtures was soluble at 70° C. DMSO was then added dropwise until full solubility could be reached. It was found that upon addition of additional 5 mL DMSO, full solubility of product was reached, while the mixture of starting material and product could be dissolved upon addition of 7 mL of DMSO. At these conditions, starting material was still partially undissolved. This experiment was used to determine the necessary amounts of DMSO to create a homogeneous reaction mixture (upon keeping the original quantities of IPA and water). Results of solubility tests of 1.113 g of material at 70° C. are provided in Table 52.

In Table 52, ketone refers to (4-fluorophenyl)(4-(5-methyl-1H-pyrazol-3-ylamino)quinazolin-2-yl)methanone and alcohol refers to (R)-(4-fluorophenyl)(4-((5-methyl-1H-pyrazol-3-yl)amino)quinazolin-2-yl)methanol or (S)-(4-fluorophenyl)(4-((5-methyl-1H-pyrazol-3-yl)amino)quinazolin-2-yl)methanol.

TABLE 52

| Entry | Substrate Composition | IPA (mL) | Water (mL) | DMSO (mL) | Result |
|---|---|---|---|---|---|
| 1 | Ketone | 4 | 0.5 | 0.5 | Not dissolved |
| 2 | Ketone/Alcohol (1/1) | 4 | 0.5 | 0.5 | Not dissolved |
| 3 | Alcohol | 4 | 0.5 | 0.5 | Not dissolved |
| 4 | Ketone | 4 | 0.5 | 5.5 | Not dissolved |
| 5 | Ketone/Alcohol (1/1) | 4 | 0.5 | 5.5 | Not dissolved |
| 6 | Alcohol | 4 | 0.5 | 5.5 | Dissolved |
| 7 | Ketone | 4 | 0.5 | 7.5 | Not dissolved |
| 8 | Ketone/Alcohol (1/1) | 4 | 0.5 | 7.5 | Dissolved |
| 9 | Alcohol | 4 | 0.5 | 7.5 | Dissolved | b. Reactivity of Purified Substrates

Reactions of purified substrates were run in Endeavor at 2000/1 catalyst loading of [(S)-PPhos RuCl$_2$ (S)-DAIPEN] with various quantities of t-BuOK (used as 1M solution of t-BuOK in t-BuOH). Reactions were performed at 3.33 mmol scale using 2000/1 loading of catalyst in 5 mL IPA/DMSO/water (8/1/1), 5 bar H$_2$ and 70° C. over 16 hrs. It was found that purifications were beneficial. Results of effect of base and purification are provided in Table 53. Substrates used in this experiment were obtained as described in Example 25, Table 51.

TABLE 53

| Entry | t-BuOK (mol %) | Substrate | Conv. (%)$^a$ | ee (%)$^b$ |
|---|---|---|---|---|
| 1 | 0.3 | 1 | 99+ | ND |
| 2 | 0.3 | 2 | 0 | ND |
| 3 | 1 | 2 | 18 | ND |
| 4 | 2.5 | 2 | 34 | ND |
| 5 | 1 | 3 | 93 | 99 |
| 6 | 2.5 | 3 | 96 | 99 |
| 7 | 1 | 4 | 21 | ND |
| 8 | 2.5 | 4 | 57 | ND |
| 9 | 5 | 4 | 94 | 99+ |
| 10 | 1 | 5 | 91 | ND |
| 11 | 2.5 | 5 | 97 | ND |
| 12 | 0.3 | 6 | 55 | ND |
| 13 | 1 | 6 | 97 | ND |
| 14 | 2.5 | 6 | 95 | 99+ |
| 15 | 5 | 6 | 98 | 99+ |
| 16 | 0.3 | 7 | 75 | ND |
| 17 | 1 | 7 | 96 | ND |
| 18 | 2.5 | 7 | 97 | 99+ |
| 19 | 5 | 7 | 98 | 99+ |

Example 26

Reactions in BIOTAGE ENDEAVOR™ Reactor (3.33 mmol Scale)

An BIOTAGE ENDEAVOR™ vial was charged with substrate (1.113 g, 3.33 mmol). IPA (1 mL), DMSO (0.5 mL) and water (0.5 mmol) were added successively. The vial was placed into the BIOTAGE ENDEAVOR™ and the system was purged with nitrogen by pressurizing to 3 bar and releasing pressure. 3 mL of catalyst stock solution, prepared by dissolving [(S)-PPhos RuCl$_2$ (S)-DAIPEN] (5.4 mg, 0.005 mmol) in IPA (12 mL) and adding solution of t-BuOK in t-BuOH (typically 666 mL for 5 mol %), was injected to each BIOTAGE ENDEAVOR™ reactor and the reaction mixture was purged with nitrogen (5×) and hydrogen (5×). Reaction mixture was stirred for 16 hrs at 4-5 bar (see Table 54) and 70° C. The reaction mixture was allowed to cool, depressurized and the contents of the reaction vial were transferred to a 100 mL Erlenmeyer flask using 70 mL THF. This typically resulted in clear yellow solution. In some cases, an orange solution with undissolved solid was obtained, which indicated low/incomplete conversion. A sample was taken and reaction conversion and ee were determined by HPLC. Results are provided in Table 54. Substrates used in this experiment were obtained as described in Example 25, Table 51.

Example 27

A. Parr Autoclave Reactions (20 mmol Scale)

A Parr autoclave was charged with substrate (6.68 g, 20 mmol) and closed. Through the injection port, IPA (12 mL), DMSO (3 mL) and water (3 mmol) were added successively (autoclave was purged with nitrogen 5×). The catalyst solution prepared by dissolving [(S)-PPhos RuCl$_2$ (S)-DAIPEN] or [(R)-PPhos RuCl$_2$ (R)-DAIPEN] (5.4 mg, 0.005 mmol) in IPA (11 mL) and adding solution of t-BuOK in t-BuOH (typically 1 mL for 5 mol %) was added. The reactor was purged with nitrogen (5×) and hydrogen (5×). The reaction mixture was stirred for 16 hrs at 5 bar and 70° C. The reaction mixture was cooled down, depressurized and the contents of reactor were transferred to a 100 mL Erlenmeyer flask containing 30 mL water. Precipitate was filtered off, washed with IPA/water (15 mL, 9/1) and dried in vacuo giving the corresponding alcohol. A sample was prepared and reaction conversion and ee were determined by HPLC. Results are provided in Table 55 below. Substrates used in this experiment were obtained as described in Example 25, Table 51.

B. Parr Autoclave Reactions (10 mmol Scale)—Homogeneous System

A Parr autoclave was charged with substrate (3.34 g, 10 mmol) and closed. Through the injection port, IPA (7 mL), DMSO (14 mL) and water (2 mL) were added successively (the autoclave was purged with nitrogen at least five times). 7 mL of catalyst solution prepared by dissolving [(S)-PPhos RuCl$_2$ (S)-DAIPEN] or [(R)-PPhos RuCl$_2$ (R)-DAIPEN] (5.4 mg, 0.005 mmol) in IPA (13 mL) and adding solution of t-BuOK in t-BuOH (1 mL for 5 mol %) was added. The reactor was purged with nitrogen (5×) and hydrogen (5×). The reaction mixture was stirred for 16 hrs at 4 bar and 70° C. The reaction mixture was allowed to cool and depressurized. A sample was taken and reaction conversion and ee were determined by HPLC. The contents of the reactor were added drop wise under vigorous stirring to a 100 mL Erlenmeyer flask containing 30 mL water. Thick white precipitate formed immediately. The precipitate was filtered off, washed with water (15 mL) and dried in vacuum giving the corresponding alcohol. Results are provided in Table 55 below. Substrates used in this experiment were obtained as described in Example 25, Table 51.

Example 28

Scale Up Reactions at 4 Bars

Scale up reactions for preparing (R)-(4-fluorophenyl)(4-((5-methyl-1H-pyrazol-3-yl)amino)quinazolin-2-yl)methanol and (S)-(4-fluorophenyl)(4-((5-methyl-1H-pyrazol-3-yl)amino)quinazolin-2-yl)methanol using 10 g (4-fluorophenyl)(4-(5-methyl-1H-pyrazol-3-ylamino)quinazolin-2-yl)methanone and [(S)-PPhos RuCl$_2$ (S)-DAIPEN] or [(R)-PPhos RuCl$_2$ (R)-DAIPEN] were performed at 70° C. and 4H$_2$ bars using procedures similar to that described in Example 27B. Tables 56 and 57 below summarize the procedures and results. In Tables 56 and 57 below, R-enantiomer refers to (R)-(4-fluorophenyl)(4-(5-methyl-1H-pyrazol-3- ylamino)quinazolin-2-yl)methanol, and S-enantiomer refers to (S)-(4-fluorophenyl)(4-(5-methyl-1H-pyrazol-3-ylamino)quinazolin-2-yl)methanol.

For the last three entries in Table 53, the following procedure for used for work up. The final reaction mass solution was dosed to IPA/water mixture under stirring at 0-5° C. to precipitate the product. After filtration over 10 microns, the wet product was washed with IPA and water. According to the assay data, the mother liquors typically contained about 10% of material and about 1% in the washing liquors. The drying was performed at 5 0° C.

Formation of Esylate Salt

The products of last three entries in Table 56 were used for formation of esylate salts. All esylate salt formation reactions were run under conditions described in Table 57 with 1 equivalent of $EtSO_3H$ amount, the reaction time was 30 min at reflux and the mass was cooled to 5° C. for the product isolation.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

TABLE 54

| Entry | tBuOK (mol %) | Substrate | Solvent(s) | Loading (S/C) | Time (hr) | Temp. (° C.) | $H_2$ (bar) | Solvent (conc./M) | Conv. (%) | ee (%) |
|---|---|---|---|---|---|---|---|---|---|---|
| 1 | 1 | 3 | IPA/DMSO/water 8/1/1 | 2000 | 16 | 70 | 5 | 0.6 | 93 | 99 |
| 2 | 2.5 | 3 | IPA/DMSO/water 8/1/1 | 2000 | 16 | 70 | 5 | 0.6 | 96 | 99 |
| 3 | 1 | 2 | IPA/DMSO/water 8/1/1 | 2000 | 16 | 70 | 5 | 0.6 | 18 | ND |
| 4 | 1 | 4 | IPA/DMSO/water 8/1/1 | 2000 | 16 | 70 | 5 | 0.6 | 21 | ND |
| 5 | 1 | 5 | IPA/DMSO/water 8/1/1 | 2000 | 16 | 70 | 5 | 0.6 | 91 | ND |
| 6 | 2.5 | 2 | IPA/DMSO/water 8/1/1 | 2000 | 16 | 70 | 5 | 0.6 | 34 | ND |
| 7 | 2.5 | 4 | IPA/DMSO/water 8/1/1 | 2000 | 16 | 70 | 5 | 0.6 | 57 | ND |
| 8 | 2.5 | 5 | IPA/DMSO/water 8/1/1 | 2000 | 16 | 70 | 5 | 0.6 | 97 | ND |
| 9 | 0.3 | 6 | IPA/DMSO/water 8/1/1 | 2000 | 16 | 70 | 5 | 0.6 | 55 | ND |
| 10 | 1 | 6 | IPA/DMSO/water 8/1/1 | 2000 | 16 | 70 | 5 | 0.6 | 97 | 99+ |
| 11 | 2.5 | 6 | IPA/DMSO/water 8/1/1 | 2000 | 16 | 70 | 5 | 0.6 | 95 | 99+ |
| 12 | 5 | 6 | IPA/DMSO/water 8/1/1 | 2000 | 16 | 70 | 5 | 0.6 | 98 | 99+ |
| 13 | 5 | 4 | IPA/DMSO/water 8/1/1 | 2000 | 16 | 70 | 5 | 0.6 | 94 | 99+ |
| 14 | 0.3 | 7 | IPA/DMSO/water 8/1/1 | 2000 | 16 | 70 | 5 | 0.6 | 75 | ND |
| 15 | 1 | 7 | IPA/DMSO/water 8/1/1 | 2000 | 16 | 70 | 5 | 0.6 | 96 | ND |
| 16 | 2.5 | 7 | IPA/DMSO/water 8/1/1 | 2000 | 16 | 70 | 5 | 0.6 | 97 | 99+ |
| 17 | 5 | 7 | IPA/DMSO/water 8/1/1 | 2000 | 16 | 70 | 5 | 0.6 | 98 | 99+ |
| 18 | 0.3 | 1 + EtoAc (10 mol %) | IPA/DMSO/water 8/1/1 | 2000 | 16 | 70 | 5 | 0.6 | 98 | ND |
| 19 | 5 | 4 | IPA/DMSO/water 4/4/0.5 | 2000 | 16 | 70 | 5 | 0.3 | quant. | ND |
| 20 | 5 | 2 | IPA/DMSO/water 8/1/1 | 2000 | 16 | 70 | 4 | 0.6 | 97 | 99+ |
| 21 | 5 | 2 | IPA/DMSO/water 8/1/1 | 2000 | 16 | 70 | 4 | 0.6 | 98 | 99+ |
| 22 | 5 | 2 | IPA/DMSO/water 8/1/1 | 2000 | 16 | 70 | 4 | 0.6 | 98 | 99+ |
| 23 | 5 | 2 | IPA/DMSO 4/4 | 2000 | 16 | 70 | 4 | 0.3 | quant. | 99+ |

TABLE 55

| Entry | Scale (g) | Catalyst (R/S) | tBuOK (mol %) | Solvent(s) | Substrate | Loading (S/C) | Time (hr) | Temp. (° C.) | $H_2$ (bar) | Solvent (conc./M) | Conv. (%) | ee (%) |
|---|---|---|---|---|---|---|---|---|---|---|---|---|
| 1 | 6.68 | (S/S) | 0.3 | IPA/DMSO/water 8/1/1 | 1 | 4000 | 16 | 70 | 5 | 0.6 | quant | 99+ |
| $2^a$ | 6.68 | (S/S) | 0.3 | IPA/DMSO/water 8/1/1 | 1 | 4000 | 16 | 70 | 5 | 0.6 | quant | 99+ |
| $3^a$ | 6.68 | (R/R) | 0.3 | IPA/DMSO/water 8/1/1 | 1 | 4000 | 16 | 70 | 5 | 0.6 | 97 | 99+ |
| 4 | 6.68 | (S/S) | 10 | IPA/DMSO/water 8/1/1 | 2 | 4000 | 16 | 70 | 5 | 0.6 | 94 | 99+ |
| 5 | 3.34 | (S/S) | 5 | IPA/DMSO/water 47/47/6 | 2 | 4000 | 16 | 70 | 4 | 0.3 | quant. | >99 |
| $6^a$ | 3.34 | (R/R) | 5 | IPA/DMSO 50/50 | 2 | 4000 | 16 | 70 | 4 | 0.3 | quant. | >84 |
| $7^a$ | 3.34 | (R/R) | 5 | IPA/DMSO/water 47/47/6 | 2 | 4000 | 16 | 70 | 4 | 0.3 | quant. | 97 |
| 8 | 3.34 | (R/R) | 5 | | 2 | 4000 | 16 | 70 | 4 | 0.3 | quant. | 97 |

$^a$Slow stirring (approx 200 rpm). All other reactions were stirred at >1200 rpm.

TABLE 56

| | Mixture of solvent (w/w) | | | Base | | Catalyst amount | Stirring speed (rpm) | Time (hr) | IPC Conversion to S-enantiomer or R-enantiomer | ee (%) |
|---|---|---|---|---|---|---|---|---|---|---|
| Catalyst | IPA | DMSO | Water | Type | Amount (M) | | | | | |
| S | 44% | 50% | 6% | tBuOK | 5% | 4000 | 600 | 20.5 | 65% | 98.7 |
| S | 18% | 79% | 3% | | 5% | 4000 | 1200 | 50.5 | 17% | — |
| | | | | | 10% | 2000 | | +20 | 98.7% | 98* |
| S | 34% | 66% | 0% | | 5% | 4000 | | 23 | 44.2% | 92.3 |
| | | | | | 12.5% | 2000 | | +66 | 98.1% | 46.4 |
| S | 41% | 58% | 1% | KOH | 5% | 2000 | | 20 | 99.4% | 95.6 |
| S | 41% | 58% | 1% | KOH | 5% | 3000 | | 22 | 99.7% | — |
| R | 41% | 58% | 1% | KOH | 5% | 4000 | | +23.5 | ND | — |

TABLE 57

| Starting material | Ratio ethanol/enantiomer (v/v) | Addition of DMSO | Crystallization temperature (° C.) | Stirring time at 5° C. | Use of antisolvent (solvent/enantiomer, w/w) | Wash of the solid | Yield |
|---|---|---|---|---|---|---|---|
| S-enantiomer | 10:1 | — | ≈66 | 1 hr | — | Cold ethanol | 72.0% |
| S-enantiomer | 10:1 | 5% | ≈40 | 1 hr | Ethylacetate (5:1) | Cold isopropanol | 84.2% |
| S-enantiomer | 20:1* | 5% | <5 | 16 hrs | Ethylacetate (5:1) | | ~55% |
| R-enantiomer | 10:1 | — | ≈78 | ~1.5 hrs | — | | ND |

*Half of ethanol amount (90 g) distilled off at 78° C., because the product didn't precipitate at 5° C.

What is claimed is:

1. An optically active (S)-(4-fluorophenyl)(4-((5-methyl-1H-pyrazol-3-yl)amino)quinazolin-2-yl)methanol or an isotopic variant thereof; or pharmaceutically acceptable salt, solvate, hydrate, or prodrug thereof; wherein the compound has an enantiomeric excess of no less than 80%.

2. The compound of claim 1, wherein the compound is a salt.

3. The compound of claim 2, wherein the salt is a hydrochloride salt.

4. The compound of claim 2, wherein the salt is an esylate salt.

5. The compound of claim 1, having an enantiomeric excess of no less than 90%.

6. The compound of claim 5, having an enantiomeric excess of no less than 95%.

7. The compound of claim 1, wherein the compound is substantially pure.

8. The compound of claim 1, having an enantiomeric excess of no less than 90%.

9. The compound of claim 5, having an enantiomeric excess of no less than 95%.

10. The compound of claim 1, wherein the compound selectively inhibits JAK2.

11. The compound of claim 10, wherein the compound selectively inhibits JAK2 over JAK3.

12. A pharmaceutical composition comprising the compound of claim 1, and a pharmaceutically acceptable excipient.

13. The pharmaceutical composition of claim 12, wherein the composition is formulated for oral, nasal, bronchial, or topical administration.

14. The pharmaceutical composition of claim 12, wherein the composition is formulated as a single dosage form.

15. The pharmaceutical composition of claim 12, wherein the composition is formulated as oral, parenteral, nasal, respiratory, pulmonary, or intravenous dosage form.

16. The pharmaceutical composition of claim 15, wherein the oral dosage form is a tablet or capsule.

17. The pharmaceutical composition of claim 12, wherein the pharmaceutically acceptable excipient is PEG 400.

18. The pharmaceutical composition of claim 12, wherein the pharmaceutically acceptable excipient is water.

19. The pharmaceutical composition of claim 17, wherein the composition is formulated for intravenous administration.

* * * * *